(12) United States Patent
Harano et al.

(10) Patent No.: US 6,730,080 B2
(45) Date of Patent: May 4, 2004

(54) ELECTRIC OPERATION APPARATUS

(75) Inventors: Kenji Harano, Hachioji (JP); Masahide Ohyama, Hino (JP); Kazuya Hijii, Hachioji (JP); Koji Yamauchi, Koganei (JP); Shinji Hatta, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/929,744

(22) Filed: Aug. 14, 2001

(65) Prior Publication Data

US 2002/0052598 A1 May 2, 2002

(30) Foreign Application Priority Data

| Aug. 23, 2000 | (JP) | ................................ | 2000-252831 |
| Aug. 31, 2000 | (JP) | ................................ | 2000-263860 |
| Sep.  1, 2000 | (JP) | ................................ | 2000-265534 |

(51) Int. Cl.⁷ ............................................. A61B 18/18
(52) U.S. Cl. .................................... 606/38; 606/34
(58) Field of Search ......................... 606/34, 35, 37–40

(56) References Cited

U.S. PATENT DOCUMENTS

| 5,318,563 A | * | 6/1994 | Malis et al. ................... 606/38 |
| 5,496,312 A | * | 3/1996 | Klicek ........................... 606/34 |
| 5,540,684 A |   | 7/1996 | Hassler, Jr. |
| 5,707,369 A | * | 1/1998 | Vaitekunas et al. ........... 606/31 |
| 5,817,093 A | * | 10/1998 | Williamson et al. .......... 606/50 |
| 6,050,994 A | * | 4/2000 | Sherman ....................... 606/42 |

FOREIGN PATENT DOCUMENTS

JP          10-225462          8/1998

* cited by examiner

*Primary Examiner*—Michael Peffley
(74) *Attorney, Agent, or Firm*—Scully, Scott, Murphy & Presser

(57) ABSTRACT

When a user steps on a footswitch, high-frequency output power is delivered. A control circuit included in a diathermic power supply calculates the impedance ZSn that is offered by a living tissue immediately after delivery of high-frequency output power is started during the n-th delivery period. The control circuit also calculates the impedance ZEn that is offered thereby immediately before delivery of high-frequency output power is discontinued with elapse of predetermined time. The control circuit then discontinues delivery of high-frequency output power for the predetermined time, and calculates a difference ΔZn between the impedances. When the difference meets a predetermined condition that implies coagulation or when the number of times of delivery reaches a predetermined value, the control circuit discontinues delivery of high-frequency output power.

4 Claims, 51 Drawing Sheets

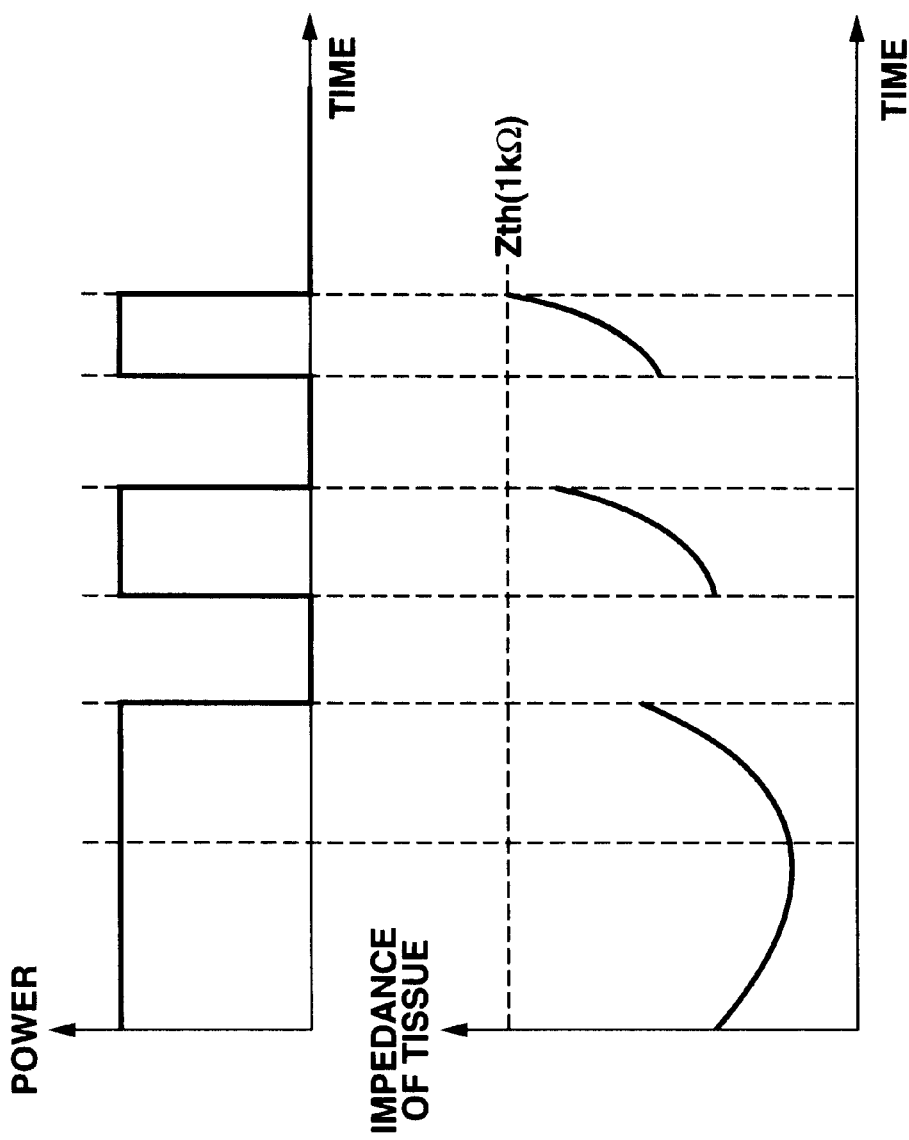

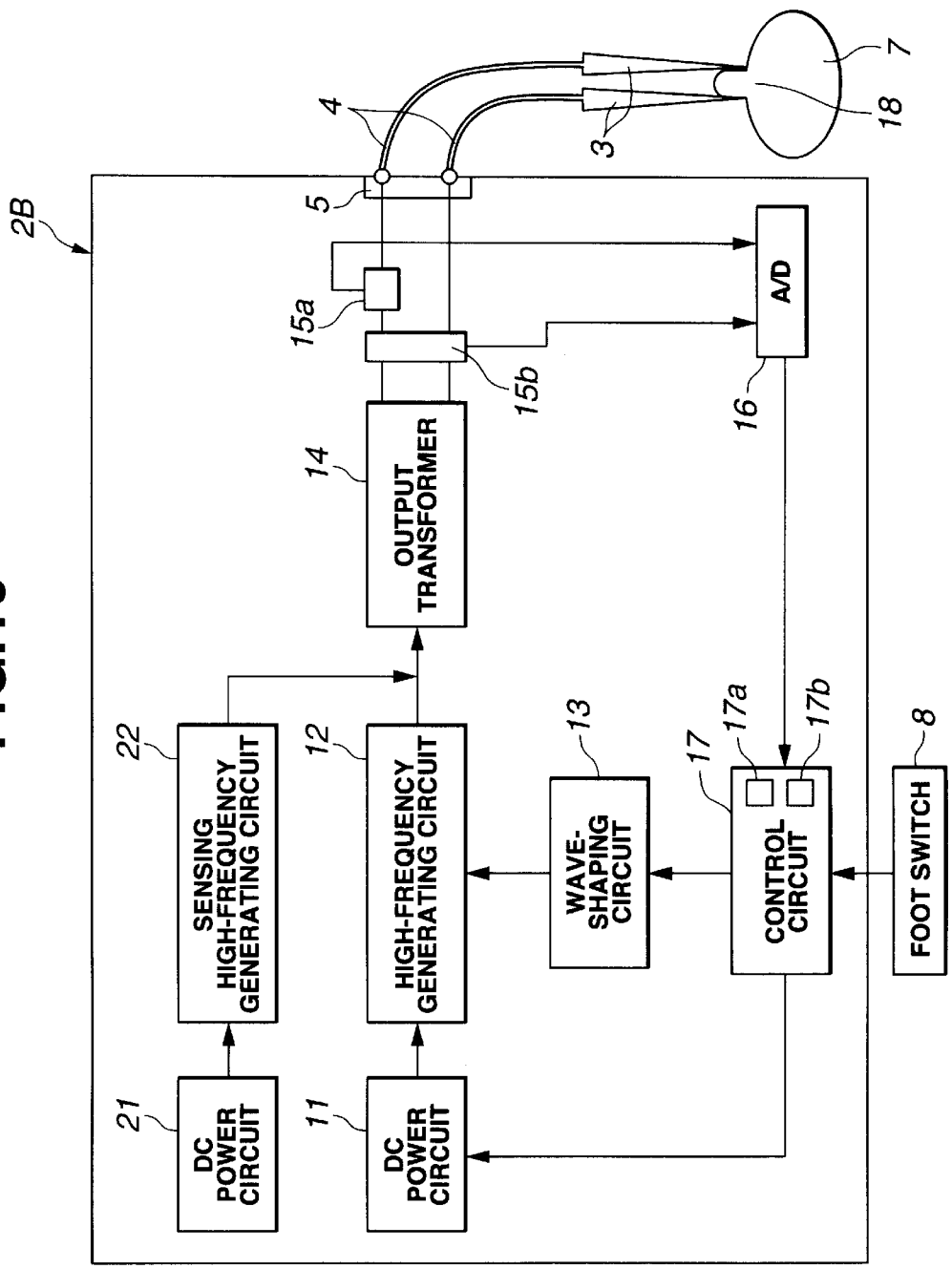

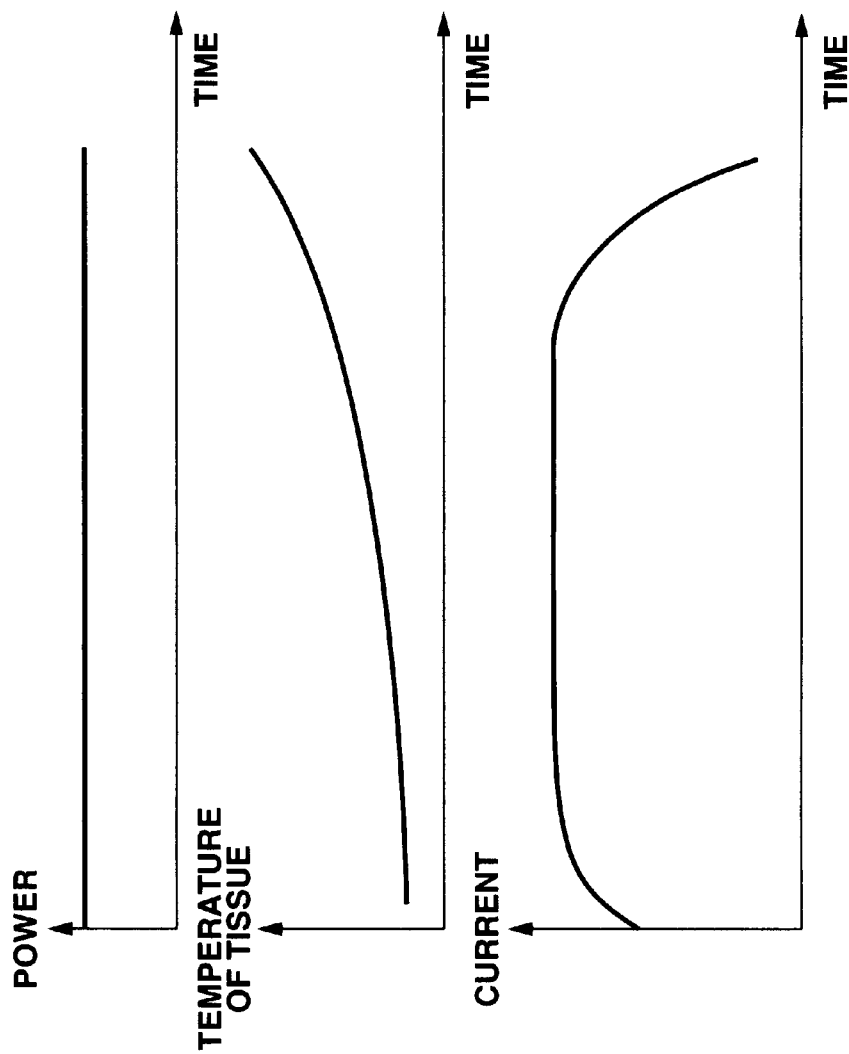

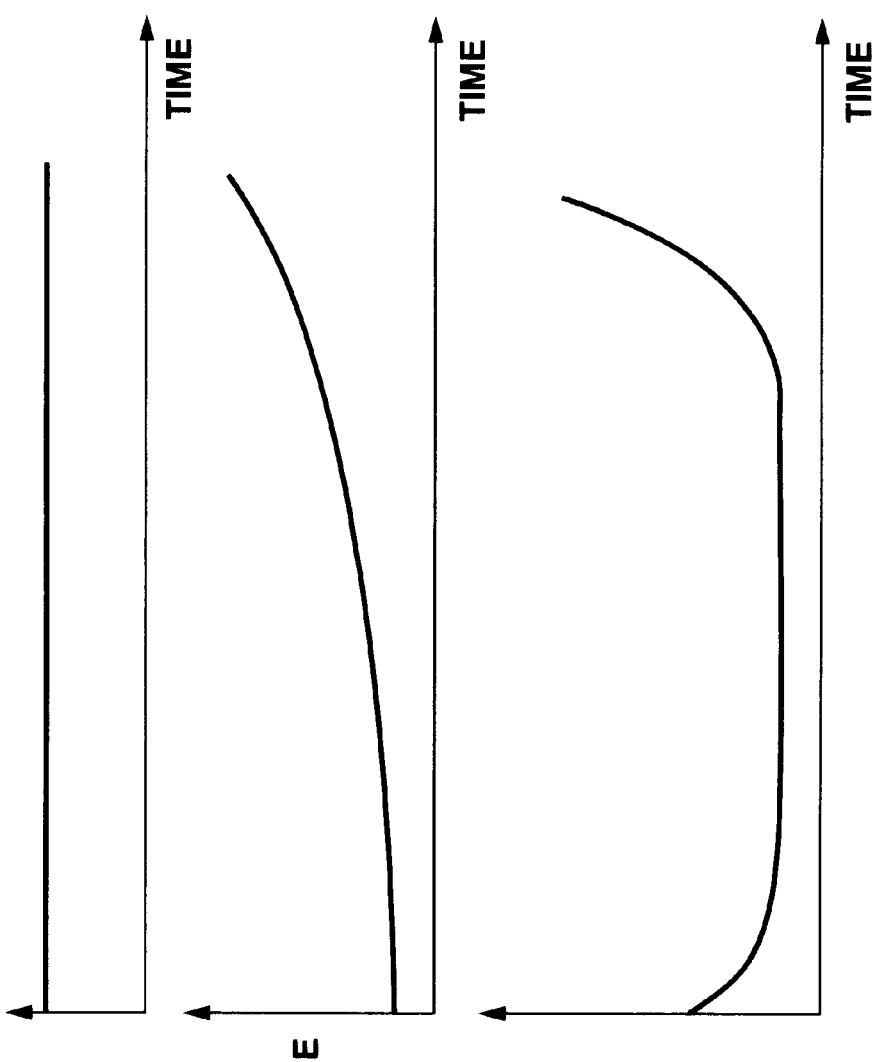

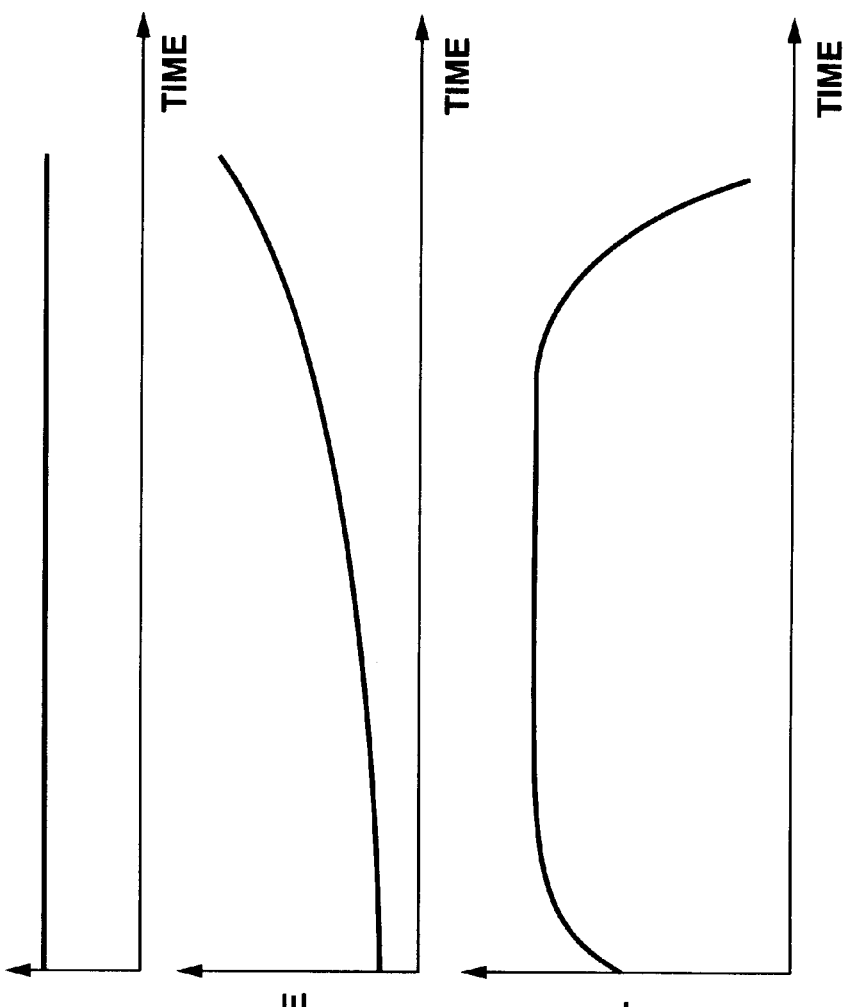

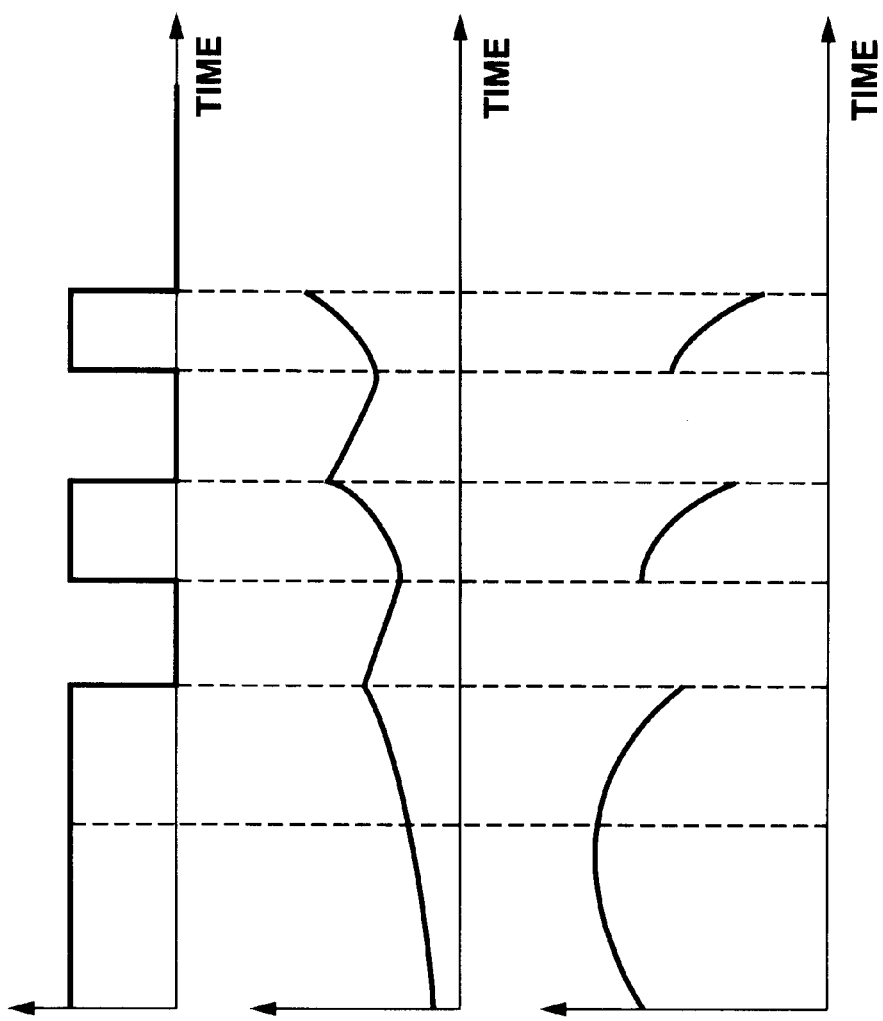

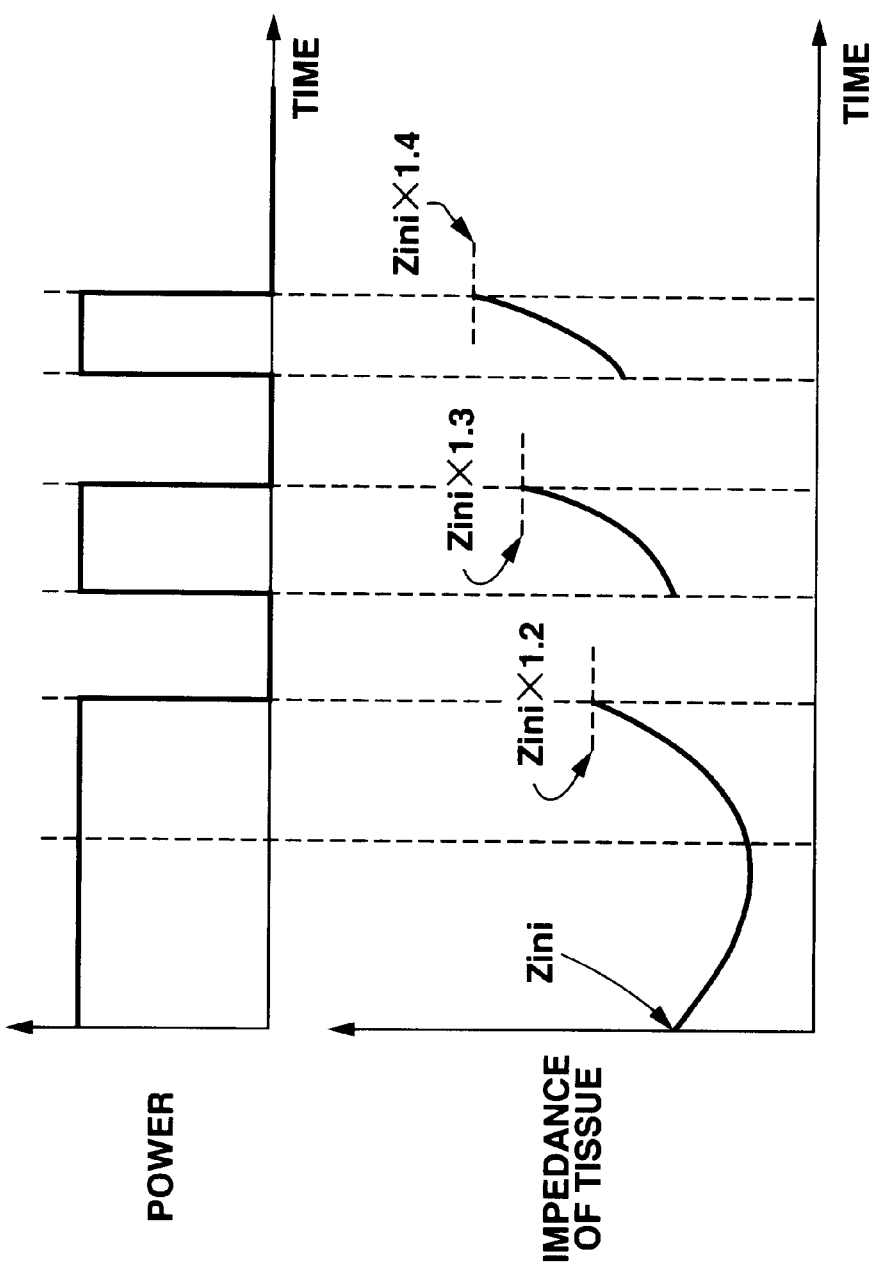

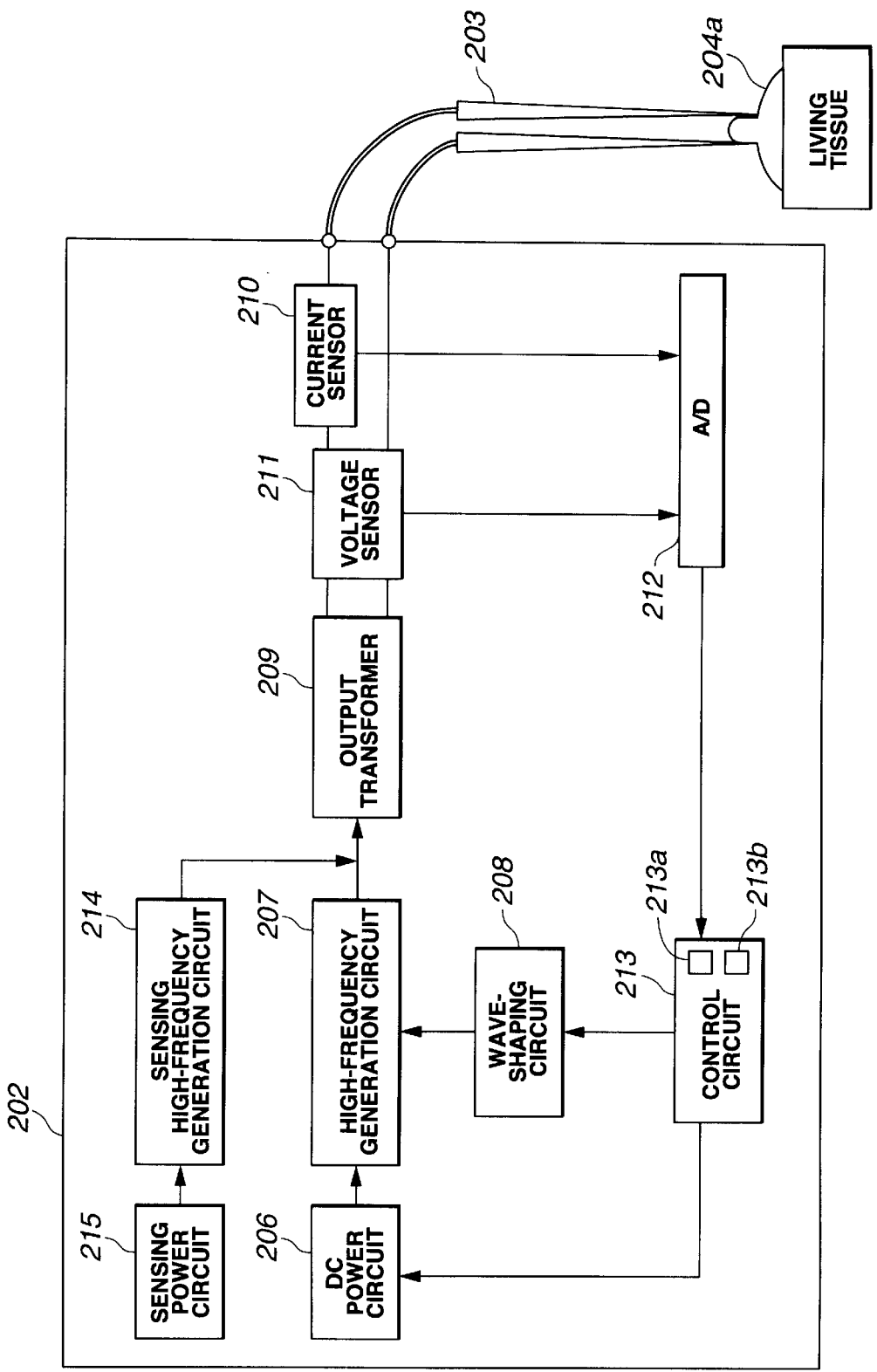

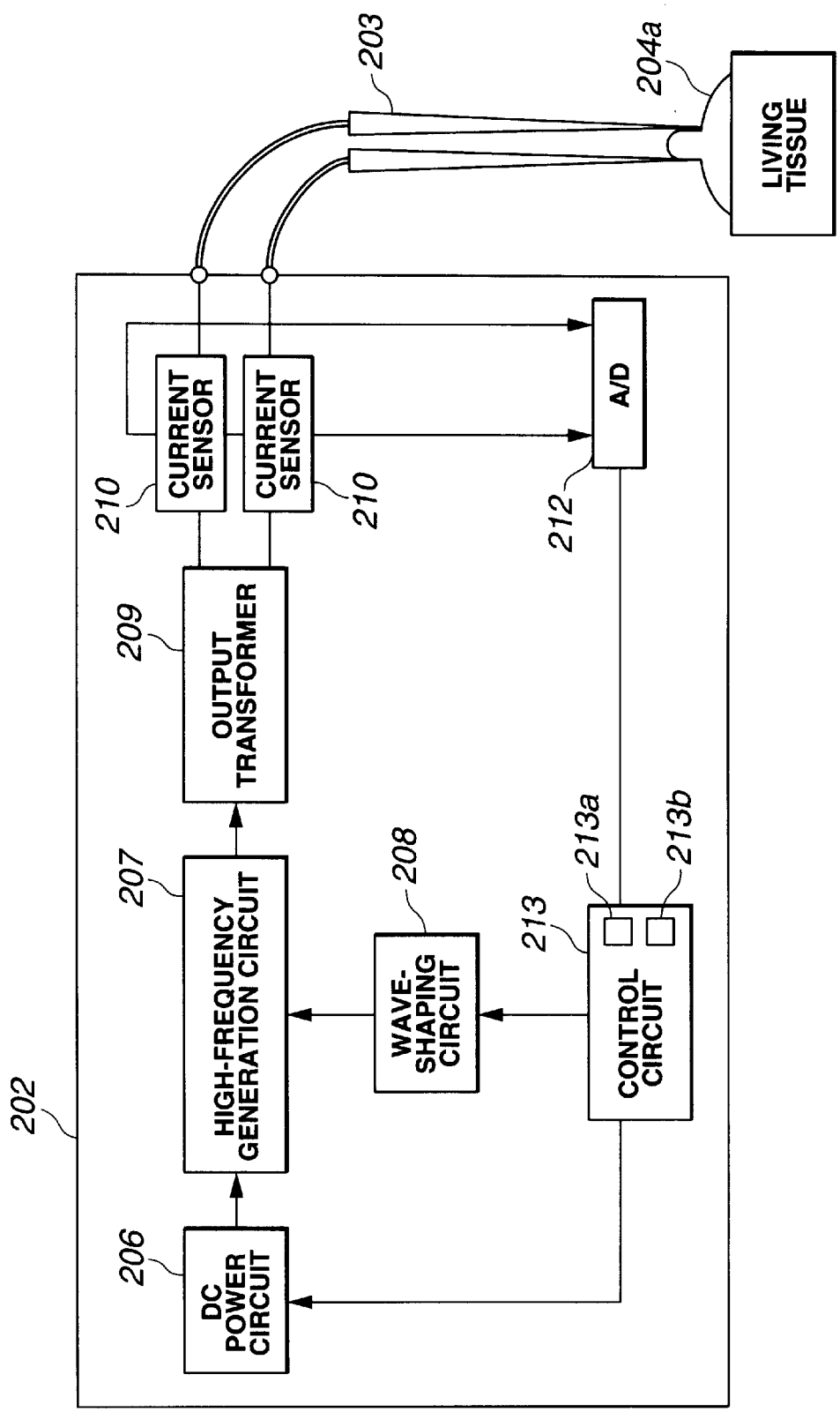

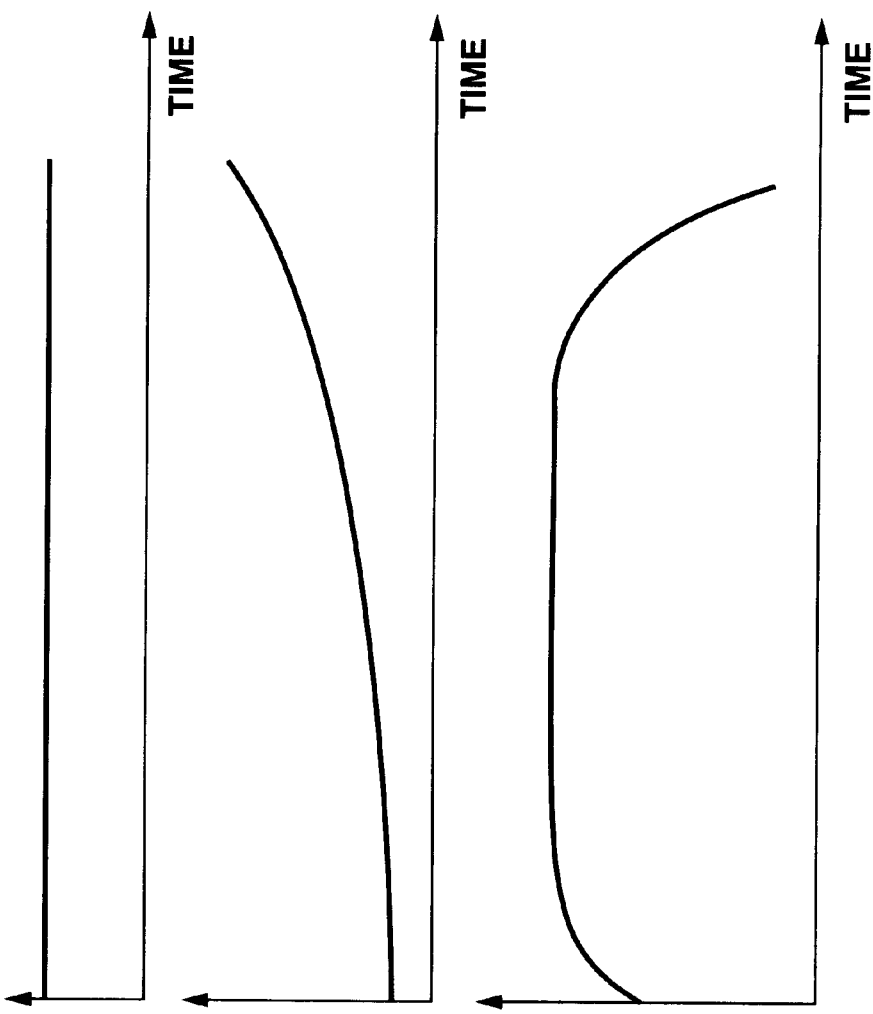

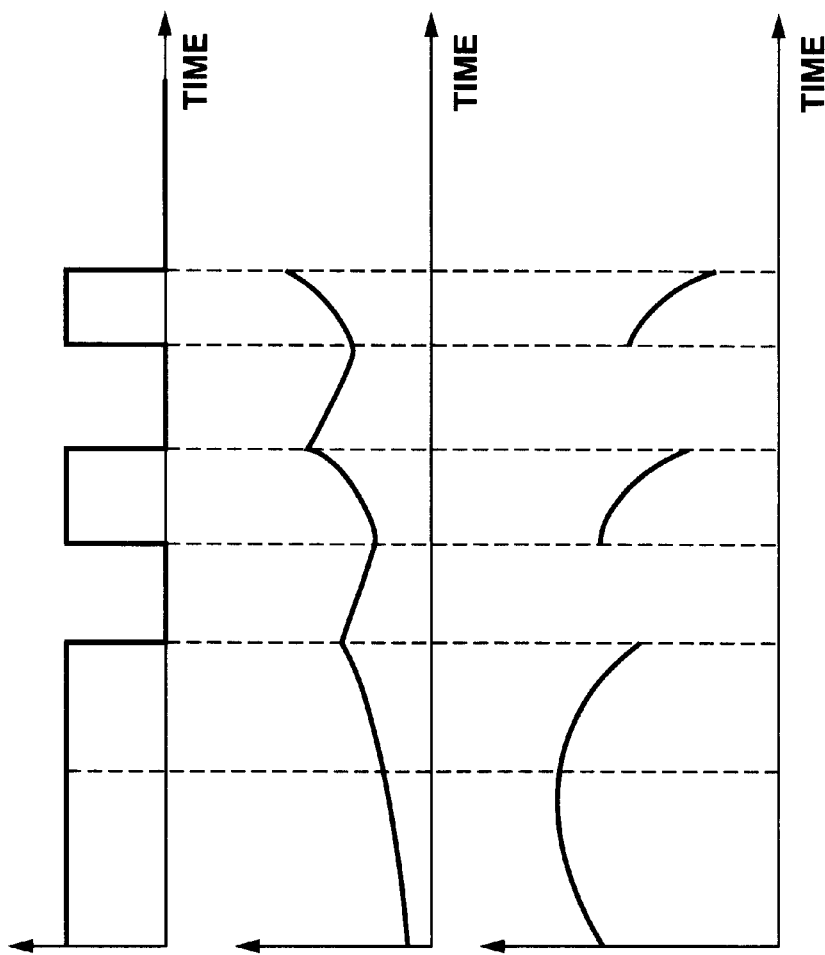
FIG.48A POWER
FIG.48B TEMPERATURE OF TISSUE
FIG.48C CURRENT

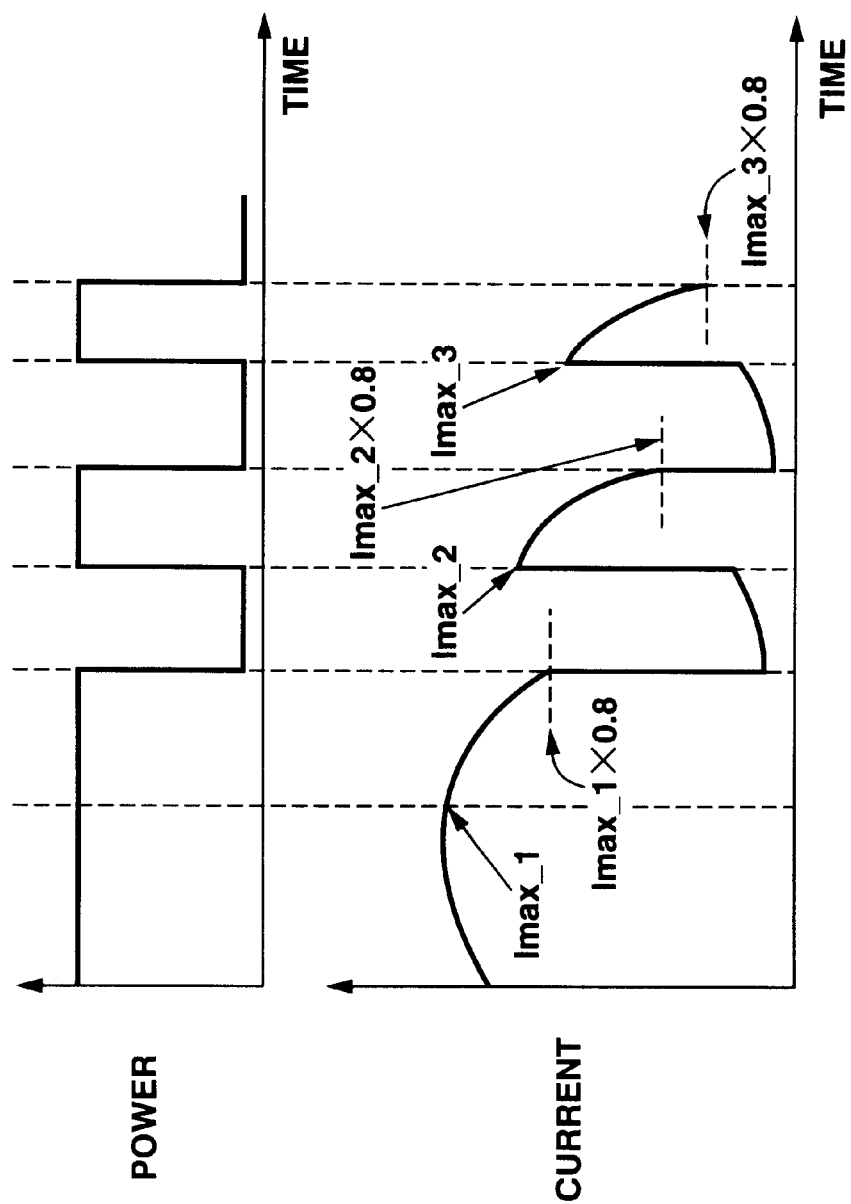

ELECTRIC OPERATION APPARATUS

This application claims benefit of Japanese Applications No. 2000-252831 filed in Japan on Aug. 23, 2000, No. 2000-263860 filed in Japan on Aug. 31, 2000, No. 2000-265534 filed in Japan on Sep. 1, 2000, the contents of which are incorporated by this reference.

BACKGROUND OF THE INVENTION

1. Field of the Invention

The present invention relates to an electric operation apparatus, or more particularly, to an electric operation apparatus characterized by an output control unit with which high-frequency current is conducted.

2. Description of the Related Art

In general, an electric operation apparatus including an electric cautery is used to incise or coagulate a living tissue or arrest bleeding from a living tissue in the course of a surgical or an internal operation for remedying a bodily injury or a disease or dysfunction.

This kind of electric operation apparatus consists mainly of a diathermic power supply and an electrode that serves as a therapeutic accessory (operating instrument) and is connected to the diathermic power supply. In the electric operation apparatus, the electrode is brought into contact with a patient's living tissue, and high-frequency output power is delivered from the diathermic power supply. Consequently, the patient's living tissue is remedied with high-frequency current conducted with the output power.

When the electric operation apparatus is used to deliver high-frequency output power to a living tissue, the living tissue is heated with high-frequency current conducted with the output power. Consequently, the living tissue is denatured, and then has water thereof depleted. Eventually, the living tissue dries up. The living tissue is coagulated in due course. Although the living tissue gets dried up, if high-frequency output power is kept delivered, the living tissue is carbonized to adhere to the electrode. In order to prevent a living tissue from adhering to the electrode, when the living tissue gets dried up, delivery of high-frequency output power must be stopped.

In the conventional electric operation apparatus, when high-frequency output power of a constant level shown in FIG. 18A is delivered to a living tissue irrespective of passage of time, the living tissue is denatured and dried up. Consequently, the temperature exhibited by the living tissue gradually rises as shown in FIG. 18B. On the other hand, as shown in FIG. 18C, the impedance offered by the living tissue decreases in an early stage, remains nearly constant for some time, and then abruptly rises along with the dry of the living tissue. Therefore, as far as the conventional electric operation apparatus is concerned, as soon as it is judged from the impedance or temperature of a living tissue that the living tissue is dried up, delivery of high-frequency output power is stopped or any other control sequence is performed.

Various proposals have been made of the foregoing electric operation apparatus in the past. For example, U.S. Pat. No. 5,540,684 has proposed an electric operation apparatus that judges from the impedance offered by a living tissue whether the living tissue has been coagulated, and stops delivery of high-frequency output power when the living tissue has been coagulated. Thus, carbonization of a coagulated living tissue is prevented and adhesion of the living tissue to an electrode is avoided.

Moreover, the present applicant has filed Japanese Patent Unexamined Publication No. 10-225462 and proposed an electric operation apparatus that lowers high-frequency output power so as to accomplish the same object as the U.S. Pat. No. 5,540,684.

In the electric operation apparatuses described in the Japanese Patent Unexamined Publication No. 10-225462 and the U.S. Pat. No. 5,540,684, when a living tissue to be coagulated has a very large volume, output power with which high-frequency current is conducted must be raised in order to exert a satisfactory coagulation ability. For this reason, the electric operation apparatuses have difficulty in preventing carbonization of a living tissue and avoiding adhesion of the living tissue to an electrode.

SUMMARY OF THE INVENTION

Accordingly, an object of the present invention is to provide an electric operation apparatus that even when a living tissue has a very large volume, exerts a satisfactory coagulation ability, prevents carbonization of a living tissue, and avoids adhesion of the living tissue to an electrode.

Another object of the present invention is to provide an electric operation apparatus capable of reliably coagulating a living tissue, preventing carbonization of the living tissue, and alleviating adhesion of the living tissue to an electrode.

Still another object of the present invention is to provide an electric operation apparatus that controls high-frequency output power so as to reliably coagulate a living tissue, prevent carbonization of the living tissue, and alleviate adhesion of the living tissue to an electrode.

According to the present invention, there is provided an electric operation apparatus consisting mainly of a high-frequency current generating means, an output changing means, and a control means. The high-frequency current generating means generates high-frequency output power with which high-frequency current is conducted to a living tissue for the purpose of remedying the living tissue. The output changing means changes high-frequency output power generated by the high-frequency current generating means. The control means controls the output changing means so that generation of high-frequency output power will be repeatedly continued and discontinued.

Moreover, according to the present invention, there is provided an electric operation apparatus consisting mainly of a high-frequency current generating means, an output changing means, and a control means. The high-frequency current generating means generates high-frequency output power with which high-frequency current is conducted to a living tissue for the purpose of remedying the living tissue. The output changing means changes high-frequency output power delivered by the high-frequency current generating means. The control means controls the output changing means so that high-frequency output power of a first level and high-frequency output power of a second level different from the first level will be delivered alternately.

Other features and advantages of the present invention will be fully apparent from the description below.

BRIEF DESCRIPTION OF THE DRAWINGS

FIG. 5A is a graph showing a variation with the passage of time of high-frequency output power;

FIG. 5B is a graph showing a change with the passage of time in the temperature of a living tissue which occurs with delivery of the high-frequency output power shown in FIG. 5A;

FIG. 5C is a graph showing a change with the passage of time in the impedance offered by the living tissue which occurs with delivery of the high-frequency output power shown in FIG. 5A;

FIG. 7A is a graph showing a variation with the passage of time of high-frequency output power;

FIG. 7B is a graph showing a change with the passage of time in the impedance offered by a living tissue which occurs with delivery of the high-frequency output power shown in FIG. 7A;

FIG. 8A is a graph showing a variation with the passage of time of high-frequency output power;

FIG. 8B is a graph showing a change with the passage of time in the impedance offered by a living tissue which occurs with delivery of the high-frequency output power shown in FIG. 8A;

FIG. 9A and FIG. 9B are explanatory diagrams concerning an operation to be exerted by a diathermic power supply employed in a second variant;

FIG. 9A is a graph showing a variation with the passage of time of high-frequency output power;

FIG. 9B is a graph showing a change with the passage of time in the impedance offered by a living tissue which occurs with delivery of the high-frequency output power shown in FIG. 9A;

FIG. 10 is a circuit block diagram showing the configuration of the diathermic power supply employed in the first variant;

FIG. 12A is a graph showing a variation with the passage of time of high-frequency output power;

FIG. 12B is a graph showing a change with the passage of time in the temperature of a living tissue which occurs with delivery of the high-frequency output power shown in FIG. 12A;

FIG. 14A to FIG. 14C are first explanatory diagrams concerning an operation to be exerted by the diathermic power supply shown in FIG. 13;

FIG. 14A is a graph showing a variation with the passage of time of high-frequency output power;

FIG. 14B is a graph showing a change with the passage of time in the temperature of a living tissue which occurs with delivery of the high-frequency output power shown in FIG. 14A;

FIG. 14C is a graph showing a variation with the passage of time of high-frequency current conducted with the high-frequency output power shown in FIG. 14A;

FIG. 15A is a graph showing a variation with the passage of time of high-frequency output power;

FIG. 15B is a graph showing a change with the passage of time in the temperature of a living tissue which occurs with delivery of the high-frequency output power shown in FIG. 14A;

FIG. 15C is a graph showing a variation with the passage of time of high-frequency current conducted with the high-frequency output power shown in FIG. 15A;

FIG. 16A is a graph showing a variation with the passage of time of high-frequency output power;

FIG. 16B is a graph showing a variation with the passage of time of high-frequency current conducted with the high-frequency output power shown in FIG. 16A;

FIG. 17A is a graph showing a variation with the passage of time of high-frequency output power;

FIG. 17B is a graph showing a variation with the passage of time of high-frequency current conducted with the high-frequency output power shown in FIG. 17A;

FIG. 18A to FIG. 18C are explanatory diagrams showing the relationships between time and high-frequency output power delivered by a conventional diathermic power supply, between time and the temperature of a living tissue, and between time and the impedance offered by the living tissue;

FIG. 18A is a graph showing a variation with the passage of time of high-frequency output power;

FIG. 18B is a graph showing a change with the passage of time in the temperature of a living tissue which occurs with delivery of the high-frequency output power shown in FIG. 18A;

FIG. 18C is a graph showing a change with the passage of time in the impedance offered by the living tissue which occurs with delivery of the high-frequency output power shown in FIG. 18A;

FIG. 21A is a graph showing a variation with the passage of time of high-frequency output power;

FIG. 21B is a graph showing a change with the passage of time in the temperature of a living tissue which occurs with delivery of the high-frequency output power shown in FIG. 21A;

FIG. 21C is a graph showing a change with the passage of time in the impedance offered by the living tissue which occurs with delivery of the high-frequency output power shown in FIG. 21A;

FIG. 22A is a graph showing a variation with the passage of time of high-frequency output power;

FIG. 22B is a graph showing a change with the passage of time in the temperature of a living tissue which occurs with delivery of the high-frequency output power shown in FIG. 22A;

FIG. 22C is a graph showing a change with the passage of time in the impedance offered by the living tissue which occurs with delivery of the high-frequency output power shown in FIG. 22A;

FIG. 24A is a graph showing a variation with the passage of time of high-frequency output power;

FIG. 24B is a graph showing a change with the passage of time in the impedance offered by a living tissue which occurs with delivery of the high-frequency output power shown in FIG. 24A;

FIG. 26A is a graph showing a variation with the passage of time of high-frequency output power;

FIG. 26B is a graph showing a change with the passage of time in the impedance offered by a living tissue which occurs with delivery of the high-frequency output power shown in FIG. 26A;

FIG. 28A is a graph showing a variation with the passage of time of high-frequency output power;

FIG. 28B is a graph showing a change with the passage of time in the temperature of a living tissue which occurs with delivery of the high-frequency output power shown in FIG. 28A;

FIG. 31A to FIG. 31C are first explanatory diagrams concerning an operation to be exerted by the diathermic power supply shown in FIG. 30;

FIG. 31A is a graph showing a variation with the passage of time of high-frequency output power;

FIG. 31B is a graph showing a change with the passage of time in the temperature of a living tissue which occurs with delivery of the high-frequency output power shown in FIG. 31A;

FIG. 31C is a graph showing a variation with the passage of time of high-frequency current conducted with the high-frequency output power shown in FIG. 31A;

FIG. 32A to FIG. 32C are second explanatory diagrams concerning an operation to be exerted by the diathermic power supply shown in FIG. 30;

FIG. 32A is a graph showing a variation with the passage of time of high-frequency output power;

FIG. 32B is a graph showing a change with the passage of time in the temperature of a living tissue which occurs with delivery of the high-frequency output power shown in FIG. 32A;

FIG. 32C is a graph showing a variation with the passage of time of high-frequency current conducted with the high-frequency output power shown in FIG. 32A;

FIG. 33A is a graph showing a variation with the passage of time of high-frequency output power;

FIG. 33B is a graph showing a variation with the passage of time of high-frequency current conducted with the high-frequency output power shown in FIG. 33A;

FIG. 36A is a graph showing a variation with the passage of time of high-frequency output power;

FIG. 36B is a graph showing a change with the passage of time in the temperature of a living tissue which occurs with delivery of the high-frequency output power shown in FIG. 36A;

FIG. 36C is a graph showing a change with the passage of time in the impedance offered by the living tissue which occurs with delivery of the high-frequency output power shown in FIG. 36A;

FIG. 37A is a graph showing a variation with the passage of time of high-frequency output power;

FIG. 37B is a graph showing a change with the passage of time in the temperature of a living tissue which occurs with delivery of the high-frequency output power shown in FIG. 37A;

FIG. 37C is a graph showing a change with the passage of time in the impedance offered by the living tissue which occurs with delivery of the high-frequency output power shown in FIG. 37A;

FIG. 39A is a graph showing a variation with the passage of time of high-frequency output power;

FIG. 39B is a graph showing a change with the passage of time in the impedance offered by a living tissue which occurs with delivery of the high-frequency output power shown in FIG. 39A;

FIG. 40A is a graph showing a variation with the passage of time of high-frequency output power;

FIG. 40B is a graph showing a change with the passage of time in the impedance offered by a living tissue which occurs with delivery of the high-frequency output power shown in FIG. 40A;

FIG. 41A and FIG. 41B are explanatory diagrams concerning a third operation to be exerted by the diathermic power supply that flows according to the control sequence described in the flowchart of FIG. 38;

FIG. 41A is a graph showing a variation with the passage of time of high-frequency output power;

FIG. 41B is a graph showing a change with the passage of time in the impedance offered by a living tissue which occurs with delivery of the high-frequency output power shown in FIG. 41A;

FIG. 42A is a graph showing a variation with the Passage of time of high-frequency output power;

FIG. 42B is a graph showing a change with the passage of time in the impedance offered by a living tissue which occurs with delivery of the high-frequency output power shown in FIG. 42A;

FIG. 43 is a circuit block diagram showing a diathermic power supply employed in a first variant;

FIG. 45A is a graph showing a variation with the passage of time of high-frequency output power;

FIG. 45B is a graph showing a change with the passage of time in the temperature of a living tissue which occurs with delivery of the high-frequency output power shown in FIG. 45A;

FIG. 46 is a circuit block diagram showing the configuration of a diathermic power supply unit in accordance with a sixth embodiment of the present invention;

FIG. 47A to FIG. 47C are first explanatory diagrams concerning an operation to be exerted by the diathermic power supply shown in FIG. 46;

FIG. 47A is a graph showing a variation with the passage of time of high-frequency output power;

FIG. 47B is a graph showing a change with the passage of time in the temperature of a living tissue which occurs with delivery of the high-frequency output power shown in FIG. 47A;

FIG. 47C is a graph showing a variation with the passage of time of high-frequency current conducted with the high-frequency output power shown in FIG. 47A;

FIG. 48A to FIG. 48C are second explanatory diagrams concerning an operation to be exerted by the diathermic power supply shown in FIG. 46;

FIG. 48A is a graph showing a variation with the passage of time of high-frequency output power;

FIG. 48B is a graph showing a change with the passage of time in the temperature of a living tissue which occurs with delivery of the high-frequency output power shown in FIG. 48A;

FIG. 48C is a graph showing a variation with the passage of time of high-frequency current conducted with the high-frequency output power shown in FIG. 48A;

FIG. 49A is a graph showing a variation with the passage of time of high-frequency output power;

FIG. 49B is a graph showing a variation with the passage of time of high-frequency current conducted with the high-frequency output power shown in FIG. 49A;

FIG. 50A and FIG. 50B are fourth explanatory diagrams concerning an operation to be exerted by the diathermic power supply unit shown in FIG. 46;

FIG. 50A is a graph showing a variation with the passage of time of high-frequency output power;

FIG. 50B is a graph showing a variation with the passage of time of high-frequency current conducted with the high-frequency output power shown in FIG. 50A;

FIG. 51A and FIG. 51B are fifth explanatory diagrams concerning an operation to be exerted by the diathermic power supply shown in FIG. 46;

FIG. 51A is a graph showing a variation with the passage of time of high-frequency output power;

FIG. 51B is a graph showing a variation with the passage of time of high-frequency current conducted with the high-frequency output power shown in FIG. 51A;

FIG. 52A and FIG. 52B are sixth explanatory diagrams concerning an operation to be exerted by the diathermic power supply shown in FIG. 46;

FIG. 52A is a graph showing a variation with the passage of time of high-frequency output power; and FIG. 52B is a graph showing a variation with the passage of time of high-frequency current conducted with the high-frequency output power shown in FIG. 52A.

DESCRIPTION OF THE PREFERRED EMBODIMENTS

Figure 1:
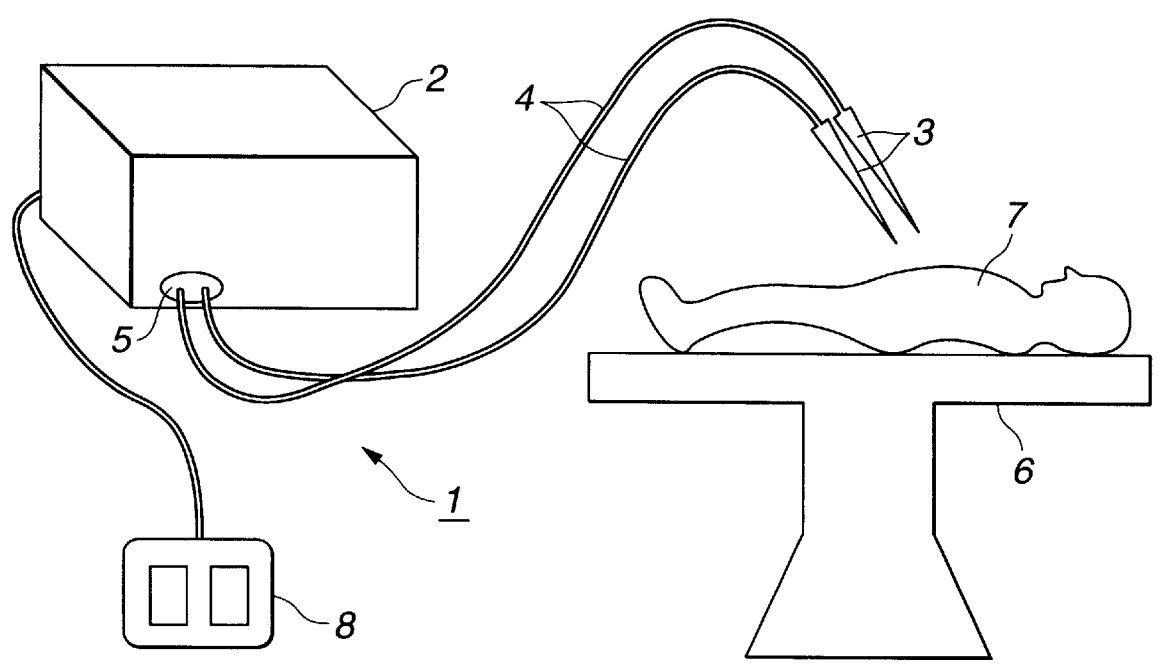
FIG. 1 shows the overall configuration of an electric operation apparatus in accordance with a first embodiment of the present invention.

Referring to the drawings, embodiments of the present invention will be described below.

Figure 2:
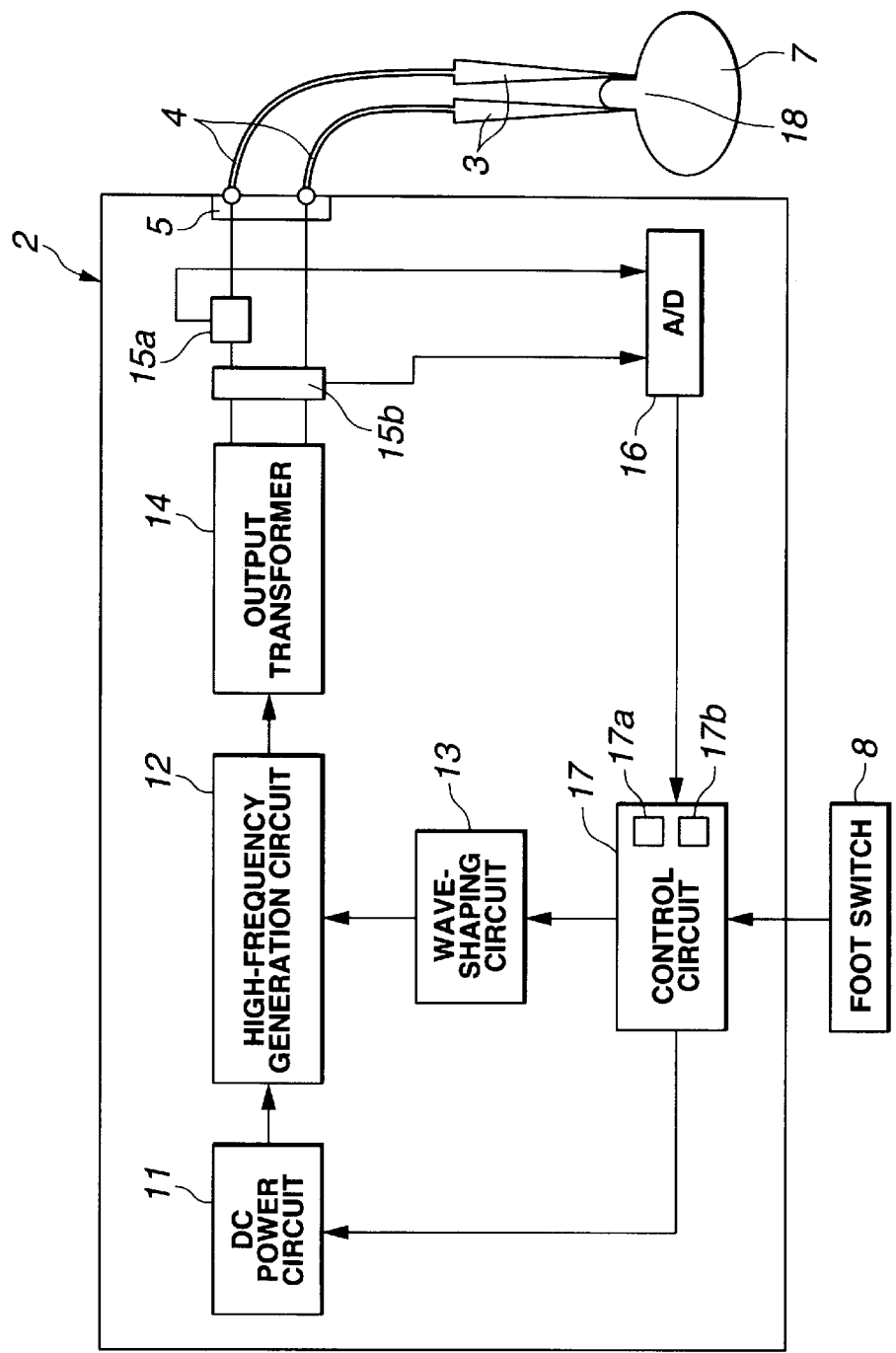
FIG. 2 is a circuit block diagram showing the circuitry of a diathermic power supply shown in FIG. 1.
Figure 3:
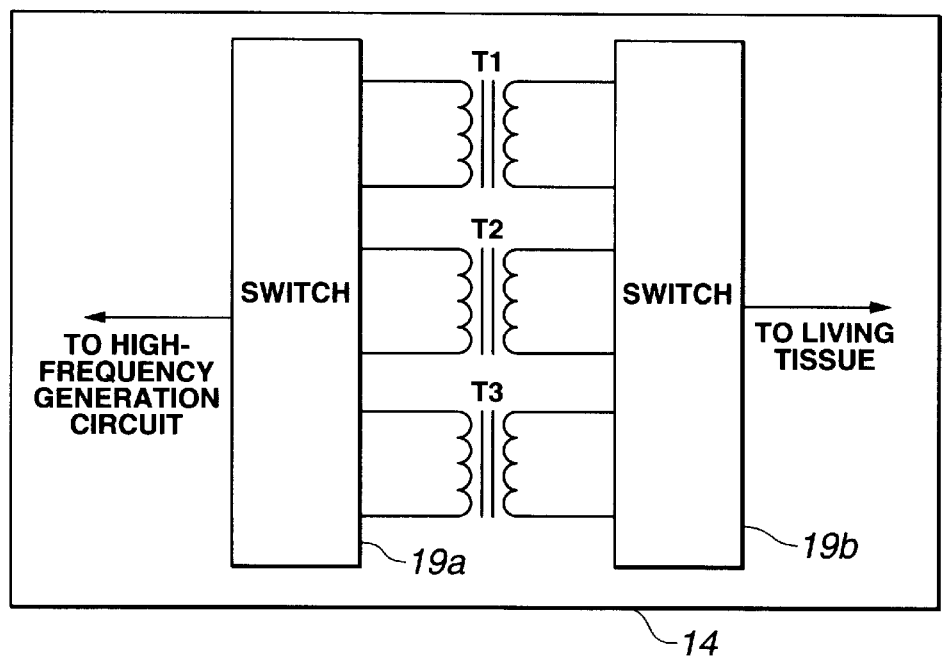
FIG. 3 is a circuit block diagram showing the configuration of an output transformer.
Figure 4:
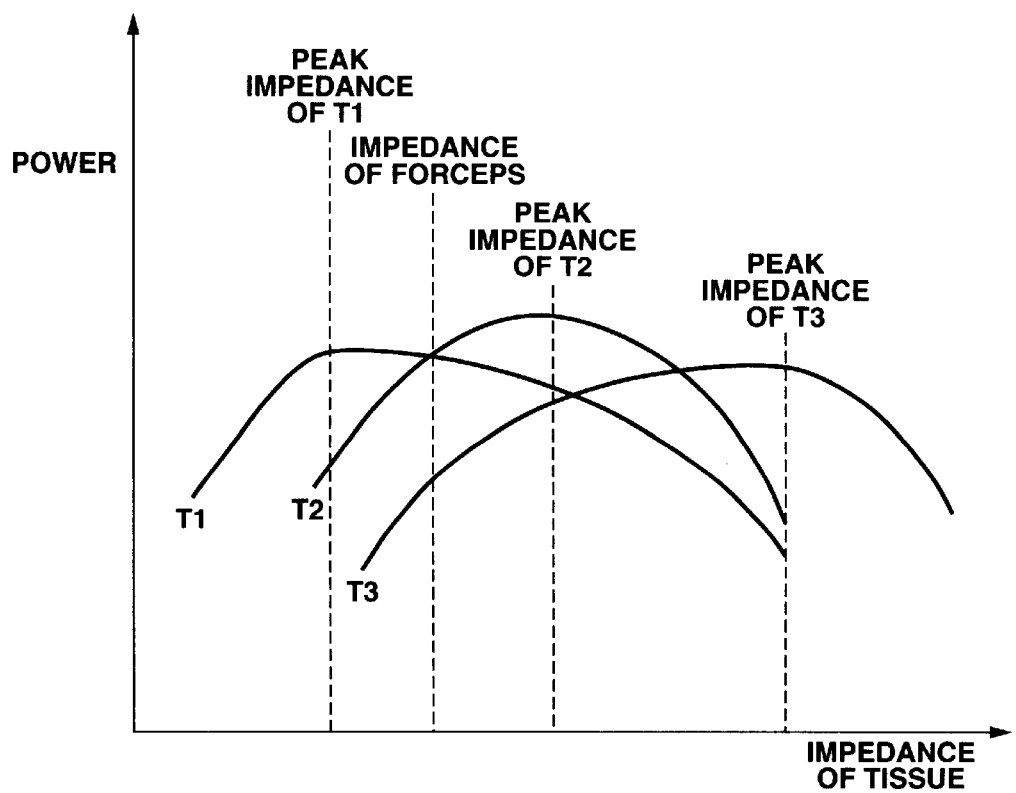
FIG. 4 is a graph showing the characteristics of transformers that constitute the output transformer shown in FIG. 3.
Figure 5:
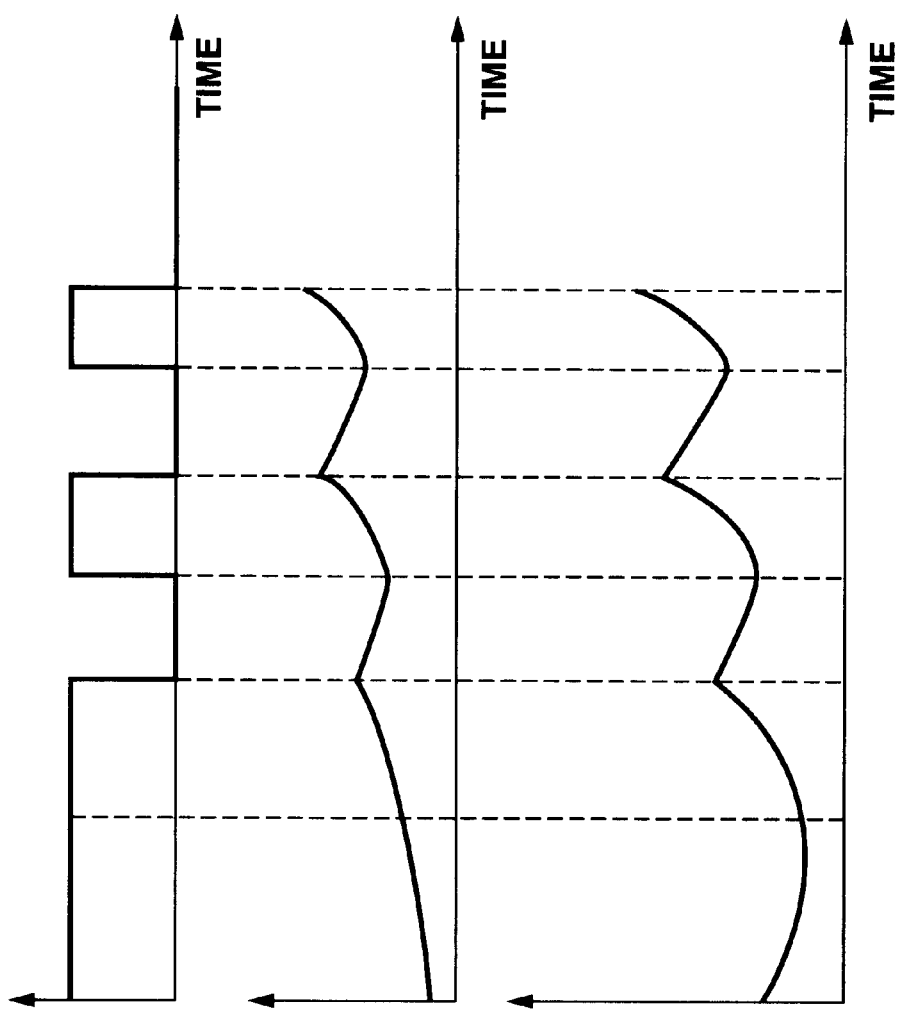
FIG. 5A to FIG. 5C are explanatory diagrams showing the waveshape of high-frequency output power whose delivery is repeatedly continued and discontinued, and changes in the temperature and impedance offered and exhibited by a living tissue.
Figure 6:
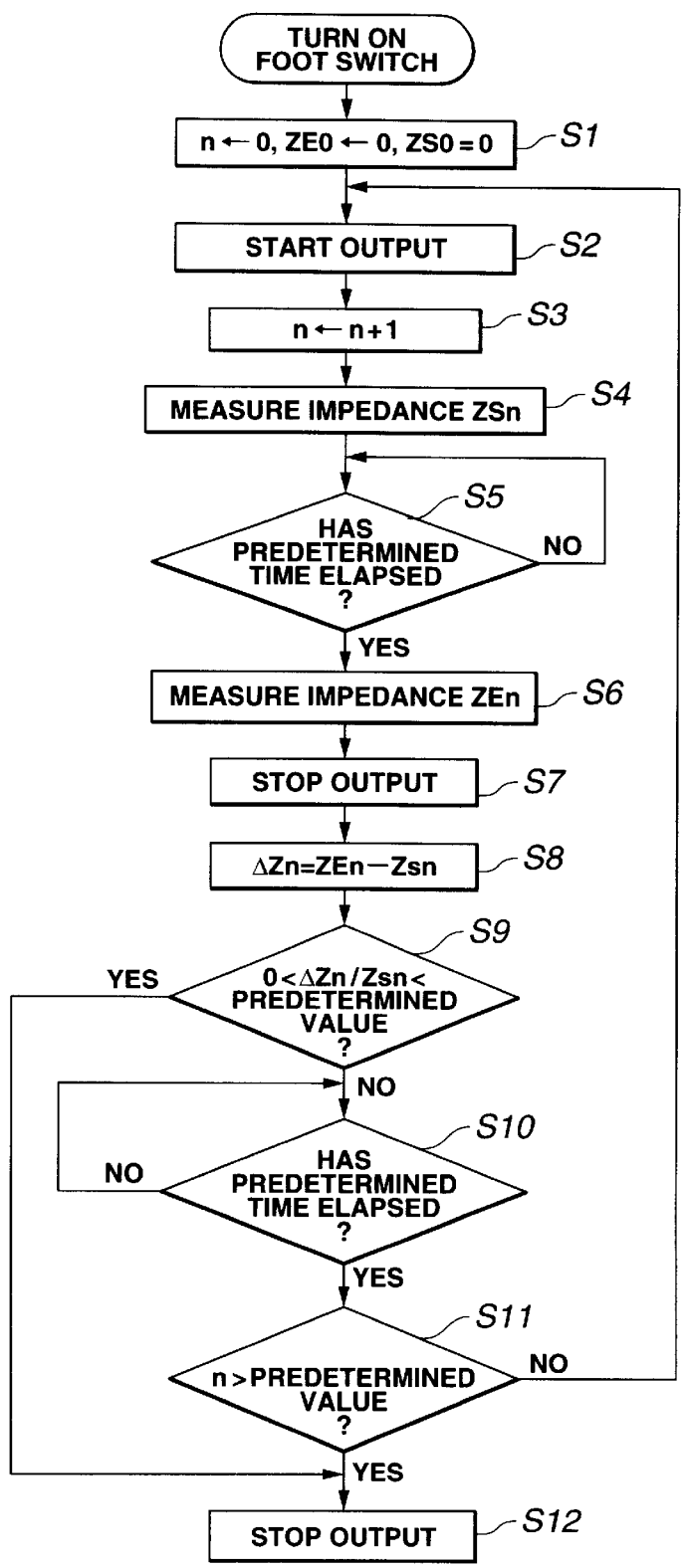
FIG. 6 is a flowchart describing a control sequence followed by a control circuit employed in the embodiment.
Figures 7A, 7B:
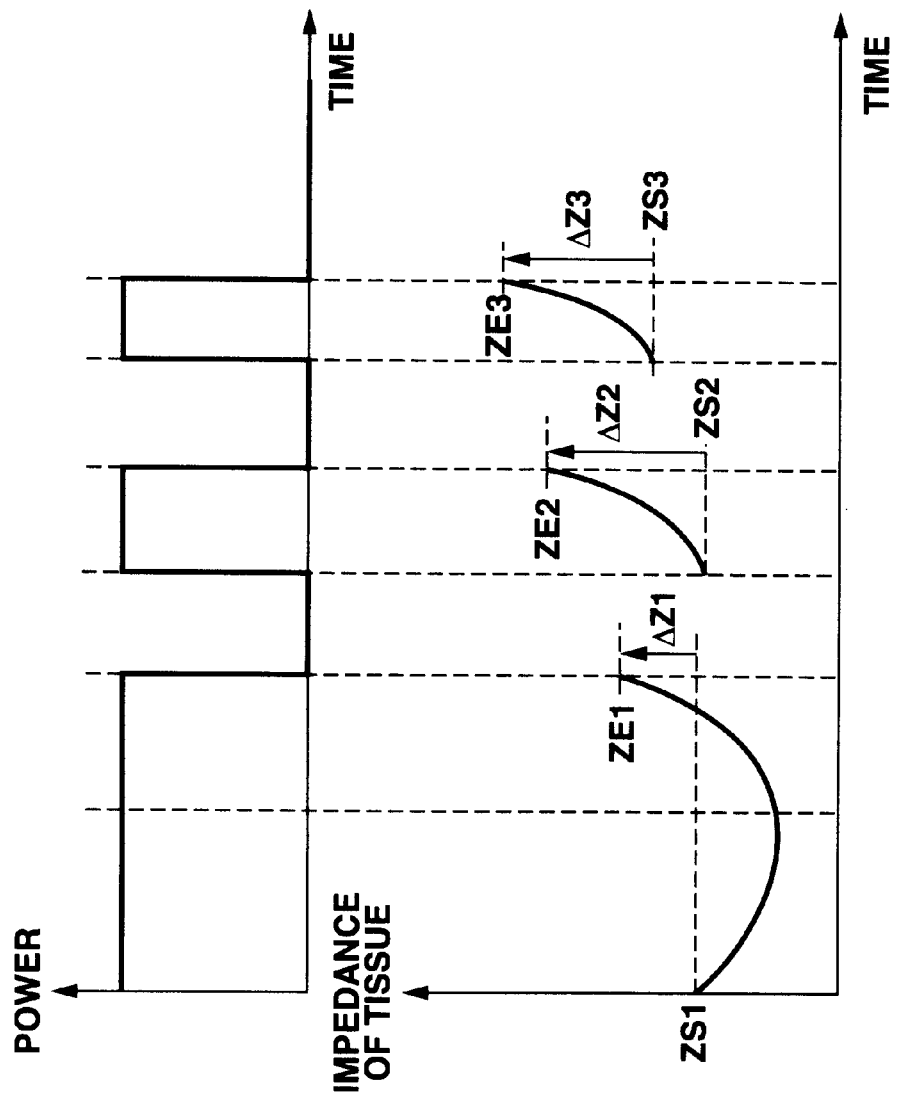
FIG. 7A and FIG. 7B are explanatory diagrams concerning an operation to be exerted by the diathermic power supply that follows the control sequence described in the flowchart of FIG. 6.
Figures 8A, 8B:
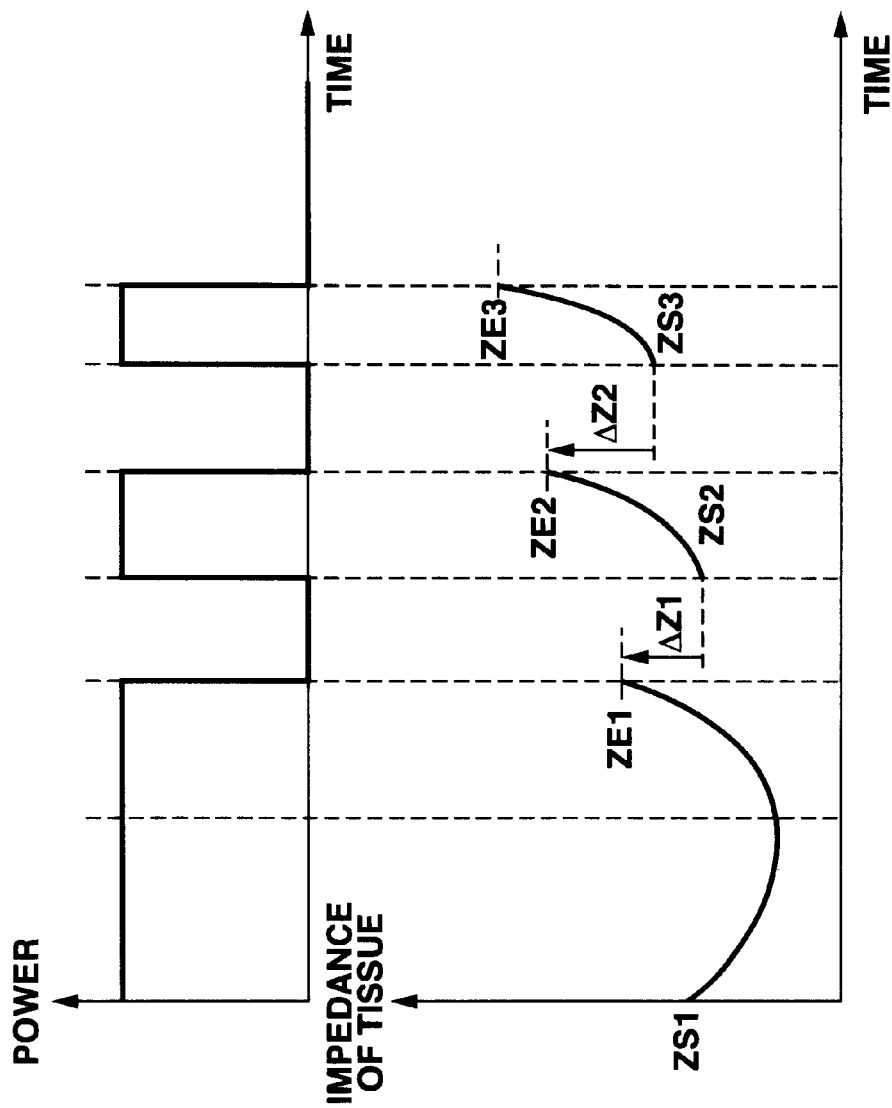
FIG. 8A and FIG. 8B are explanatory diagrams concerning an operation to be exerted by a diathermic power supply employed in a first variant.
Figure 11:
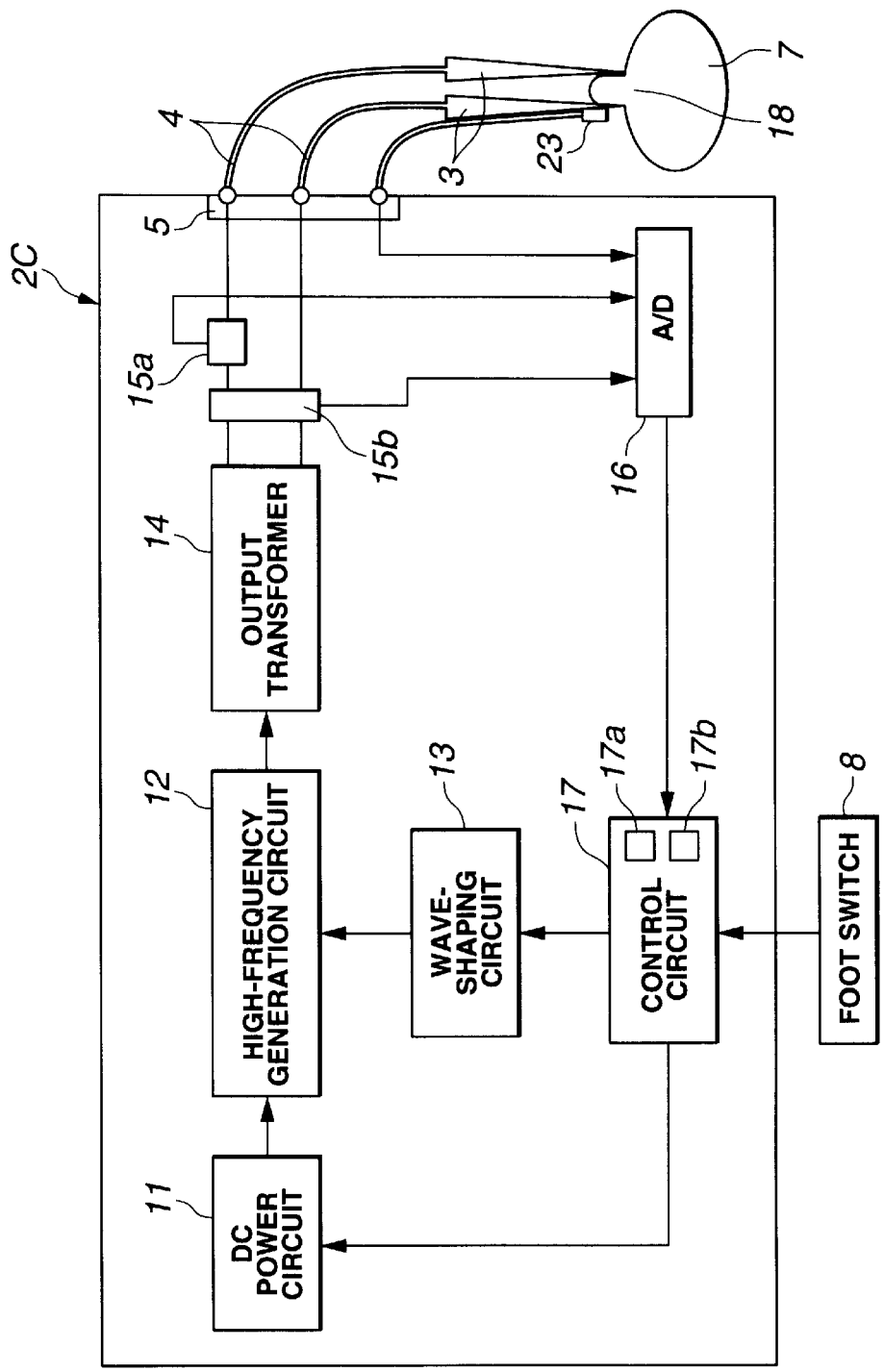
FIG. 11 is a circuit block diagram showing the configuration of the diathermic power supply employed in the second variant.
Figures 12A, 12B:
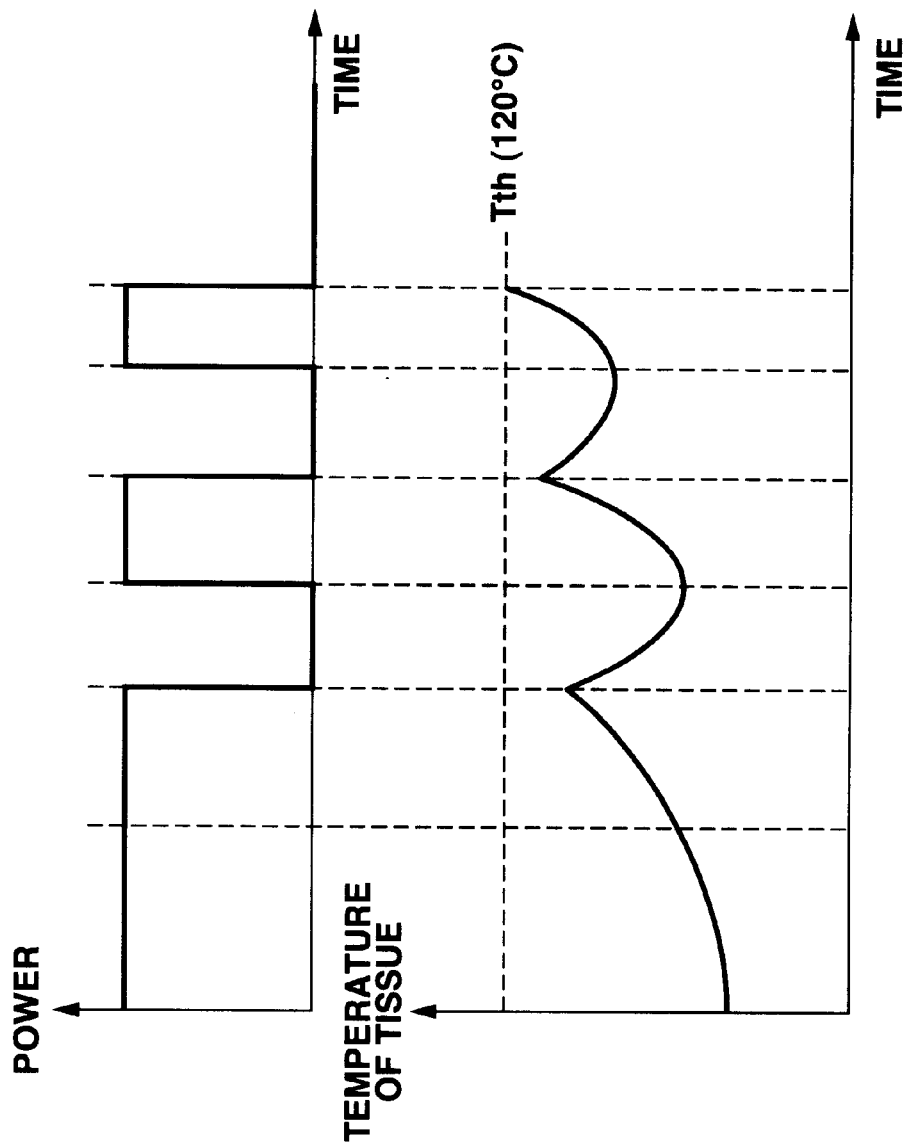
FIG. 12A and FIG. 12B are explanatory diagrams showing an operation to be exerted by a diathermic power supply employed in a third variant.

FIG. 1 to FIG. 12C are concerned with a first embodiment of the present invention. FIG. 1 shows the overall configuration of an electric operation apparatus in accordance with a first embodiment of the present invention. FIG. 2 is a circuit block diagram showing the circuitry of a diathermic power supply shown in FIG. 1. FIG. 3 is a circuit block diagram showing the configuration of an output transformer. FIG. 4 is a graph showing the characteristics of transformers that constitute the output transformer. FIG. 5A to FIG. 5C are explanatory diagrams showing the waveshape of high-frequency output power whose delivery is repeatedly continued and discontinued, and changes in the temperature and impedance exhibited and offered by a living tissue. FIG. 5A is a graph showing a variation with the passage of time of high-frequency output power. FIG. 5B is a graph showing a change with the passage of time in the temperature of a living tissue which occurs with delivery of the high-frequency output power shown in FIG. 5A. FIG. 5C is a graph showing a change with the passage of time in the impedance offered by the living tissue which occurs with delivery of the high-frequency output power shown in FIG. 5A. FIG. 6 is a flowchart describing a control sequence according to a control circuit employed in the present embodiment. FIG. 7A and FIG. 7B are explanatory diagrams concerning an operation to be exerted by a diathermic power supply that flows according to the control sequence described in the flowchart of FIG. 6. FIG. 7A is a graph showing a variation with the passage of time of high-frequency output power. FIG. 7B is a graph showing a change with the passage of time in the impedance offered by a tissue which occurs with delivery of the high-frequency output power shown in FIG. 7A. FIG. 8A and FIG. 8B are explanatory diagrams concerning an operation to be exerted by a diathermic power supply employed in a first variant. FIG. 8A is a graph showing a variation with the passage of time of high-frequency output power. FIG. 8B is a graph showing a change with the passage of time in the impedance offered by a tissue which occurs with delivery of the high-frequency output power shown in FIG. 8A. FIG. 9A and FIG. 9B are explanatory diagrams concerning an operation to be exerted by a diathermic power supply unit employed in a second variant. FIG. 9A is a graph showing a variation with the passage of time of high-frequency output power. FIG. 9B is a graph showing a change with the passage of time in the impedance offered by a living tissue which occurs with delivery of the high-frequency output power shown in FIG. 9A. FIG. 10 is a circuit block diagram showing the configuration of the diathermic power supply unit employed in the first variant. FIG. 11 is a circuit block diagram showing the configuration of the diathermic power supply unit employed in the second variant. FIG. 12A and FIG. 12B are explanatory diagrams concerning an operation to be exerted by the diathermic power supply unit employed in a third variant. FIG. 12A is a graph showing a variation with the passage of time of high-frequency output power. FIG. 12B is a graph showing a change with the passage of time in the temperature of a living tissue which occurs with delivery of the high-frequency output power shown in FIG. 12A.

As shown in FIG. 1, an electric operation apparatus 1 in accordance with the present invention has a diathermic power supply unit 2 that delivers high-frequency diathermic output power. Connection cables 4 having a pair of electrodes 3, which serves as a therapeutic accessory (operating instrument), fixed to the distal ends thereof are joined to a connector 5 formed in the diathermic power supply unit 2. The electric operation apparatus 1 delivers high-frequency diathermic output power to a patient 7 by way of the electrodes 3. The patient 7 lies down on a patient couch 6. The electric operation apparatus 1 thus performs a cure or a remedy (an operation) on the patient.

Moreover, for example, a footswitch 8 to be stepped on in order to switch delivery and non-delivery of high-frequency output power for use in diathermy is connected to the diathermic power supply unit 2. The electrodes 3 may be either single-pole electrodes or multi-pole electrodes.

The diathermic power supply unit 2 is, as shown in FIG. 2, plugged in to a mains power supply (not shown). The diathermic power supply unit 2 consists mainly of a direct current (dc) power circuit 11, a high-frequency generation circuit 12, a wave-shaping circuit 13, an output transformer 14, a current sensor 15a, a voltage sensor 15b, an A/D converter 16, and a control circuit 17. The dc power circuit 11 converts mains power into dc power and supplies the dc power. The high-frequency generation circuit 12 is driven with the dc power supplied from the dc power circuit 1, oscillates at a high frequency, and generates high-frequency output power (high-frequency current) used for remedy. The wave-shaping circuit 13 instructs the high-frequency generation circuit 12 in a waveshape for high-frequency output power. The output transformer 14 transfers high-frequency output power generated by the high-frequency generation circuit 2 to the electrodes 3. The current sensor 15a detects current that flows through the output transformer 14. The voltage sensor 15b detects voltage that is induced by the output transformer 14. The A/D converter 16 digitizes a current value and a voltage value produced by the current sensor 15a and voltage sensor 15b. The control circuit 17 switches supply and non-supply of power to the dc power circuit 11 according to the digitized current data sent from the A/D converter 16, and instructs the wave-shaping circuit 13 to present a different waveshape.

The control circuit 17 includes a timer 17a that indicates passage of time since start of delivering high-frequency output power to a living tissue, and a counter 17b that counts the number of times of delivery by which high-frequency output power is delivered.

The diathermic power supply unit 2 has the connection cables 4 joined to the connector 5 thereof, whereby a high-frequency diathermy is performed on a living tissue 18 of the patient 7 using the electrodes 3.

The output transformer 14 has the configuration shown in FIG. 3. As seen from FIG. 3, the output transformer 14 consists of three transformers T1, T2, and T3 that can transfer maximum output power and offer different values of impedance. Moreover, the output transformer 14 includes switches 19a and 19b that are interlocked with each other. The switches 19a and 19b switch primary windings of the transformers T1 to T3 and secondary windings thereof respectively so that one of the primary windings of the three transformers will be connected to the high-frequency generation circuit and one of the secondary windings thereof will be connected to a living tissue.

FIG. 4 shows the characteristics of the three transformers T1, T2, and T3 that can transfer maximum output power and offer different values of impedance.

Referring to FIG. 4, the impedances offered by the transformers T1, T2, and T3 capable of transferring maximum output power are of the smallest level, the second smallest level, and the largest level.

A transformer to be selected from among the transformers constituting the output transformer 14 is a transformer capable of transferring maximum output power while offering impedance that is smaller than the impedance offered by the living tissue 18 of the patient 7 clamped by the electrodes 3.

In other words, the output transformer 14 selects any of the transformers thereof so that the selected transformer will offer impedance that is smaller than the impedance offered by the living tissue while transferring maximum output power. The two switches 19a and 19b included in the output transformer 14 are controlled by the control circuit 17 so that output power generated by the high-frequency generation circuit 12 will be delivered to the living tissue 18 via the selected transformer.

The impedance shown in FIG. 4 to be offered by forceps is initial impedance offered when the forceps (therapeutic accessory) are used to clamp a living tissue. When the living tissue is coagulated with high-frequency current, the impedance offered by the forceps increases. When the transformers offer the impedances shown in FIG. 4, the transformer T1 is selected because the impedance the transformer T1 offers is smaller than the impedance the forceps offer.

According to the present embodiment, the control circuit 17 extends control so that (high-frequency) output power will be intermittently delivered to a living tissue as shown in FIG. 5A to FIG. 5C.

In general, when high-frequency output power is delivered to a living tissue, the living tissue is heated and denatured. Thereafter, the living tissue has water thereof depleted and thus gets dried up. The living tissue is coagulated in due course. Although the living tissue gets dried up, if high-frequency output power is kept delivered to the living tissue, the living tissue is carbonized to adhere to the electrodes 3. In order to prevent adhesion of the living tissue to the electrodes 3, delivery of high-frequency output power must be stopped as soon as the living tissue gets dried.

If high-frequency output power of a constant level shown in FIG. 18A is delivered to a living tissue irrespective of how much time has elapsed, the living tissue is heated. The temperature of the living tissue gradually rises, as shown in FIG. 18B, along with progress in denaturation and drying of the living tissue. On the other hand, the impedance offered by the living tissue decreases in an early stage as shown in FIG. 18C, remains constant for some time, and then abruptly rises with the dry of the living tissue. Conventionally, as soon as it is judged from the impedance or temperature offered or exhibited by the living tissue that the living tissue gets dried up, delivery of high-frequency output power is stopped.

According to the present embodiment, high-frequency output power is, as shown in FIG. 5A, delivered intermittently. As shown in FIG. 5B, the impedance offered by the living tissue increases and then decreases with discontinuation of delivery of high-frequency output power. As shown in FIG. 5C, the temperature exhibited by the living tissue rises and then drops with discontinuation of delivery of high-frequency output power. When high-frequency output power is delivered again, the impedance of the living tissue increases again, and the temperature thereof rises again. This procedure is repeated, whereby the living tissue is held denatured and dried. Thus, carbonization of the living tissue or adhesion thereof to the electrodes 3 that is derived from a rise in the temperature of the living tissue (occurring when high-frequency output power is delivered continuously) can be prevented, and a large amount of high-frequency current can be conducted. Consequently, according to the present embodiment, compared with the aforesaid conventional method, a living tissue can be coagulated over a wide range.

As mentioned above, high-frequency output power is delivered intermittently and a living tissue is coagulated over a wide range. The impedance offered by the living tissue during each delivery period gets larger than the impedance offered thereby during an immediately preceding delivery period. Likewise, the temperature exhibited by the living tissue during each delivery period gets higher than the temperature exhibited during an immediately preceding delivery period. Rates at which the impedance of the living tissue increases during each delivery period and the temperature rises during the same period get higher than the ones at which the impedance increases during the immediately preceding delivery period and the temperature rises during the same period. Rates at which the impedance of the living tissue decreases during each pause period and the temperature thereof drops during the same period also get higher. Owing to the nature of living tissues, the control circuit 17 can judge over how wide a range a living tissue is coagulated.

An operation to be exerted by the present embodiment that utilizes the above nature of living tissues will be described below. When the footswitch 8 is stepped on, the control circuit 17 incorporated in the diathermic power supply unit 2 starts extending control according to a control sequence described in the flowchart of FIG. 6.

When the footswitch 8 is stepped on, the control circuit 17 resets the number of times of delivery by which high-frequency output power is delivered (diathermy is performed) n and the impedances ZE0 and ZS0, which are offered by a living tissue during delivery of high-frequency output power, to 0s.

Thereafter, the control circuit 17 starts delivering high-frequency output power at step S2. At step S3, the number of times of diathermy n is incremented by one (n becomes equal to 1).

The control circuit 17 receives signals from the current sensor 15a and voltage sensor 15b via the A/D converter 16 at step S4. The control circuit 17 uses the received signals to calculate the impedance ZSn (where n equals 1) offered immediately after the start of the n-th delivery period. Specifically, the control circuit 17 divides a voltage value represented by the signal received from the voltage sensor 15b by a current value represented by the signal received from the current sensor 15a so as to calculate the impedance ZS1. Then, the control circuit 17 stores the value of the impedance ZS1 in a memory.

Thereafter, the control circuit 17 judges at step S5 whether delivery of high-frequency output power has been repeated by a predetermined time instant, and waits until predetermined time elapses.

When the predetermined time has elapsed, the control circuit 17 uses the output signals of the current sensor 15a and voltage sensor 15b to calculate at step S6 the impedance ZEn (herein, ZE1), which is offered immediately before the n-th pause period during which high-frequency output power is not delivered, in the same manner as it calculates the impedance ZSn at step S4. The control circuit 17 stores the calculated impedance value in the memory, and stops delivery of high-frequency output power at step S7.

The control circuit 17 stores a difference between ZEn and ZSn (ZEn−ZSn, or herein, ZE1−ZS1) as a difference $\Delta Zn$ (where n equals 1). FIG. 7A and FIG. 7B show a variation of high-frequency output power, a change in the impedance offered by a living tissue, and the difference $\Delta Z1$.

The control circuit 17 judges at step S9 whether $\Delta Z1/ZS1$ is smaller than a predetermined value (value implying completion of coagulation) and is a negative value. If $\Delta Z1/ZS1$ meets the conditions, the control circuit 17 stops repetition of continuation and discontinuation of delivery at step S12 so as to thus terminate a remedy. Thus, when a desired range of a living tissue is coagulated, the control circuit 17 successfully stops delivery of high-frequency output power.

Moreover, if it is found at step S9 that $\Delta Z1/ZS1$ does not meet the conditions, the control circuit 17 judges at step S10 whether a pause period during which output power is not delivered has consumed predetermined time. Furthermore, the control circuit 17 judges at step S11 whether the number of times of delivery n is larger than a predetermined value. If the number of times of delivery n is larger than the predetermined value, the control circuit 17 stops repetition of continuation and discontinuation of delivery at step S11. Consequently, if the control circuit 17 fails to accurately calculate the impedance ZEn using the output signals of the current sensor 15a and voltage sensor 15b, the control circuit 17 can discontinue delivery of high-frequency output power. If the number of times of delivery n has not reached the predetermined value, the control circuit 17 passes control back to step S2. The aforesaid steps are then repeated.

An upper limit of the delivery period treated at step S5, an upper limit of the pause period treated at step S10, and an upper limit of the number of times of delivery n treated at step S11 may be determined based on a desired coagulated state by a user. Otherwise, the upper limits may be varied depending on the impedance and temperature of a living tissue.

In the flowchart of FIG. 6, $\Delta Zn$ is defined as $ZEn-ZSn$. The impedances ZS and ZE are calculated during each delivery period of high-frequency output power. The difference $\Delta Z$ is calculated as indicated in FIG. 7B.

However, as shown in FIG. 8B, the control circuit 17 may define $\Delta Zn$ ($\Delta Z$) as $ZEn-ZSn+1$. In this case, the control circuit 17 calculates the impedance ZEn offered during the pause period during which high-frequency output power is not delivered, and calculates $ZSn+1$ using the impedance $ZSn$ offered at the start of a delivery period succeeding the pause period. If the difference between ZEn and $ZSn+1$, $\Delta Z = ZEn - ZSn+1$, or a quotient calculated by dividing the difference $\Delta Z$ by the length of the delivery period gets larger than a predetermined value, the control circuit 17 may judge whether repetition of continuation and discontinuation of delivery shown in FIG. 8A should be terminated.

Moreover, as shown in FIG. 9B, when the impedance offered by a living tissue has reached a predetermined value Zth that is, for example, 1 k$\Omega$, the control circuit 17 may terminate repetition of continuation and discontinuation of delivery of high-frequency output power as shown in FIG. 9A.

Moreover, the control circuit 17 may use a minimum value Zmin and a maximum value Zmax of the impedance instead of ZS and define as $\Delta Z = Zmax - Zmin$, though these values are not shown.

The diathermic power supply may be configured as a diathermic power supply unit 2B shown in FIG. 10.

The diathermic power supply unit 2B shown in FIG. 10 has, in addition to the same components as the diathermic power supply unit 2 shown in FIG. 2, a dc power circuit 21 and a sensing high-frequency generation circuit 22. Operating power is supplied from the dc power circuit 21 to the sensing high-frequency generation circuit 22. The diathermic power supply unit 2B transfers sensing high-frequency output power generated by the sensing high-frequency generation circuit 22 to the output transformer 14. The impedance offered by a living tissue is then measured. This results in a more accurate control sequence.

In this case, preferably, the control circuit 17 should calculate the impedance offered by a living tissue while delivery of high-frequency output power for use in a remedy is discontinued. This is because when the impedance is calculated with delivery of high-frequency output power discontinued, influence of noises can be alleviated. For this reason, the control circuit 17 may control switching of supply and non-supply of dc power from the dc power circuit 11 or 21.

Moreover, the diathermic power supply may be configured like a diathermic power supply 2C shown in FIG. 11.

The diathermic power supply 2C shown in FIG. 11 has the same components as those of the diathermic power supply unit 2 shown in FIG. 2. However, the temperature sensor 23 is fixed to, for example, the electrode 3. In this case, when the temperature of a living tissue detected by the temperature sensor 23 has reached, as shown in FIG. 12B, a predetermined value Tth that is, for example, 120°, the control circuit 17 terminates repetition of continuation and discontinuation of delivery shown in FIG. 12A.

In the electric operation apparatus 1 of the present embodiment, the number of times of delivery or repetition n treated at step S11 described in FIG. 6 has an upper limit. Alternatively, the number of times of delivery may also have a lower limit.

In the electric operation apparatus 1 of the present embodiment, the control circuit 17 may judge the coagulated state of a living tissue from the quotient of $\Delta Z/ZS$. The result of the judgment may be presented on a display panel and a monitor that are not shown.

The present embodiment has an advantage described below.

Namely, according to the present embodiment, delivery of output power with which high-frequency current is conducted is repeatedly continued and discontinued. Consequently, high-frequency current can be repeatedly conducted to a living tissue with the temperature of the living tissue held within a range of temperature values that does not bring about carbonization. The living tissue is therefore reliably coagulated. Nevertheless, carbonization of the living tissue and adhesion thereof to the electrodes can be prevented.

Figure 13:
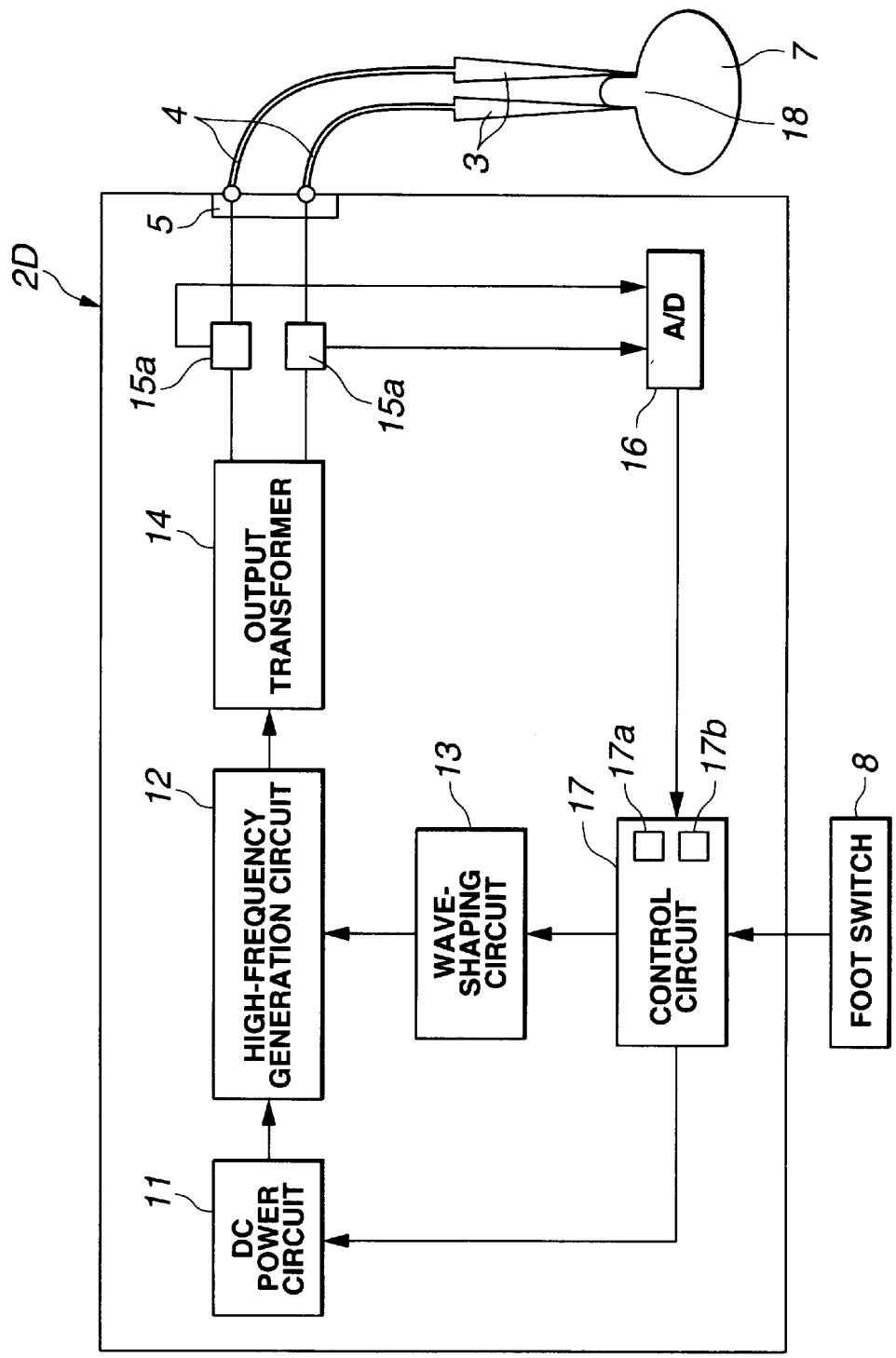
FIG. 13 is a circuit block diagram showing the configulation of a diathermic power supply employed in a second embodiment of the present invention.
Figures 15A, 15B, 15C:
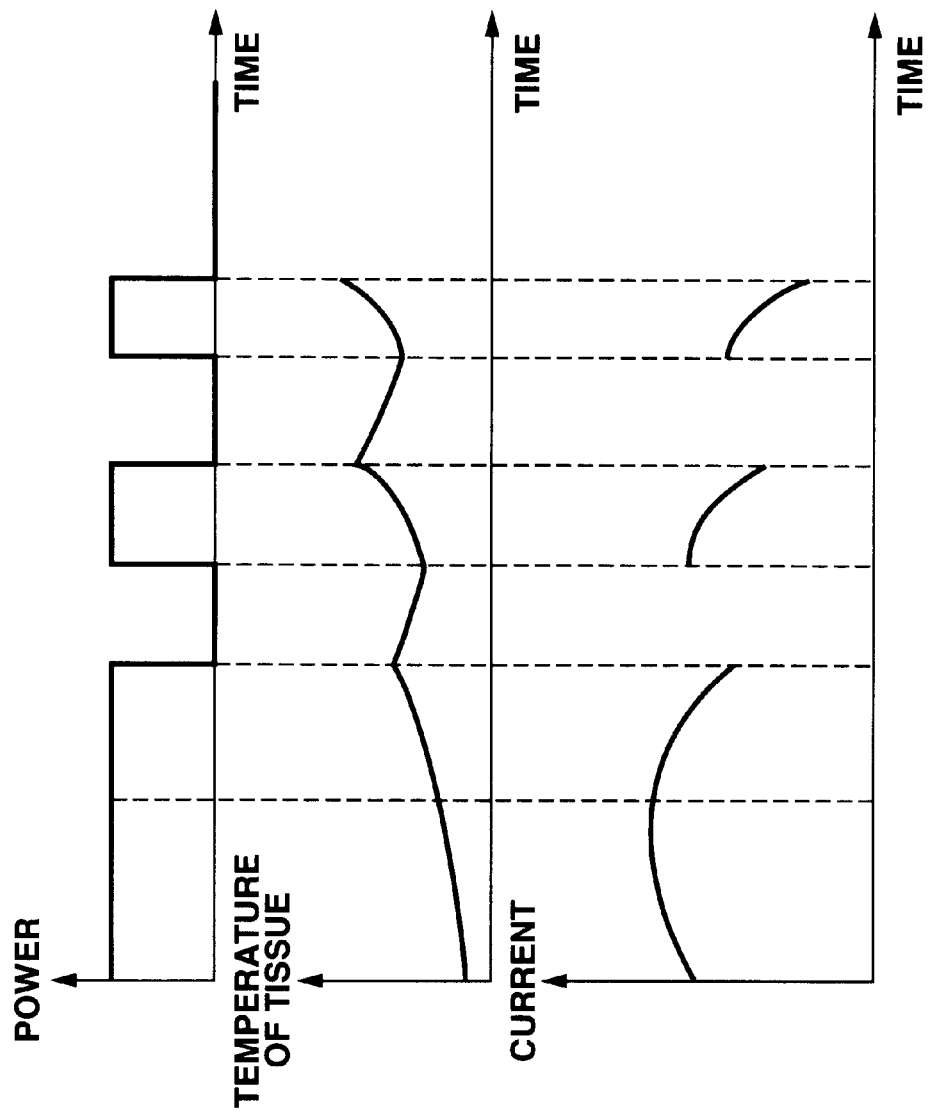
FIG. 15A to FIG. 15C are second explanatory diagrams concerning an operation to be exerted by the diathermic power supply shown in FIG. 13.
Figures 16A, 16B:
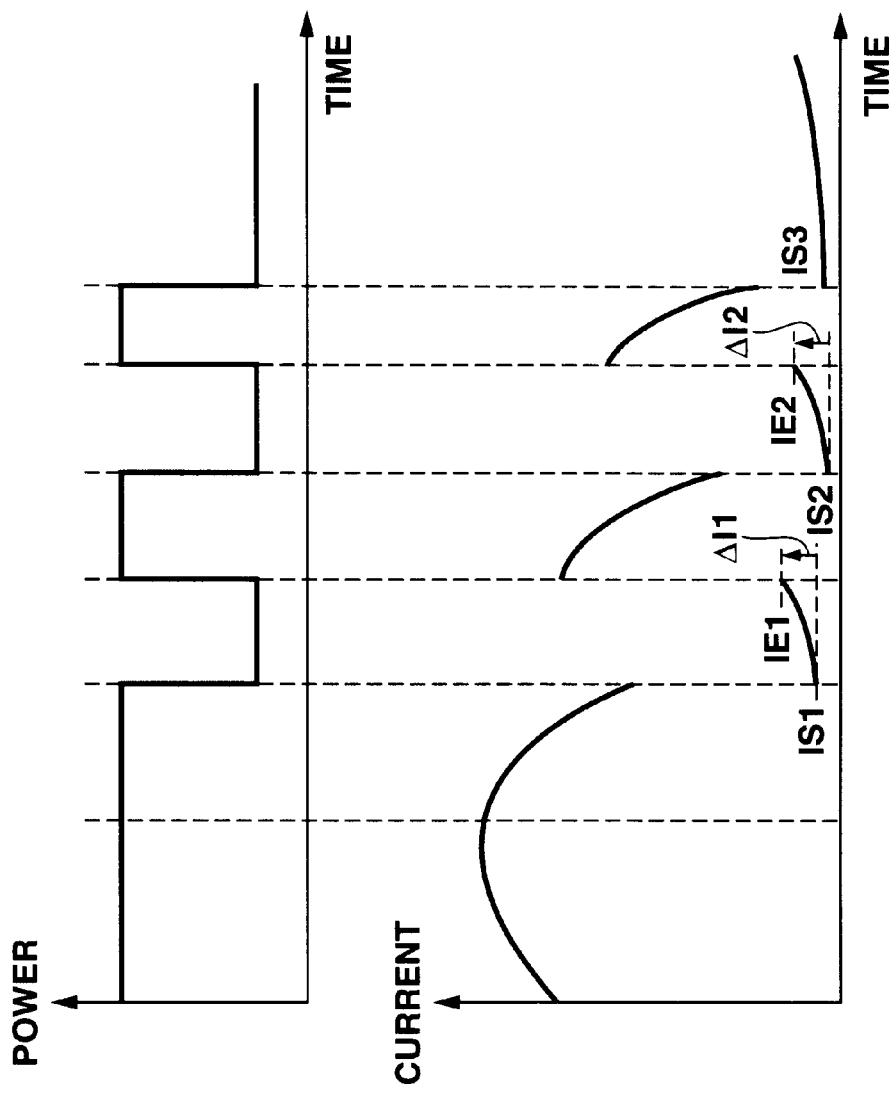
FIG. 16A and FIG. 16B are third explanatory diagrams concerning an operation to be exerted by the diathermic power supply shown in FIG. 13.
Figures 17A, 17B:
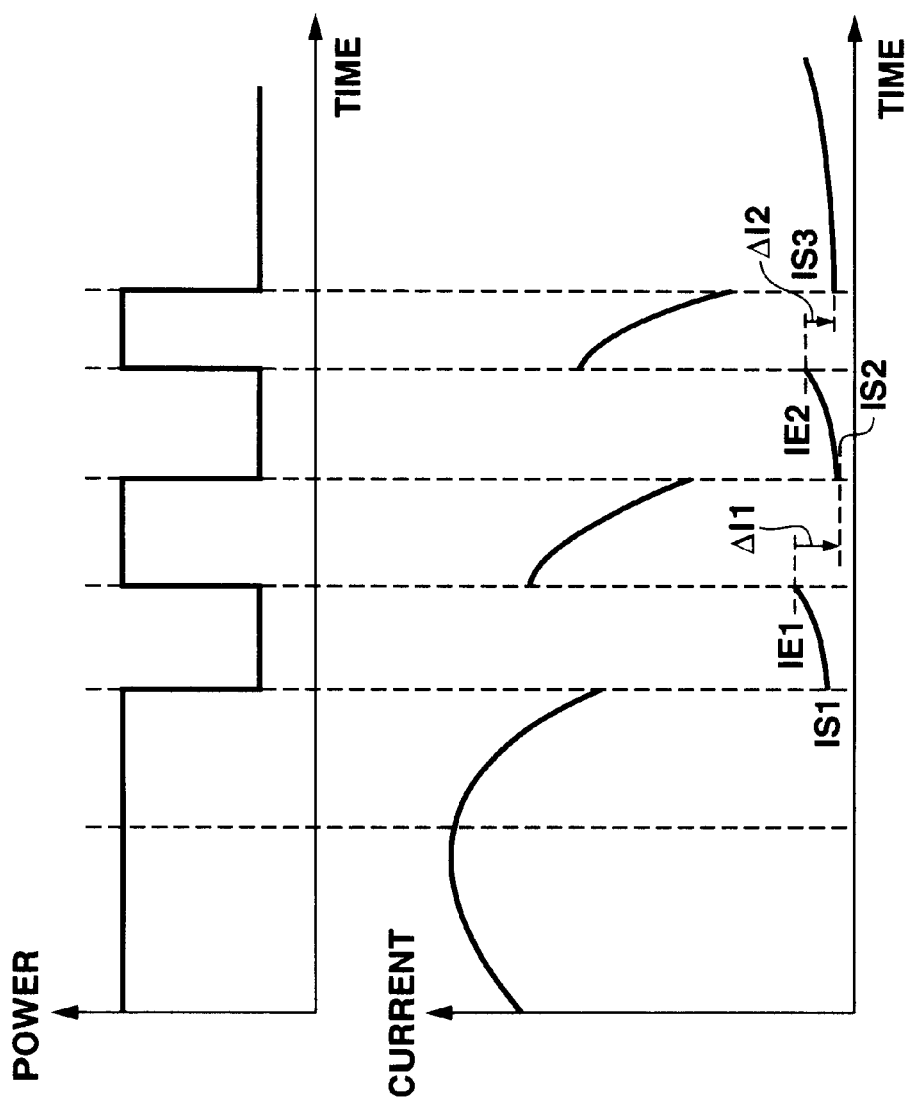
FIG. 17A and FIG. 17B are fourth explanatory diagrams concerning an operation to be exerted by the diathermic power supply shown in FIG. 13.

FIG. 13 to FIG. 17B are concerned with a second embodiment of the present invention. FIG. 13 is a circuit block diagram showing the configuration of a diathermic power supply unit employed in the second embodiment of the present invention. FIG. 14A to FIG. 14C are first explanatory diagrams concerning an operation to be exerted by the diathermic power supply unit. FIG. 14A is a graph showing a variation with the passage of time of high-frequency output power. FIG. 14B is a graph showing a change with the passage of time in the temperature of a living tissue which occurs with delivery of the high-frequency output power shown in FIG. 14A. FIG. 14C is a graph showing a variation with the passage of time of high-frequency current conducted with the high-frequency output power shown in FIG. 14A. FIG. 15A to FIG. 15C are second explanatory diagrams concerning an operation to be exerted by the diathermic power supply unit shown in FIG. 13. FIG. 15A is a graph showing a variation with the passage of time of high-frequency output power. FIG. 15B is a graph showing a change with the passage of time in the temperature of a living tissue which occurs with delivery of the high-frequency output power shown in FIG. 15A. FIG. 15C is a graph showing a variation with the passage of time of high-frequency current conducted with the high-frequency output power shown in FIG. 15A. FIG. 16A and FIG. 16B are third explanatory diagrams concerning an operation to be exerted by the diathermic power supply unit shown in FIG. 13. FIG. 16A is a graph showing a variation with the passage of time of high-frequency output power. FIG. 16B is a graph showing a variation with the passage of time of high-frequency current conducted with the high-frequency output power shown in FIG. 16A. FIG. 17A and FIG. 17B are fourth explanatory diagrams concerning an operation to be exerted by the diathermic power supply unit shown in FIG. 13. FIG. 17A is a graph showing a variation with the passage of time of high-frequency output power. FIG. 17B is a graph showing a variation with the passage of time of high-frequency current conducted with the high-frequency output power shown in FIG. 17A.

The second embodiment is nearly identical to the first embodiment. A difference alone will be described below. The same reference numerals will be assigned to the same components, and the description of the components will be omitted.

As shown in FIG. 13, a diathermic power supply 2D employed in the present embodiment uses current sensors 15a alone to measure output power. The current sensors 15a detect high-frequency current that flows out from the output transformer. The diathermic power supply 2D shown in FIG. 13 adopts the two current sensors 15a. Alternatively, the number of current sensors may be one.

Next, an operation to be exerted by the present embodiment will be described below.

As described in relation to the first embodiment, when high-frequency output power of a constant level shown in FIG. 14A is delivered to a living tissue irrespective of how much time has elapsed, coagulation of the living tissue progresses. Consequently, the temperature of the living tissue rises as show in FIG. 14B. The impedance offered by the living tissue changes accordingly. High-frequency current decreases with an increase in the impedance of the living tissue. Consequently, as shown in FIG. 14C, the high-frequency current behaves contrary to the behavior of the impedance of the living tissue. Namely, after the high-frequency current increases in an early stage, it remains nearly constant for some time, and then abruptly decreases.

When high-frequency output power is, as shown in FIG. 15A, intermittently delivered to a living tissue, high-frequency current is, as shown in FIG. 15C, conducted intermittently. In this case, the temperature of the living tissue changes as shown in FIG. 15B. The impedance offered by the living tissue changes accordingly. High-frequency current conducted with the high-frequency output power decreases during each delivery period of high-frequency output power. After delivery of high-frequency output power is discontinued, when high-frequency output power is delivered again, a large magnitude of high-frequency current can be conducted again. This is because the temperature of a living tissue drops during the pause period during which delivery of high-frequency output power is discontinued.

As mentioned above, high-frequency output power is intermittently delivered. When a living tissue is coagulated over a wide range, high-frequency current conducted during each delivery period of output power gets smaller than the one conducted during an immediately preceding delivery period. Moreover, a rate at which high-frequency current decreases during each delivery period of output power gets higher than a rate at which it decreases during an immediately preceding delivery period, though it depends on how much water is depleted from the living tissue. Owing to this nature of living tissues, the control circuit 17 can judge over how wide a range a living tissue is coagulated.

Assume that feeble high-frequency current of a level not heating a living tissue is, as shown in FIG. 16B or FIG. 17B, conducted during each pause period during which delivery of high-frequency output power is discontinued as shown in FIG. 16A or FIG. 17A. In this case, the feeble high-frequency current gradually increases during the pause period. When a living tissue is coagulated over a wide range, the feeble high-frequency current gets smaller than the one conducted during an immediately preceding pause period. Moreover, a rate at which high-frequency current increases gets higher than the one at which the high-frequency current increases during the immediately preceding pause period. Owing to this nature of living tissues, the control circuit 17 can judge over how wide a range a living tissue is coagulated.

An operation to be exerted by the present embodiment that utilizes the above nature of living tissues will be described below. When a user steps on the footswitch 8, the control circuit 17 extends control to alternately deliver output power of a first level that is a set value and output power of a second level smaller than the first level. Namely, the control circuit 17 does not extend control to repeatedly continue and discontinue delivery of high-frequency output power.

According to the first embodiment, the control circuit 17 calculates an initial value ZS of the impedance offered by a living tissue during any delivery period of output power, and a final value ZE of the impedance offered during the delivery period, and calculates the difference $\Delta Z$ between the values. According to a variant of the first embodiment, the control circuit 17 calculates the initial value ZS of the impedance offered by a living tissue during a delivery period of output power, and calculates a final value ZE of the impedance during an immediately preceding delivery period. The control circuit 17 then calculates the difference $\Delta Z$. Instead, according to the present embodiment, the control circuit 17 measures an initial value IS and a final value IE of high-frequency current conducted during any delivery period of output power of the second level, and then calculates the difference $\Delta I$ between IE and IS ($\Delta I=IE-IS$). When a condition that $\Delta I/IE$ should be smaller than a predetermined value is met, the control circuit 17 judges that alternation of output power of the first level and output power of the second level should be terminated.

Similarly to the first embodiment, the upper limits of a delivery period, a pause period, and the number of times of delivery n may be determined based on a desired coagulated state by a user. Otherwise, the upper limits may be varied depending on high-frequency current or the temperature of a living tissue.

According to the present embodiment, as shown in FIG. 17B, the control circuit 17 may measure the initial value IS of high-frequency current conducted during any delivery period of output power of the second level, and measure the final value IE of high-frequency current conducted during an immediately preceding delivery period of the output power of the second level. The control circuit 17 then may calculate the difference $\Delta I$ of the initial value IS from the final value IE ($\Delta I=IE-IS$). When $\Delta I/IS$ or a change rate of $\Delta I/IS$ exceeds a predetermined value, the control circuit 17 may judge whether alternation of output power of the first level and output power of the second level should be terminated. Otherwise, for example, when high-frequency current falls below a predetermined value that is 150 mA or the like, the control circuit 17 may judge whether alternation of output power of the first level and output power of the second level should be terminated.

High-frequency current induced with a delivery period of output power of the second level may be too small to be measured. In this case, the control circuit 17 may use the initial value IS and final value IE of high-frequency current that is conducted during a delivery period of output power of the first level larger than the second level to judge whether alternation of output power of the first level and output power of the second level should be terminated.

Similarly to the first embodiment, in the present embodiment, the diathermic power supply 2D includes the sensing high-frequency generation circuit 22 and the dc power circuit 21 that supplies dc power to the sensing high-frequency generation circuit 22. When the control circuit 17 is used to measure high-frequency current, delivery of output power can be controlled more accurately. In this case, preferably, the control circuit 17 measures the impedance offered by a living tissue during a delivery period of output power of the second level. This is because when the impedance is measured during the delivery period of output power of the second level, influence of noises can be alleviated.

Similarly to the first embodiment, in the present embodiment, the diathermic power supply 2D may include a temperature sensor that is not shown. In this case, when the temperature of a living tissue has reached, as shown in FIG. 12A, a predetermined value that is 120° or the like, alternation of output power of the first level and output power of the second level similar to repetition of continuation and discontinuation of delivery shown in FIG. 12B may be terminated.

Similarly to the first embodiment, in the present embodiment, the diathermic power supply 2D may control delivery of output power by determining an upper limit and a lower limit of the number of times of alternation n.

The present embodiment provides an advantage described below.

According to the present embodiment, delivery of output power with which high-frequency current is conducted is repeatedly continued and discontinued. Consequently, high-frequency current can be conducted to a living tissue with the temperature of the living tissue held within a range of temperature values that does not bring about carbonization. Therefore, the living tissue is coagulated reliably, while carbonization of the living tissue and adhesion thereof to the electrodes can be prevented.

Furthermore, according to the present embodiment, the current sensors alone are used to control delivery of output power. This results in the electric operation apparatus that is by no means complex but is inexpensive.

Moreover, according to the present embodiment, while high-frequency output power whose level is lower than a set value is delivered, the initial value and final value of high-frequency current conducted with the high-frequency output power are measured. Therefore, the current sensors are unsusceptible to noises caused by high-frequency current. Consequently, delivery of output power can be controlled accurately.

Figure 19:
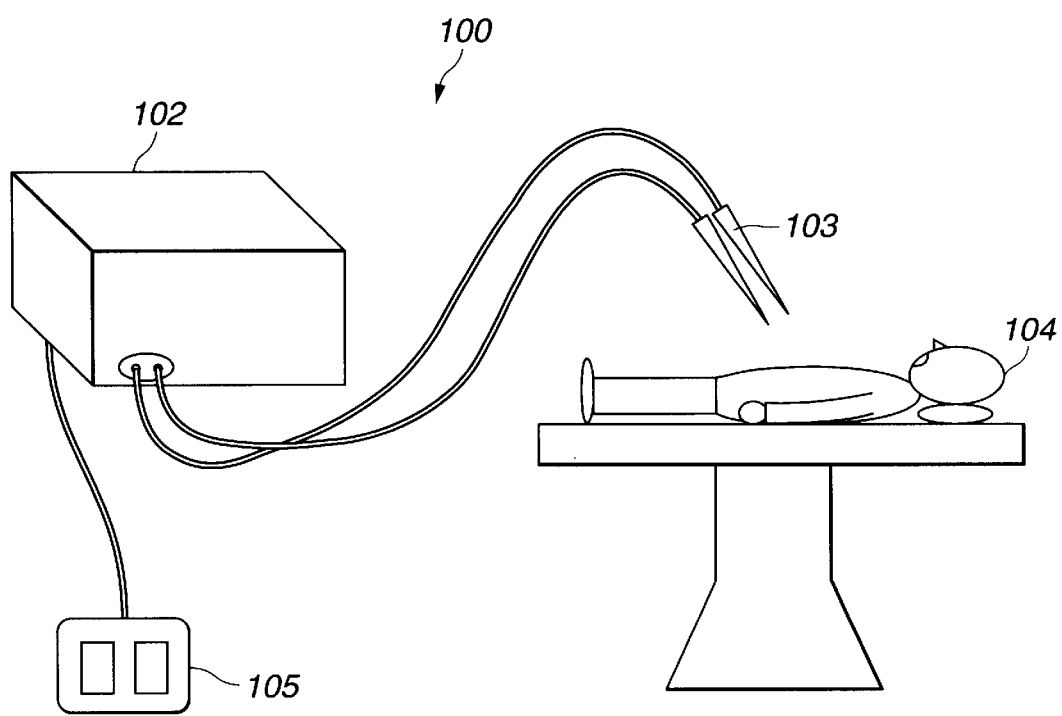
FIG. 19 shows the overall configuration of an electric operation apparatus in accordance with a third embodiment of the present invention.
Figure 20:
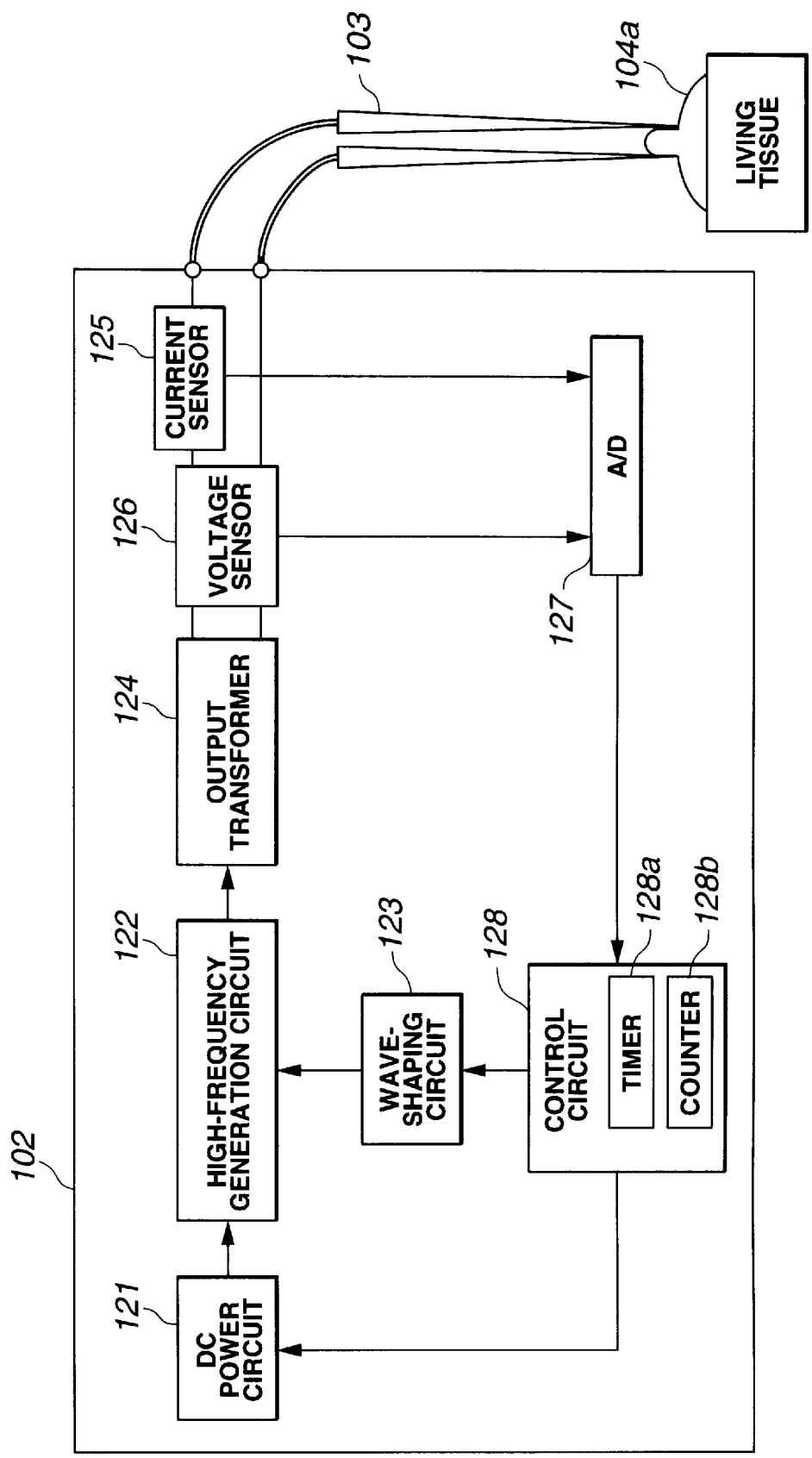
FIG. 20 is a circuit block diagram showing the configuration of a diathermic power supply shown in FIG. 19.
Figure 21:
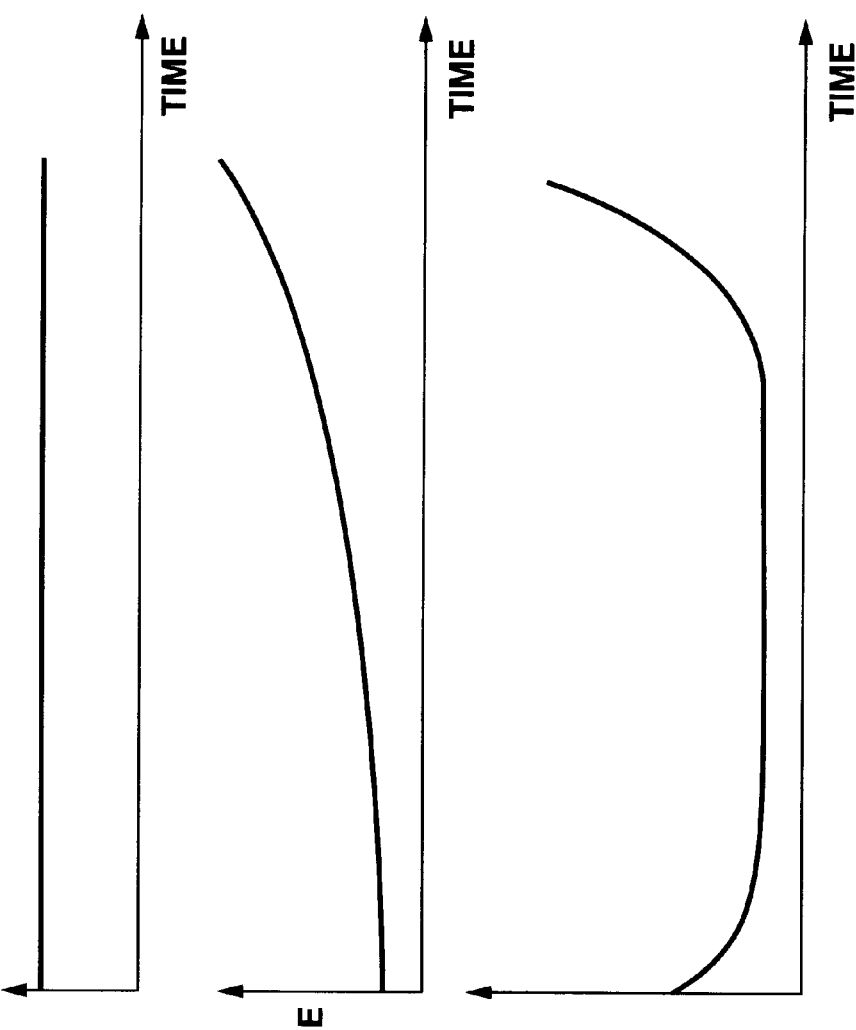
FIG. 21A to FIG. 21C are explanatory diagrams showing the relationships between time and high-frequency output power of a constant level, between time and the temperature of a living tissue, and between time and the impedance offered by the living tissue.
Figure 22:
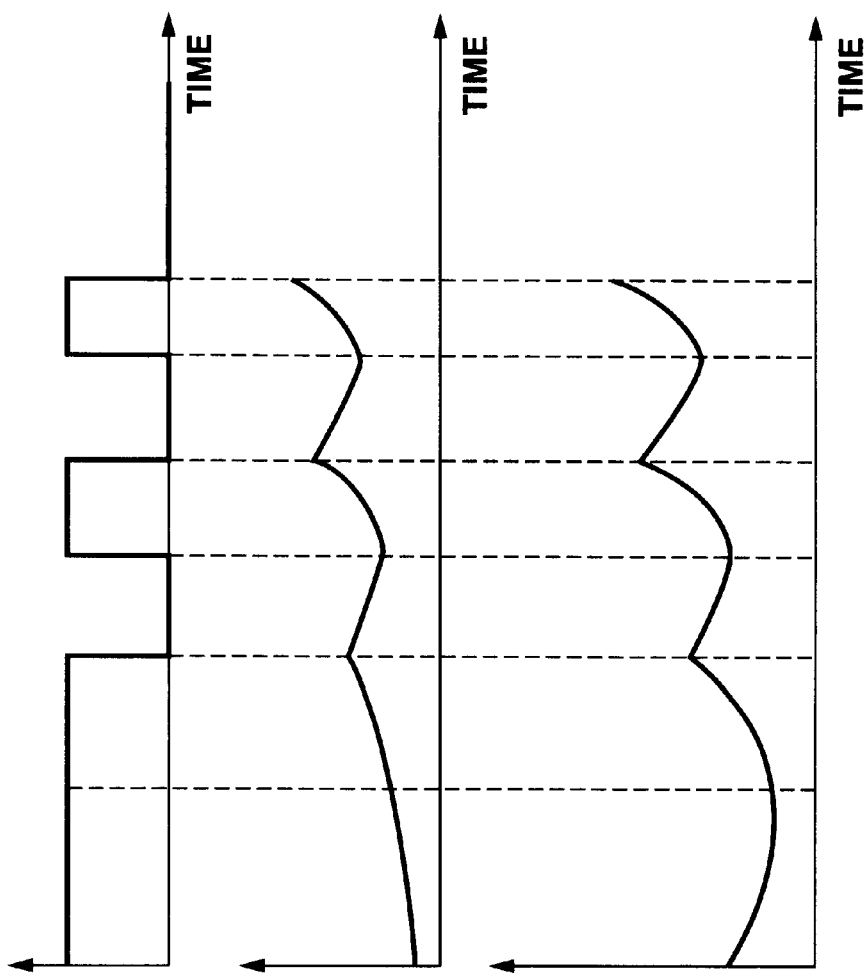
FIG. 22A to FIG. 22C are explanatory diagrams showing the relationships between time and high-frequency output power that is delivered intermittently, between time and the temperature of a living tissue, and between time and the impedance offered by the living tissue.
Figure 23:
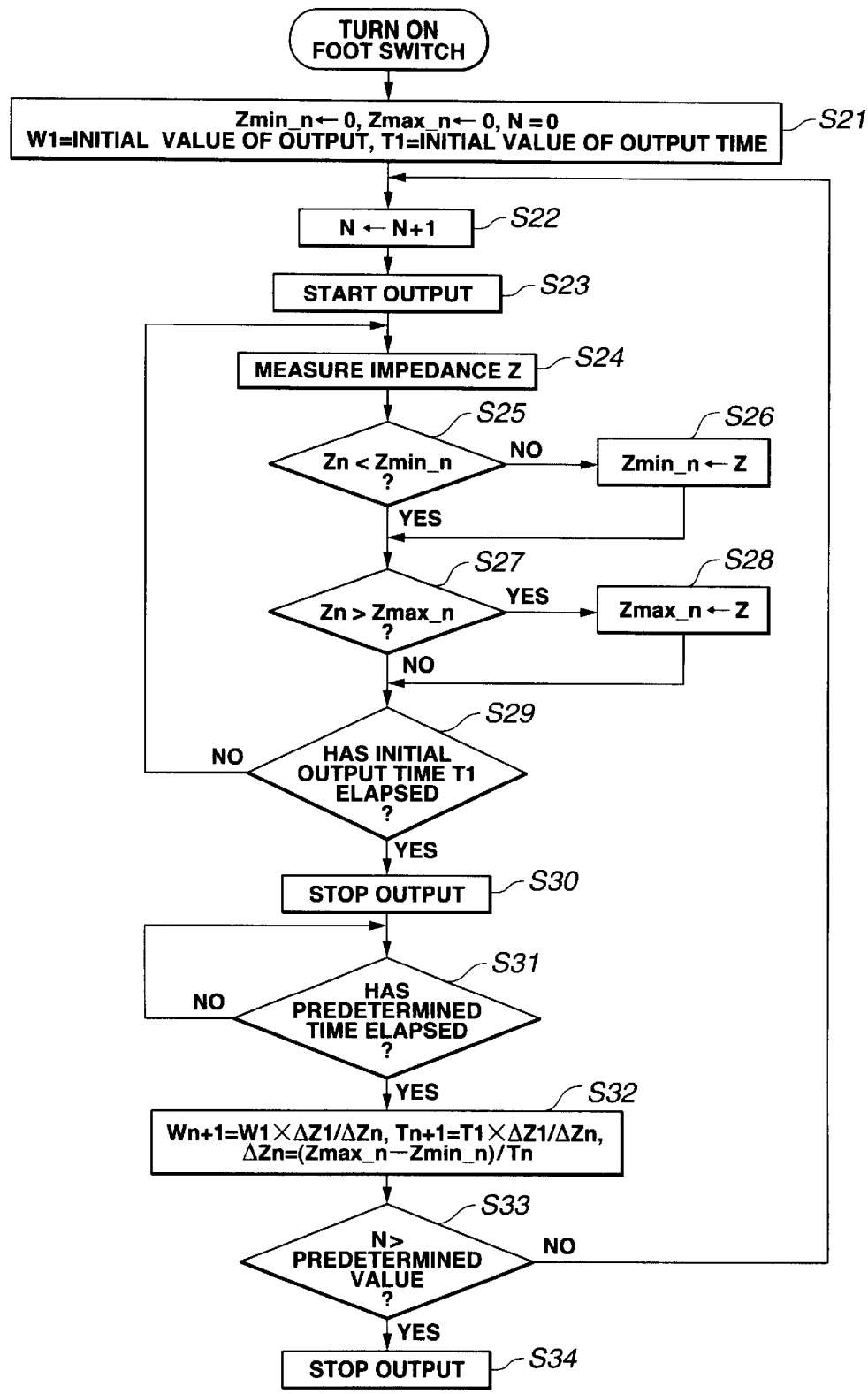
FIG. 23 is a flowchart describing a control sequence followed by a control circuit shown in FIG. 20.
Figures 24A, 24B:
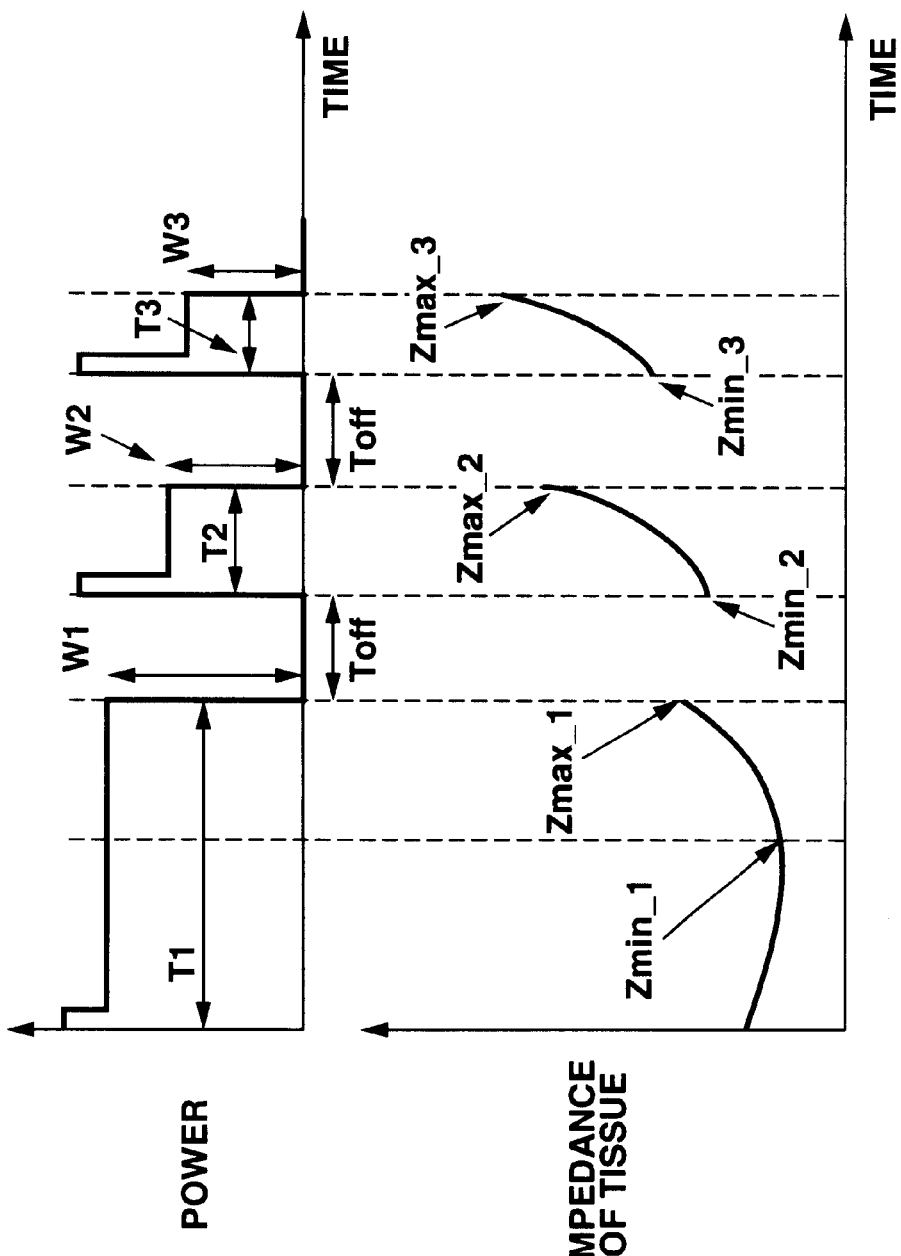
FIG. 24A and FIG. 24B are explanatory diagrams concerning an operation to be exerted by a diathermic power supply that follows the control sequence described in the flowchart of FIG. 23.
Figure 25:
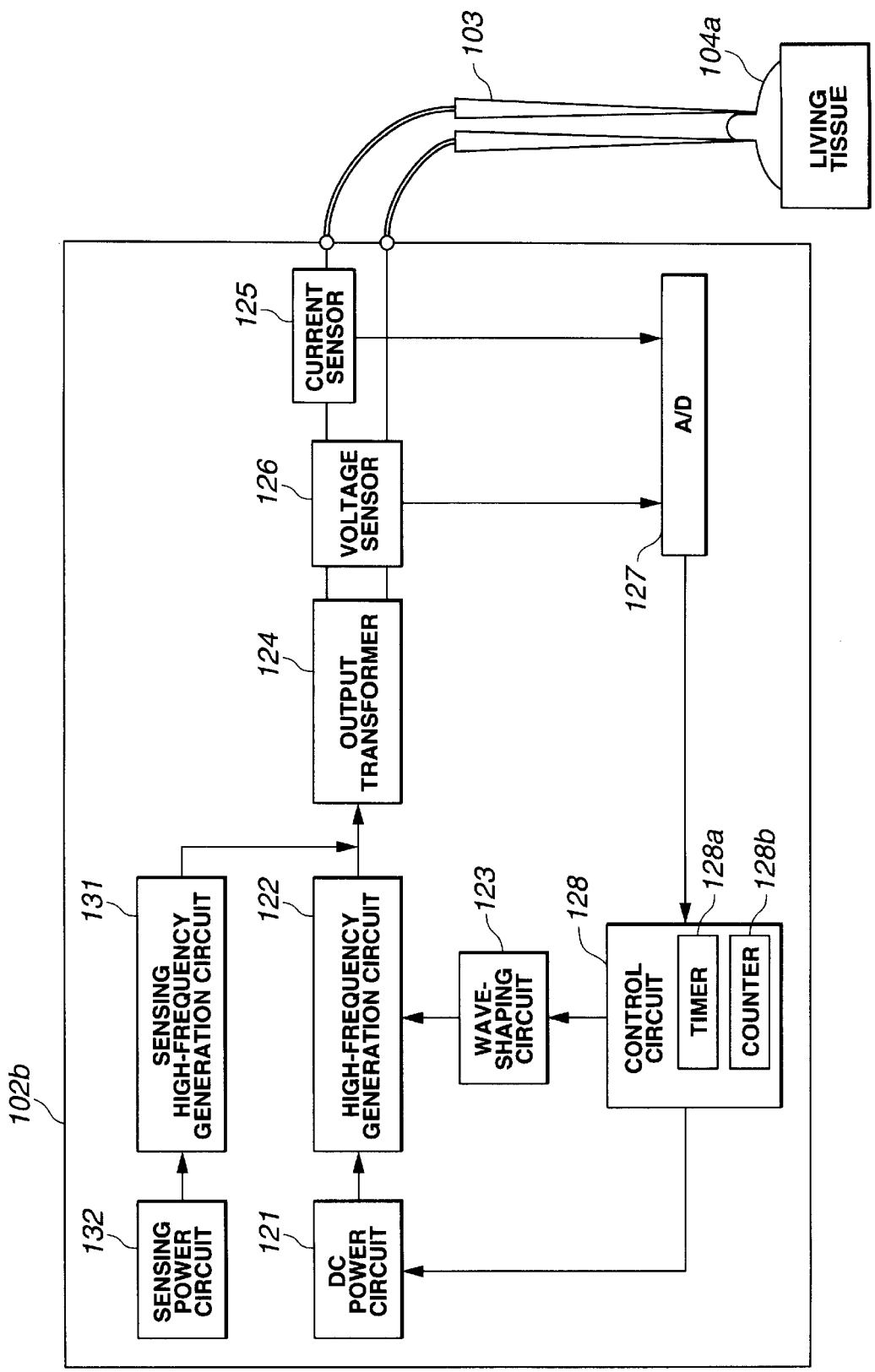
FIG. 25 is a circuit block diagram showing a diathermic power supply employed in a first variant.
Figures 26A, 26B:
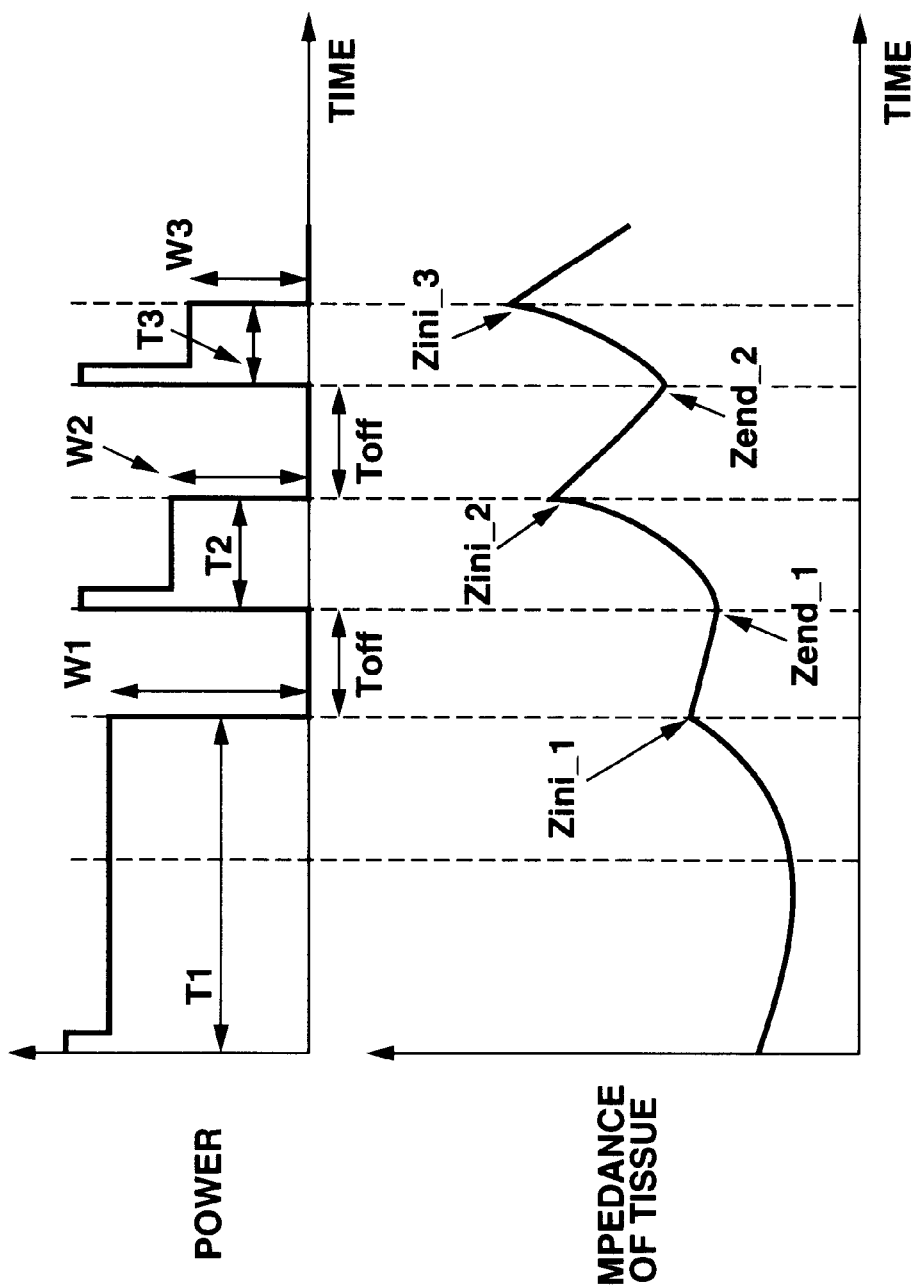
FIG. 26A and FIG. 26B are explanatory diagrams concerning an operation to be exerted by the diathermic power supply employed in the first variant.
Figure 27:
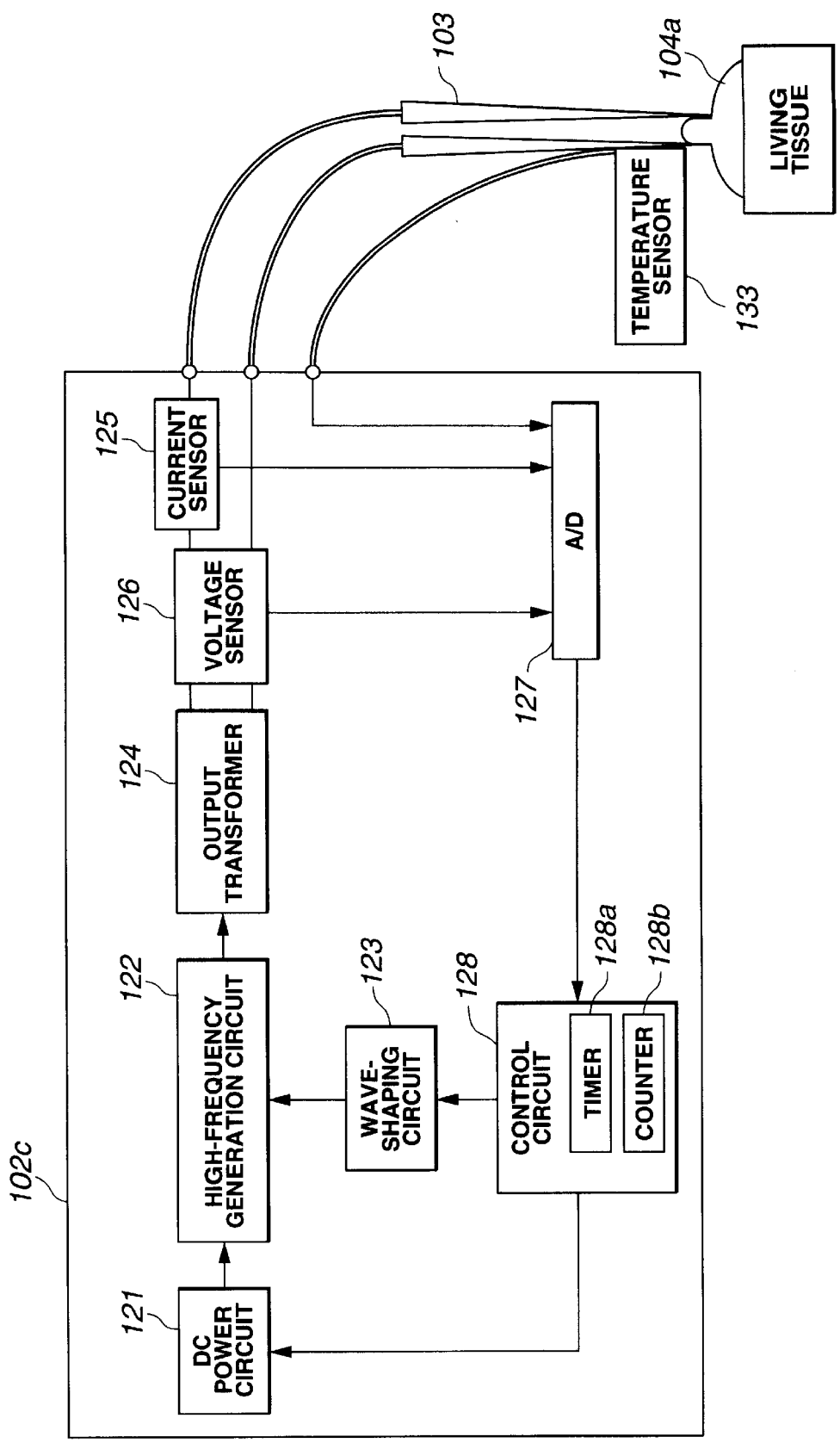
FIG. 27 is a circuit block diagram showing a diathermic power supply employed in a second variant.
Figure 28:
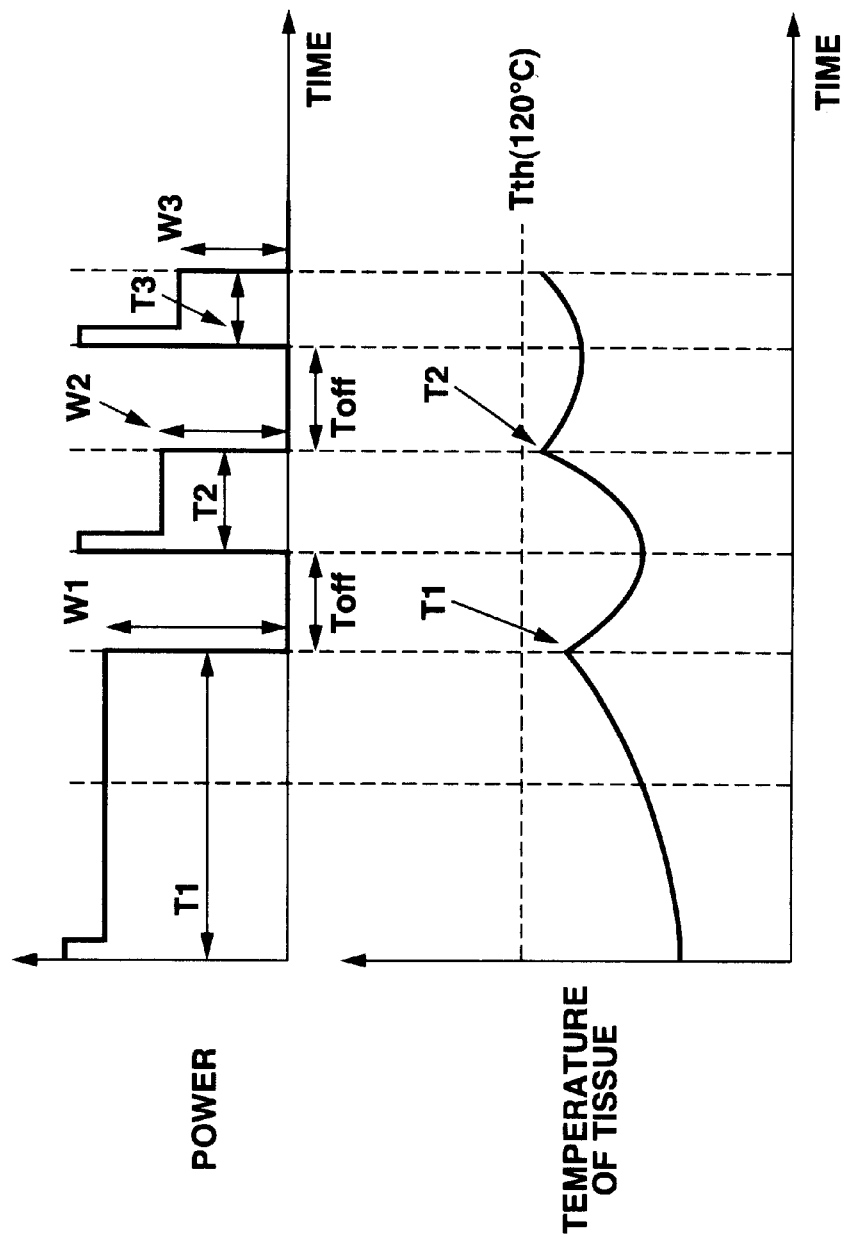
FIG. 28A and FIG. 28B are explanatory diagrams concerning an operation to be exerted by the diathermic power supply employed in the second variant shown in FIG. 27.
Figure 29:
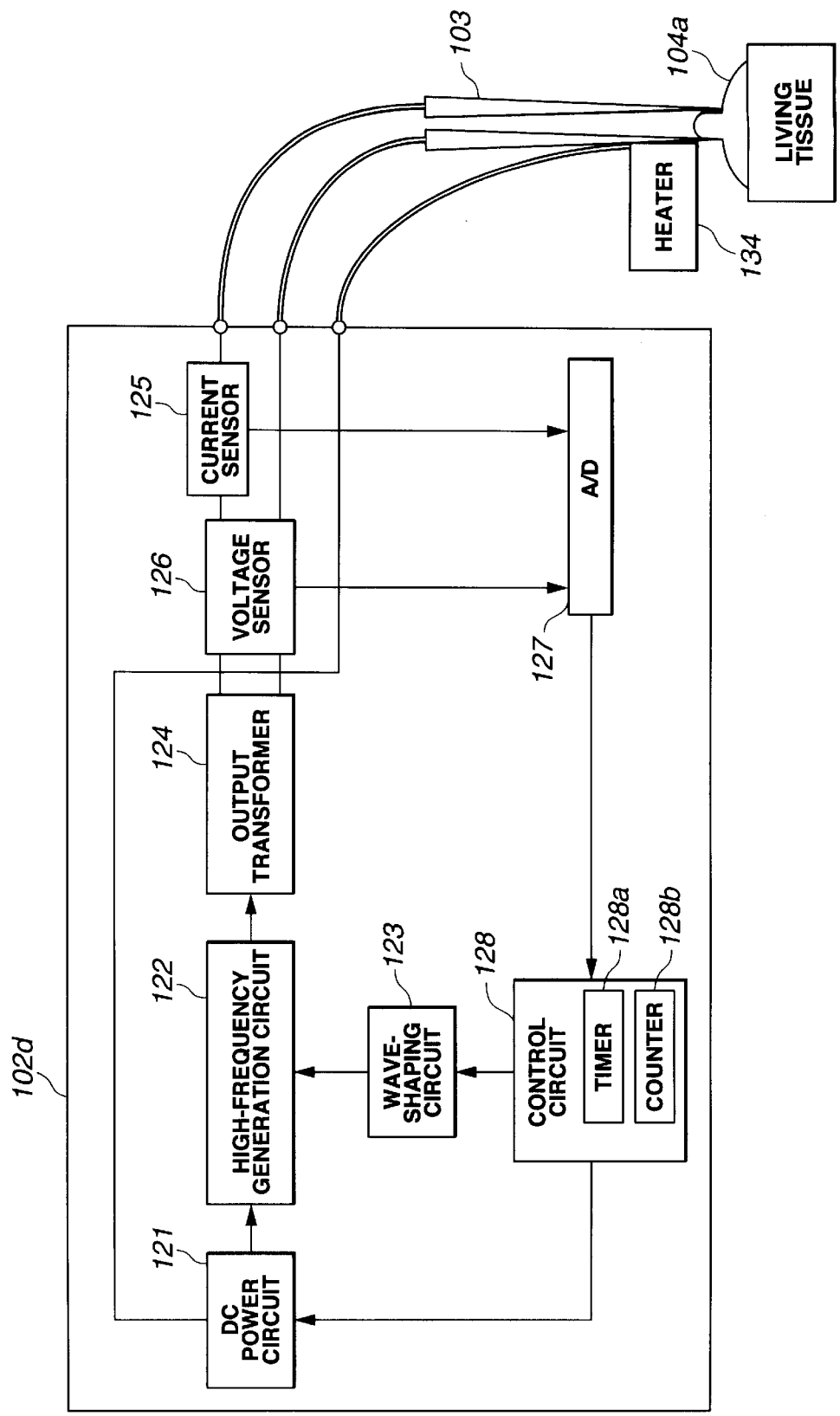
FIG. 29 is a circuit block diagram showing a diathermic power supply employed in a third variant.

FIG. 19 to FIG. 29 are concerned with a third embodiment of the present invention. FIG. 19 shows the overall configuration of an electric operation apparatus in accordance with the third embodiment of the present invention. FIG. 20 is a circuit block diagram showing the circuitry of a diathermic power supply shown in FIG. 19. FIG. 21A to FIG. 21C are explanatory diagrams showing the relationships to time of high-frequency output power of a constant level, the temperature exhibited by a living tissue, and the impedance offered thereby. FIG. 21A is a graph showing a variation with the passage of time of high-frequency output power. FIG. 21B is a graph showing a change with the passage of time in the temperature exhibited by a living tissue which occurs with delivery of the high-frequency output power shown in FIG. 21A. FIG. 21C is a graph showing a change with the passage of time in the impedance offered by the living tissue which occurs with delivery of the high-frequency output power shown in FIG. 21A. FIG. 22A to FIG. 22C are explanatory diagrams showing the relationships to time of high-frequency output power that is delivered intermittently, the temperature exhibited by a living tissue, and the impedance offered thereby. FIG. 22A is a graph showing a variation with the passage of time of high-frequency output power. FIG. 22B is a graph showing a change with the passage of time in the temperature exhibited by a living tissue which occurs with delivery of the high-frequency output power shown in FIG. 22A. FIG. 22C is a graph showing a change with the passage of time in the impedance offered by the living tissue which occurs with delivery of the high-frequency output power shown in FIG. 22A. FIG. 23 is a flowchart describing a control sequence followed by a control circuit shown in FIG. 20. FIG. 24A and FIG. 24B are explanatory diagrams concerning an operation to be exerted by the diathermic power supply that follows the control sequence described in the flowchart of FIG. 23. FIG. 24A is a graph showing a variation with the passage of time of high-frequency output power. FIG. 24B is a graph showing a change with the passage of time in the impedance offered by a living tissue which occurs with delivery of the high-frequency output power shown in FIG. 24A. FIG. 25 is a circuit block diagram showing a diathermic power supply employed in a first variant. FIG. 26A and FIG. 26B are explanatory diagrams concerning an operation to be exerted by the diathermic power supply employed in the first variant. FIG. 26A is a graph showing a variation with the passage of time of high-frequency output power. FIG. 26B is a graph showing a change with the passage of time in the impedance offered by a living tissue which occurs with delivery of the high-frequency output power shown in FIG. 26A. FIG. 27 is a circuit block diagram showing a diathermic power supply employed in a second variant. FIG. 28A and FIG. 28B are explanatory diagrams concerning an operation to be exerted by the diathermic power supply employed in the second variant. FIG. 28A is a graph showing a variation with the passage of time of high-frequency output power. FIG. 28B is a graph showing a change with the passage of time in the temperature exhibited by a living tissue which occurs with delivery of the high-frequency output power shown in FIG. 28A. FIG. 29 is a circuit block diagram showing a diathermic power supply employed in a third variant.

As shown in FIG. 19, an electric operation apparatus 100 in accordance with the third embodiment consists mainly of a diathermic power supply 102 and a pair of electrodes 103. High-frequency output power generated by the diathermic power supply 102 is delivered to a living tissue 104a of a patient 104 via the pair of electrodes 103 that serves as a therapeutic accessory (operating instrument). A footswitch 105 used to switch delivery and non-delivery of high-frequency output power is connected to the diathermic power supply 102.

The pair of electrodes 103 is used to clamp the living tissue 104a of the patient 104, whereby high-frequency current is conducted to the living tissue 104a clamped with the electrodes 103. The electrodes 103 may be either single-pole electrodes or multi-pole electrodes.

As shown in FIG. 20, the diathermic power supply 102 consists mainly of a dc power circuit 121, a high-frequency generation circuit 122, a wave-shaping circuit 123, an output transformer 124, a current sensor 125, a voltage sensor 126, an A/D converter 127, and a control circuit 128. The dc power circuit 121 supplies dc power. The high-frequency generation circuit 122 converts the dc power supplied from the dc power circuit 121 into high-frequency output power. The wave-shaping circuit 123 controls the high-frequency generation circuit 122 in terms of the waveshape of the high-frequency output power. The output transformer 124 transfers the high-frequency output power generated by the high-frequency generation circuit 22 to the electrodes 103. The current sensor 125 detects current that flows out from the output transformer 124. The voltage sensor 126 detects voltage that is induced by the output transformer 124. The A/D converter 127 digitizes the current and voltage values transferred from the current sensor 125 and voltage sensor 126 respectively. Based on the current and voltage values digitized by the A/D converter 127, the control circuit 128 controls the dc power circuit 121 and wave-shaping circuit 123.

The control circuit 128 has a timer 128a and a counter 128b. The timer 128a indicates passage of time since start of delivery of output power with which high-frequency current is conducted to the living tissue 104a. The counter 128b counts the number of times of delivery of high-frequency output power.

The control circuit 128 judges the coagulated state of the living tissue 104a from biomedical information and the number of times of delivery by which delivery of high-frequency output power is repeated. The biomedical information includes the detected current and voltage values, the calculated impedance, and the detected temperature of a living tissue. Moreover, the control circuit 128 transfers the judged coagulated state of the living tissue 104a to a monitor or a liquid crystal panel. The monitor that is not shown serves as a display means, and the liquid crystal panel that is not shown is included in the housing of the diathermic power supply 104. Consequently, the judged coagulated state of the living tissue 104a is presented on the monitor or liquid crystal panel.

A user clamps the living tissue 104a of the patient 104 using the pair of electrodes 103 included in the electric operation apparatus 100, and turns on the footswitch 105. High-frequency output power is then delivered to the living tissue 104a clamped with the pair of electrodes 103. High-frequency current conducted with the high-frequency output power heats the living tissue 104a. Due to the heating, the living tissue 104a is denatured and dried up with the water contained therein depleted. The living tissue 104a is coagulated in due course. Although the living tissue 104a has dried up, if high-frequency output power is kept delivered, the living tissue 104a is carbonized to adhere to the electrodes 103. In order to prevent the living tissue 104a from adhering to the electrodes 103, delivery of high-frequency output power must be stopped as soon as the living tissue 104a has dried.

When high-frequency output power of a constant level shown in FIG. 21A is delivered to the living tissue 104a irrespective of how much time has elapsed, the living tissue 104a is heated. The temperature of the living tissue rises, as shown in FIG. 21B, along with progress in denaturation and drying. On the other hand, as shown in FIG. 21C, the impedance offered by the living tissue decreases in an early stage, remains nearly constant for some time, and then abruptly rises with the dry of the living tissue. Conventionally, as soon as it is judged from the impedance or temperature of the living tissue that the living tissue has dried up, delivery of high-frequency output power is stopped.

In contrast, according to the present embodiment, high-frequency output power is delivered intermittently as shown in FIG. 22A. As shown in FIG. 22B, the impedance offered by a living tissue increases and then decreases with discontinuation of delivery of high-frequency output power. Likewise, as shown in FIG. 22C, the temperature exhibited by the living tissue rises and then drops with discontinuation of delivery of high-frequency output power. When high-frequency output power is delivered again, the impedance of the living tissue increases and the temperature thereof rises. This procedure is repeated, whereby the living tissue 104a is held denatured and dried according to the present embodiment. Carbonization of the living tissue and adhesion thereof derived from a rise in the temperature of the living tissue (which occurs when high-frequency output power is delivered continuously) can be prevented, while a large magnitude of high-frequency current can be conducted. According to the present embodiment, compared with the aforesaid conventional method, a living tissue can be coagulated over a wider range.

As mentioned above, high-frequency output power is delivered intermittently. When a living tissue is coagulated over a wide range, the impedance offered by the living tissue during each delivery period of the output power gets larger than the one offered during an immediately preceding delivery period. Likewise, the temperature exhibited by the living tissue during each delivery period of the output power gets higher than the one exhibited during the immediately preceding delivery period.

As mentioned above, high-frequency output power is delivered intermittently. When a living tissue is coagulated over a wide range, the impedance offered by the living tissue during each delivery period gets larger than the one offered thereby during an immediately preceding delivery period. Likewise, the temperature exhibited by the living tissue during each delivery period gets higher than the one exhibited thereby during the immediately preceding delivery period. Moreover, rates at which the impedance of the living tissue increases during each delivery period and the temperature thereof rises during the same period get higher than the ones at which the impedance increases during the immediately preceding delivery period and the temperature rises during the same period. Rates at which the impedance of the living tissue decreases during each pause period and the temperature thereof drops during the same period get higher accordingly. Owing to this nature of living tissues, the control circuit 17 judges over how wide a range a living tissue has been coagulated.

An operation to be exerted by the present embodiment that utilizes the nature of living tissues will be described in conjunction with the flowchart of FIG. 23.

As mentioned above, the living tissue 104a of the patient 104 is clamped using the pair of electrodes 103, and the footswitch 105 is turned on. When the footswitch 105 is stepped on, the control circuit 128 starts following a control sequence described in the flowchart of FIG. 23.

When the footswitch 105 is turned on, the control circuit 128 resets a minimum value $Z_{min\_n}$ of the impedance offered by a living tissue during a delivery period of high-frequency output power to the infinite $\infty$ at step S21 described in FIG. 23. Moreover, the control circuit 128 resets a maximum value $Z_{max\_n}$ of the impedance to 0, output power W1 to a predetermined initial value, and a delivery period T1 to a predetermined initial value.

At step S22, the control circuit 128 instructs the counter 128b to count the number of times of delivery N. At step S23, delivery of high-frequency output power is started. As soon as delivery is started, the control circuit 128 starts up the timer 128a. The timer 128a starts indicating passage of time. At step S24, the control circuit 128 receives signals from the current sensor 125 and voltage sensor 126 respectively via the A/D converter 27, calculates the impedance Zn offered by the living tissue, and stores the impedance in a memory that is not shown. The control circuit 128 compares the sequentially calculated impedance Zn with the minimum value Zmin_n and maximum value Zmax_n at steps S25 to S28. The minimum value Zmin_n and maximum value Zmax_n are thus corrected time-sequentially.

At step S29, the control circuit 128 judges whether the delivery period during which high-frequency output power is delivered is longer than an initial delivery period T1. If the delivery period is not longer than the initial delivery period T1, step S24 and subsequent steps are repeated. In contrast, if the delivery period during which high-frequency output power is delivered is longer than the initial delivery period T1, the delivery is discontinued for predetermined time that is, for example, 0.5 sec at step S30. The control circuit 128 judges at step S31 whether the predetermined time has elapsed. If the predetermined time has elapsed, second set values ΔZ2, W2, and T2 are calculated at step S32.

The second set values ΔZ2, W2, and T2 are calculated according to the relational expressions presented below.

$$\Delta Zn = (Zmax - Zmin)/Tn \quad (1)$$

$$Wn+1 = W1 \cdot \Delta Z1/\Delta Zn \quad (2)$$

$$Tn+1 = T1 \cdot \Delta Z1/\Delta Zn \quad (3)$$

where n denotes the number of times of delivery ($n \geq 2$).

A change rate ΔZn of the impedance offered by a living tissue gets higher with progress in coagulation. When the output power and delivery period are set to the above set values, the output power and delivery period for the third delivery period or subsequent delivery period can be reduced and shortened. Consequently, carbonization of the living tissue 104a and adhesion thereof to the electrodes 103 can be prevented.

After step S32 is completed, the control circuit 128 judges at step S33 whether the number of times of delivery N has reached a predetermined value. If not, the output power and delivery period are set to the second set values W2 and T2 respectively. Steps S3 and subsequent steps are then repeated. If the number of times of delivery N has reached the predetermined value, the control circuit 128 terminates repetition of continuation and discontinuation of delivery of high-frequency output power so as to stop delivery at step S34. When delivery of high-frequency output power is started at step S23, the control circuit 128 extends control to deliver high-frequency output power, of which level is larger than the set value, during predetermined time that is, for example, 0.1 sec. This is intended to prevent adhesion of the living tissue 104a to the electrodes 103.

FIG. 24A and FIG. 24B show a variation with the passage of time of high-frequency output power and a change with the passage of time in the impedance offered by a living tissue which occur when the control circuit 128 follows the foregoing control sequence.

As mentioned above, immediately after delivery of high-frequency output power is started, high-frequency output power whose level is larger than the set value is, as shown in FIG. 24A, delivered for the predetermined time that is, for example, 0.1 sec. This is intended to prevent adhesion of the living tissue 104a to the electrodes 103. Thereafter, high-frequency output power of the predetermined initial level W1 is delivered.

When high-frequency current is conducted with the high-frequency output power W1, the impedance offered by a living tissue decreases to Zmin_1 in an early stage as shown in FIG. 24B. Thereafter, the impedance increases up to Zmax_1 until the predetermined initial delivery period T1 elapses. Delivery of high-frequency output power is then discontinued for predetermined time of 0.5 sec or the like. Thereafter, high-frequency output power of the level W2 that is the calculated second set value is delivered until the delivery period T2 elapses. Consequently, the impedance of the living tissue increases from Zmin_2 to Zmax_2.

After the delivery period T2 has elapsed, delivery of high-frequency output power is discontinued for the predetermined time. High-frequency output power of the level W3 that is equal to the third set value is then delivered until the delivery period T3 elapses. Consequently, the impedance of the living tissue increases from Zmin_3 to Zmax_3.

As mentioned above, continuation and discontinuation of delivery of high-frequency output power is repeated. Herein, the magnitude of output power, the delivery period, and the pause period can be varied. An operator may set any values as the initial value W1 of output power that is equal to a set value, the initial value T1 of the delivery period, and the pause period during which delivery is discontinued. Moreover, when the delivery period gets shorter because a change rate of the impedance offered by a living tissue increases, the pause period during which delivery is discontinued may be short. The control circuit 128 may therefore change the pause period according to the delivery period, that is, determine the pause period as a product of the delivery period by 0.5 or the like.

Consequently, according to the present invention, high-frequency output power can be delivered with the temperature of the living tissue 104a held within a range of temperature values that does not bring about carbonization. The living tissue can therefore be coagulated reliably, while carbonization of the living tissue 104a and adhesion thereof to the electrodes 103 can be prevented.

The relational expressions providing the set values of output power and delivery period are not limited to the aforesaid expressions (1) to (3). The expressions may be modified based on a desired degree of coagulation. Moreover, the degree of coagulation may be able to be designated on an operator panel that is not shown.

As shown in FIG. 25, a diathermic power supply 102b includes a sensing high-frequency generation circuit 131 and a sensing power circuit 132. The sensing high-frequency circuit 131 calculates the impedance offered by a living tissue during the pause period during which delivery of high-frequency output power for use in remedy is discontinued. The sensing power circuit 132 supplies dc power to the sensing high-frequency generation circuit 131.

FIG. 26A and FIG. 26B show a variation with the passage of time of high-frequency output power and a change with the passage of time in the impedance of a living tissue which occur when the diathermic power supply 102b is employed.

In this case, the control circuit 128 calculates the impedance Zmin_n offered by a living tissue immediately after delivery of high-frequency output power is discontinued, and also calculates the impedance Zend_n offered thereby immediately before high-frequency output power is delivered next. A change rate ΔZ of the impedance offered by the living tissue is calculated as follows:

$$\Delta Z = (Zend\_n - Zmin\_n)/Tn \quad (4)$$

where n denotes the number of times of delivery ($n \geq 2$).

Consequently, according to the present variant, influence of noises derived from high-frequency output power for use in treatment can be alleviated, and delivery of output power can be controlled more accurately.

Moreover, as shown in FIG. 27, a diathermic power supply 102c has a temperature sensor 133 fixed to one of the electrodes 103 that clamp the living tissue 104a of a patient. The temperature of the living tissue detected by the temperature sensor 133 may be used to determine the output power and delivery period.

FIG. 28A and FIG. 28B show a variation with the passage of time of high-frequency output power and a change with the passage of time in the impedance offered by a living tissue which occur when the diathermic power supply 102c is employed.

In this case, the control circuit 128 may calculate the output power and delivery according to the following relational expressions:

Output power $Wn+1 = W1 \cdot (Tth-Tn)/Tth$  (5)

Delivery period $Tn = T1 \cdot (Tth-Tn)/Tth$  (6)

where T denotes the temperature of a living tissue detected by the temperature sensor 133, and Tth denotes a threshold of the temperature of the living tissue. Noted at this time is that the temperature T of a living tissue must not exceed the threshold Tth for the temperature of a living tissue.

Referring to FIG. 28B, the threshold Tth for the temperature of a living tissue is, for example, 120°.

Moreover, the diathermic power supply may not deliver high-frequency output power, of which level is higher than a set value, in an early stage of delivery of high-frequency output power performed at step S23 described in the flowchart of FIG. 23. Instead, the diathermic power supply may have the components shown in FIG. 29.

As shown in FIG. 29, a diathermic power supply 102d has a heater 134 fixed to one of the electrodes 103 that clamp the living tissue 104a of a patient. The heater 134 is used to heat the electrodes 103 prior to delivery of output power.

As long as the natures of the living tissue 104a are already known, the output power and delivery period to be calculated by the control circuit 128 may be defined based on the number of times of delivery N as follows:

Output power $Wn = W1/N$  (7)

Delivery period $Tn = T1/N$  (8)

Even the present variant provides the same advantage as the third embodiment.

Figure 30:
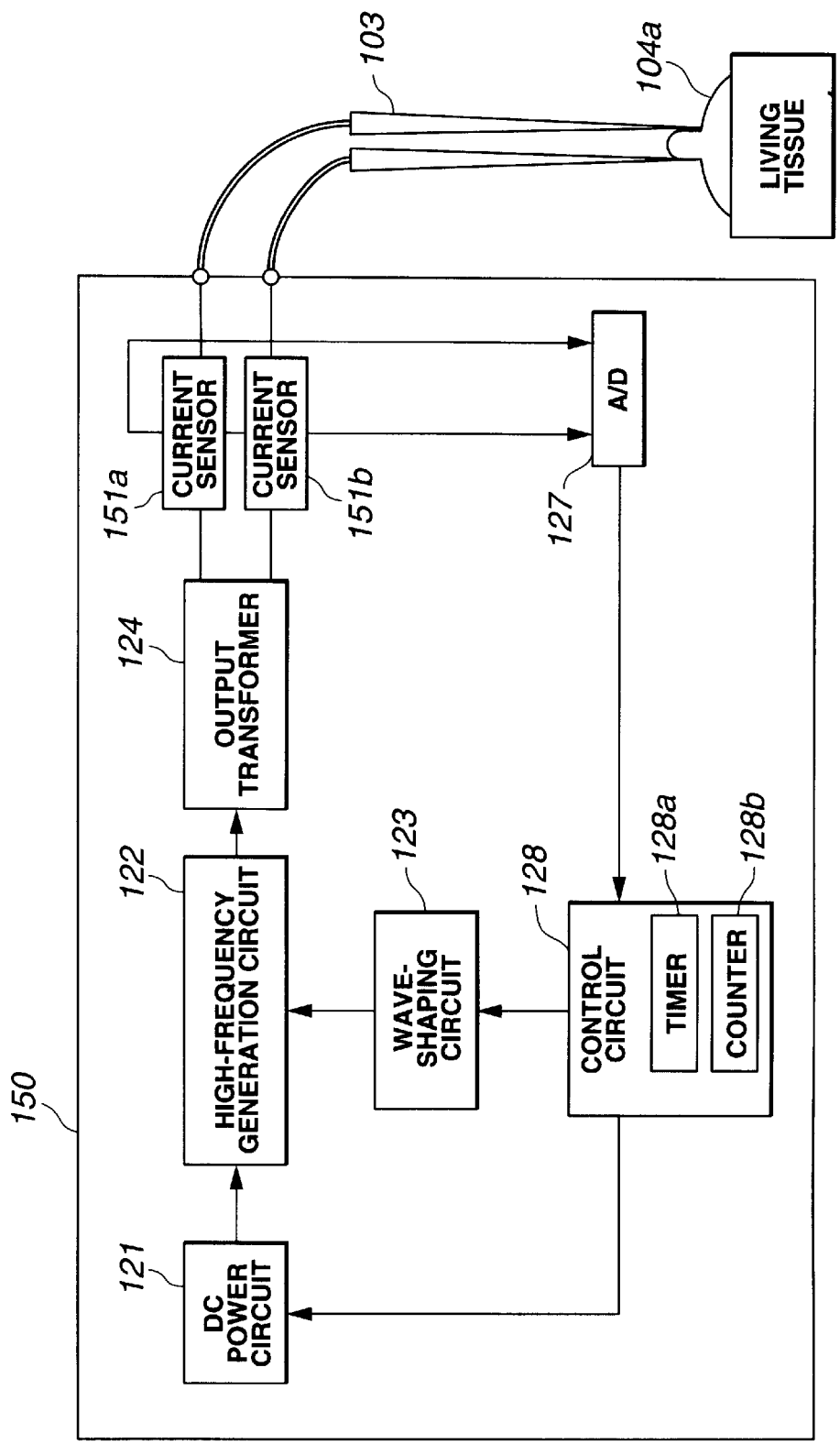
FIG. 30 is a circuit block diagram showing the circuitry of a diathermic power supply employed in a fourth embodiment of the present invention.
Figures 33A, 33B:
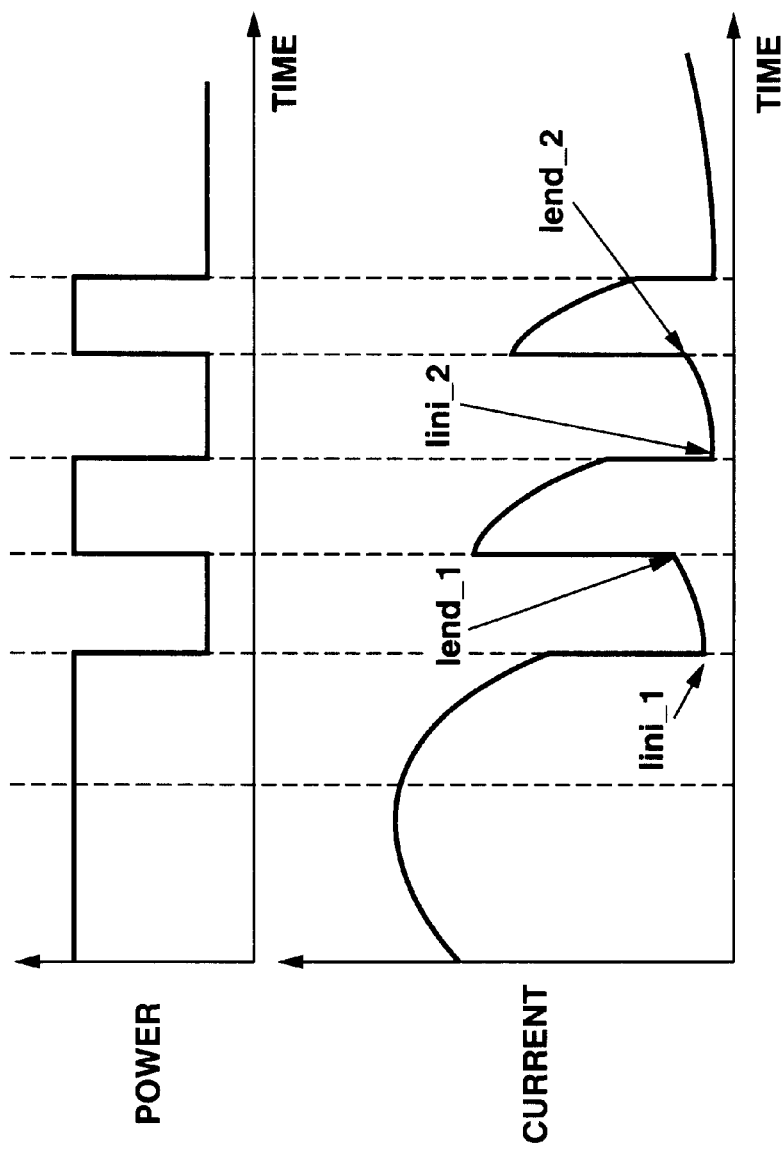
FIG. 33A to FIG. 33B are third explanatory diagrams concerning an operation to be exerted by the diathermic power supply shown in FIG. 30.

FIG. 30 to FIG. 33B are concerned with a fourth embodiment of the present invention. FIG. 30 is a circuit block diagram showing the circuitry of a diathermic power supply employed in the fourth embodiment of the present invention. FIG. 31A to FIG. 31C are first explanatory diagrams concerning an operation to be exerted by the diathermic power supply shown in FIG. 30. FIG. 31A is a graph showing a variation with the passage of time of high-frequency output power. FIG. 31B is a graph showing a change with the passage of time in the temperature exhibited by a living tissue which occurs with delivery of the high-frequency output power shown in FIG. 31A. FIG. 31C is a graph showing a variation with the passage of time of high-frequency current conducted with the high-frequency output power shown in FIG. 31A. FIG. 32A to FIG. 32C are second explanatory diagrams concerning an operation to be exerted by the diathermic power supply shown in FIG. 30. FIG. 32A is a graph showing a variation with the passage of time of high-frequency output power. FIG. 32B is a graph showing a change with the passage of time in the temperature exhibited by a living tissue which occurs with delivery of the high-frequency output power shown in FIG. 32A. FIG. 32C is a graph showing a variation with the passage of time of high-frequency current conducted with the high-frequency output power shown in FIG. 32A. FIG. 33A and FIG. 33B are third explanatory diagrams concerning an operation to be exerted by the diathermic power supply shown in FIG. 30. FIG. 33A is a graph showing a variation with the passage of time of high-frequency output power. FIG. 33B is a graph showing a variation with the passage of time of high-frequency current conducted with the high-frequency output power shown in FIG. 33A.

According to the aforesaid third embodiment, the current and voltage values transferred from the current sensor 125 and voltage sensor 126 are used to calculate the impedance offered by a living tissue. The impedance of the living tissue is used to control output power. According to the fourth embodiment, only the current value transferred from the current sensor 125 is used to control output power. The other components are nearly identical to those of the third embodiment. The description of the components will therefore be omitted, and the same reference numerals will be assigned to the components.

As shown in FIG. 30, a diathermic power supply 150 employed in an electric operation apparatus in accordance with the fourth embodiment of the present invention uses current sensors 151a and 151b alone to detect high-frequency current that flows out from the output transformer 124.

As described in relation to the third embodiment, when high-frequency output power of a constant level shown in FIG. 31A is delivered to the living tissue 104a irrespective of how much time has elapsed, coagulation of the living tissue 104a progresses. The temperature exhibited by the living tissue 104a rises as shown in FIG. 31B. The impedance offered by the living tissue changes accordingly. When the impedance of the living tissue increases, high-frequency current decreases. As shown in FIG. 31C, the high-frequency current behaves contrary to the impedance of the living tissue (see FIG. 21C). Specifically, the high-frequency current increases in an early stage, remains nearly constant for some time, and then abruptly decreases along with the dry of the living tissue 104a.

High-frequency output power is, as shown in FIG. 32A, intermittently delivered to the living tissue 104a. High-frequency current is therefore, as shown in FIG. 32C, conducted intermittently. Consequently, the temperature exhibited by the living tissue 104a changes as shown in FIG. 32B. The impedance offered by the living tissue changes accordingly. High-frequency current decreases during each delivery period of high-frequency output power. After delivery of high-frequency output power is discontinued, when high-frequency output power is delivered again, a large magnitude of high-frequency current is conducted again. This is because the temperature of the living tissue drops during the pause period.

When high-frequency output power is delivered intermittently, the living tissue 104a is coagulated over a wide range. Consequently, high-frequency current conducted during each delivery period gets smaller than the one conducted during the immediately preceding delivery period. Moreover, a rate at which high-frequency current decreases during each delivery period gets higher than the one at which the high-frequency current decreases during the immediately preceding delivery period. This is because water contained in the living tissue 104a is depleted. Owing to this nature of living tissues, the control circuit 17 can judge over how wide a range the living tissue 104a has been coagulated.

According to the third embodiment, the minimum value Zmin and maximum value Zmax of the impedance offered by a living tissue are calculated during a delivery period of high-frequency output power. According to the fourth embodiment, by making the most of the foregoing nature of living tissues, the initial value Iini of high-frequency current and the final value Iend thereof are measured during a delivery period of output power of the second level. The output power of the first level and the delivery period of the first time are calculated according to the relational expressions below:

Output power of the first level $$Wn+1=W1 \cdot \Delta I1/\Delta In \qquad (9)$$

Delivery period of the first time $$Tn+1=T1 \cdot \Delta I1/\Delta In \qquad (10)$$

where $\Delta In$ equals $(Iini-Iend)/Tn$, and n denotes the number of times of delivery ($n \geq 2$).

Next, an operation to be exerted by the fourth embodiment will be described below.

A user steps on the footswitch 105. According to the third embodiment, delivery of high-frequency output power is repeatedly continued and discontinued. Instead, the control circuit 128 instructs to alternately deliver, as shown in FIG. 33A, output power of the first level that is equal to a set value and output power of the second value that is smaller than the first level.

As shown in FIG. 33B, high-frequency current that is so feeble as not to heat the living tissue 104a is conducted during each pause period. The feeble high-frequency current increases gradually during the pause period (Iini_1–Iend_1 or Iini_2–Iend_2). When the living tissue 104a is coagulated over a wide range, the value of the feeble high-frequency current gets smaller than the one conducted during the immediately preceding pause period. Moreover, a rate at which the high-frequency current increases gets higher than the one observed during the immediately preceding pause period. Owing to this nature of living tissues, the control circuit 128 can judge over how wide a range the living tissue 104a has been coagulated.

Consequently, the fourth embodiment can provide the same advantage as the third embodiment. In addition, since the current sensors 151a and 151b alone are used to control delivery of output power, the configuration of the electric operation apparatus will be by no means complex but can be realized inexpensively. Moreover, according to the fourth embodiment, the measurement is achieved while high-frequency current whose value is smaller than a set value is delivered. The current sensors 151a and 151b are therefore unsusceptible to noises derived from high-frequency current. Therefore, delivery of output power can be controlled accurately. If high-frequency current conducted with the output power of the second level is too small to be measured, the control circuit 128 may use the output power of the first level that is larger than the second level to determine the output power of the first level to be delivered next and the next delivery period.

Similarly to the description made in conjunction with FIG. 25, the diathermic power supply 150 may further include the sensing high-frequency generation circuit 131 and the sensing power circuit 132 for supplying dc power to the sensing high-frequency generation circuit 131. The control circuit 128 measures high-frequency current. Consequently, delivery of output power can be controlled more accurately. In this case, preferably, the control circuit 128 measures high-frequency current conducted with the output power of the second level. This is because when the high-frequency current conducted with the output power of the second level is measured, influence of noises can be alleviated.

Moreover, similarly to the description made in conjunction with FIG. 27, the diathermic power supply 150 may further include the temperature sensor 133 so that the output power of the first level and the delivery period can be determined based on the detected temperature. In this case, when the diathermic power supply 150 starts delivering high-frequency output power, similarly to the one employed in the third embodiment, high-frequency output power whose level is larger than a set value may be delivered. Otherwise, the heater 134 may be additionally included in efforts to prevent adhesion of the living tissue 104a to the electrodes 103.

Moreover, an operator may be able to designate the initial value of the output power, the initial value of the delivery period, and the pause period during which delivery of output power is discontinued. The relational expressions that provide the set values of the output power and delivery period are not limited to those employed in the fourth embodiment but may be modified depending on a desired coagulated state.

Figure 34:
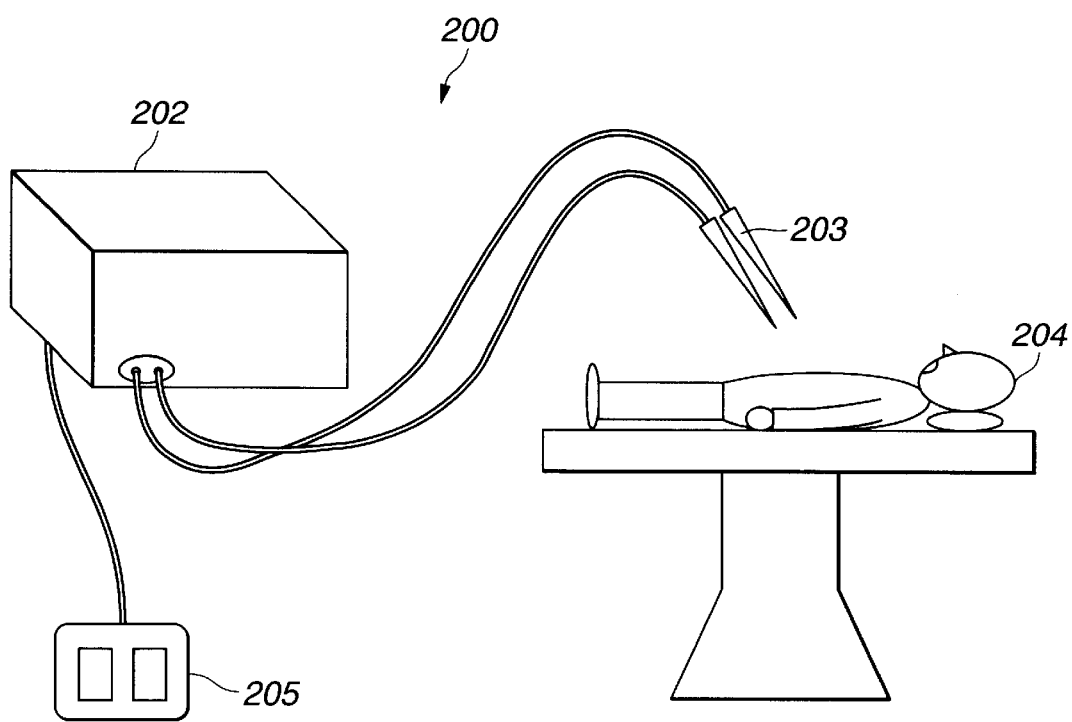
FIG. 34 shows the overall configuration of an electric operation apparatus in accordance with a fifth embodiment of the present invention.
Figure 35:
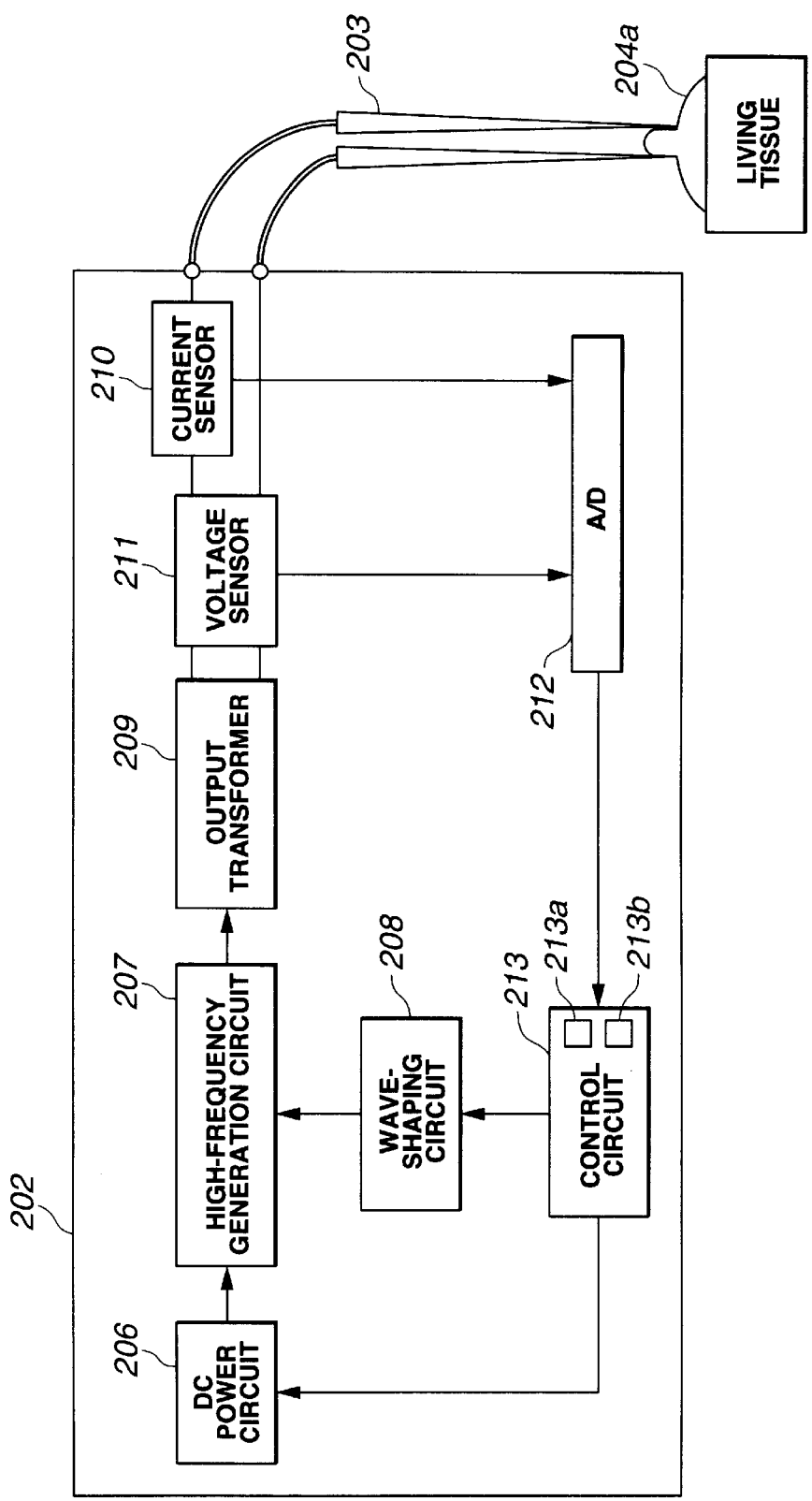
FIG. 35 is a circuit block diagram showing the configuration of a diathermic power supply shown in FIG. 34.
Figure 36:
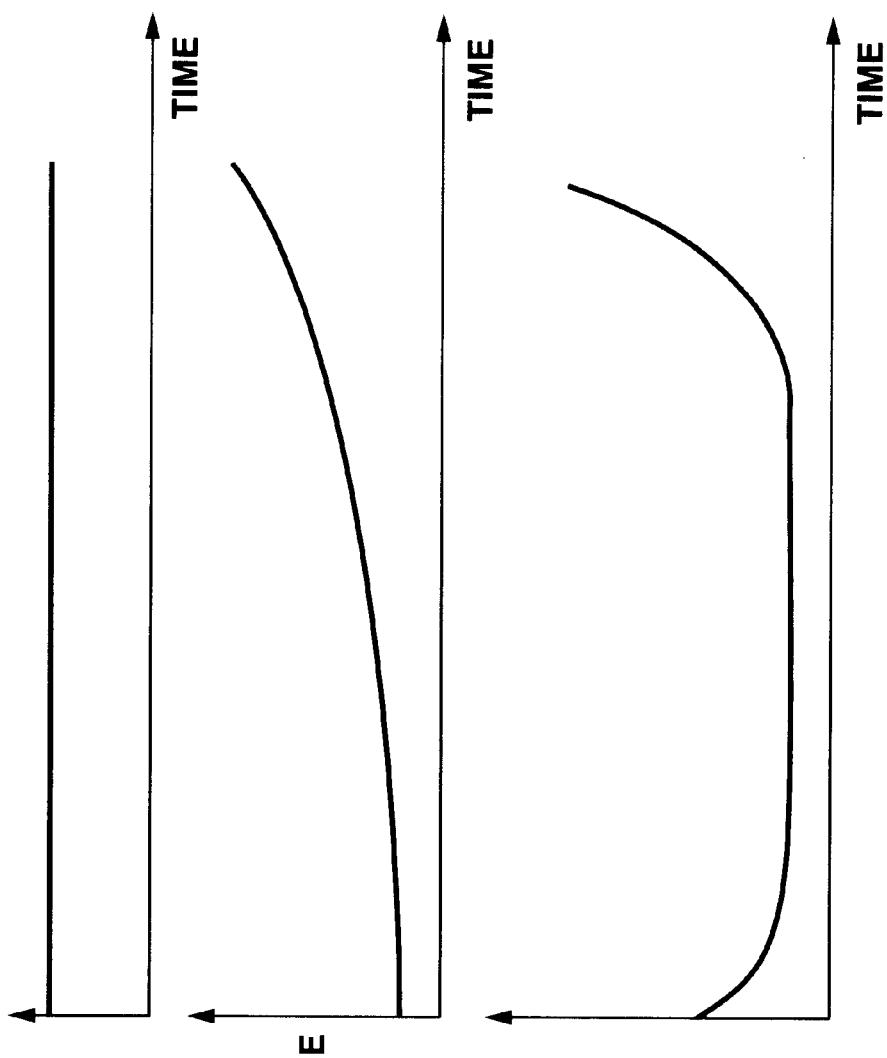
FIG. 36A to FIG. 36C are explanatory diagrams showing the relationships between time and high-frequency output power of a constant level, between time and the temperature of a living tissue, and between time and the impedance offered by the living tissue.
Figure 37:
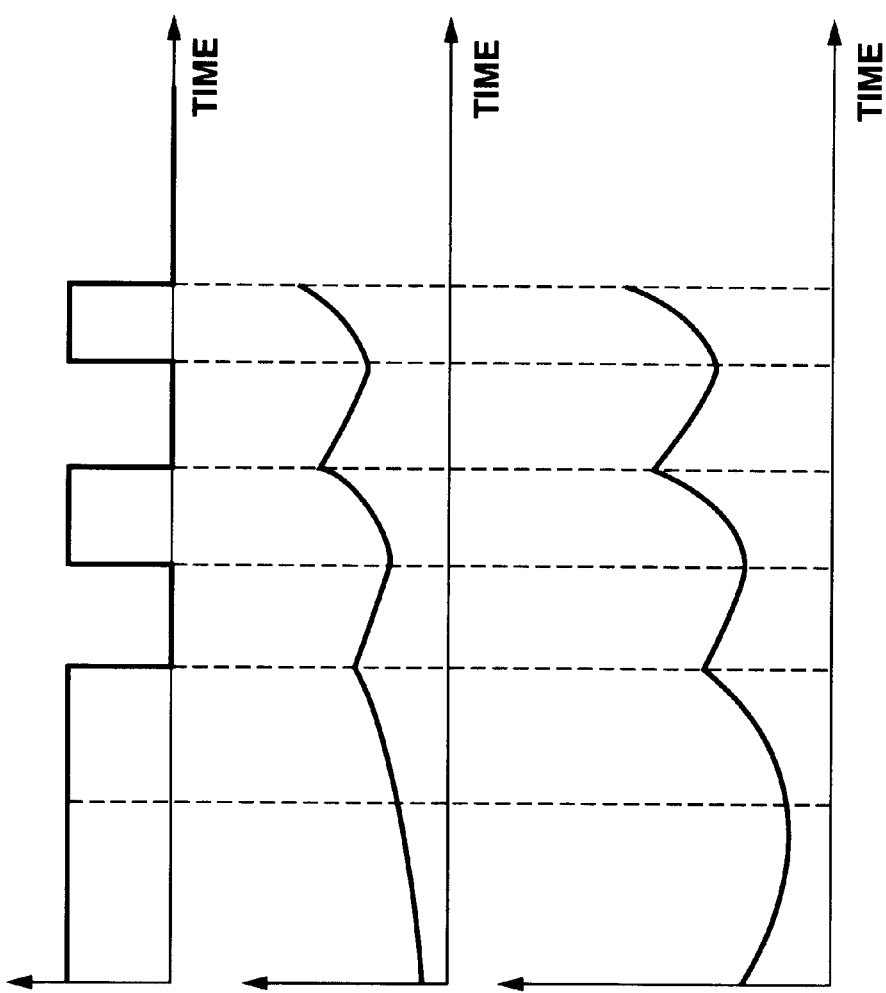
FIG. 37A to FIG. 37C are explanatory diagrams showing the relationships between time and high-frequency output power that is delivered intermittently, between time and the temperature of a living tissue, and between time and the impedance offered by the living tissue.
Figure 38:
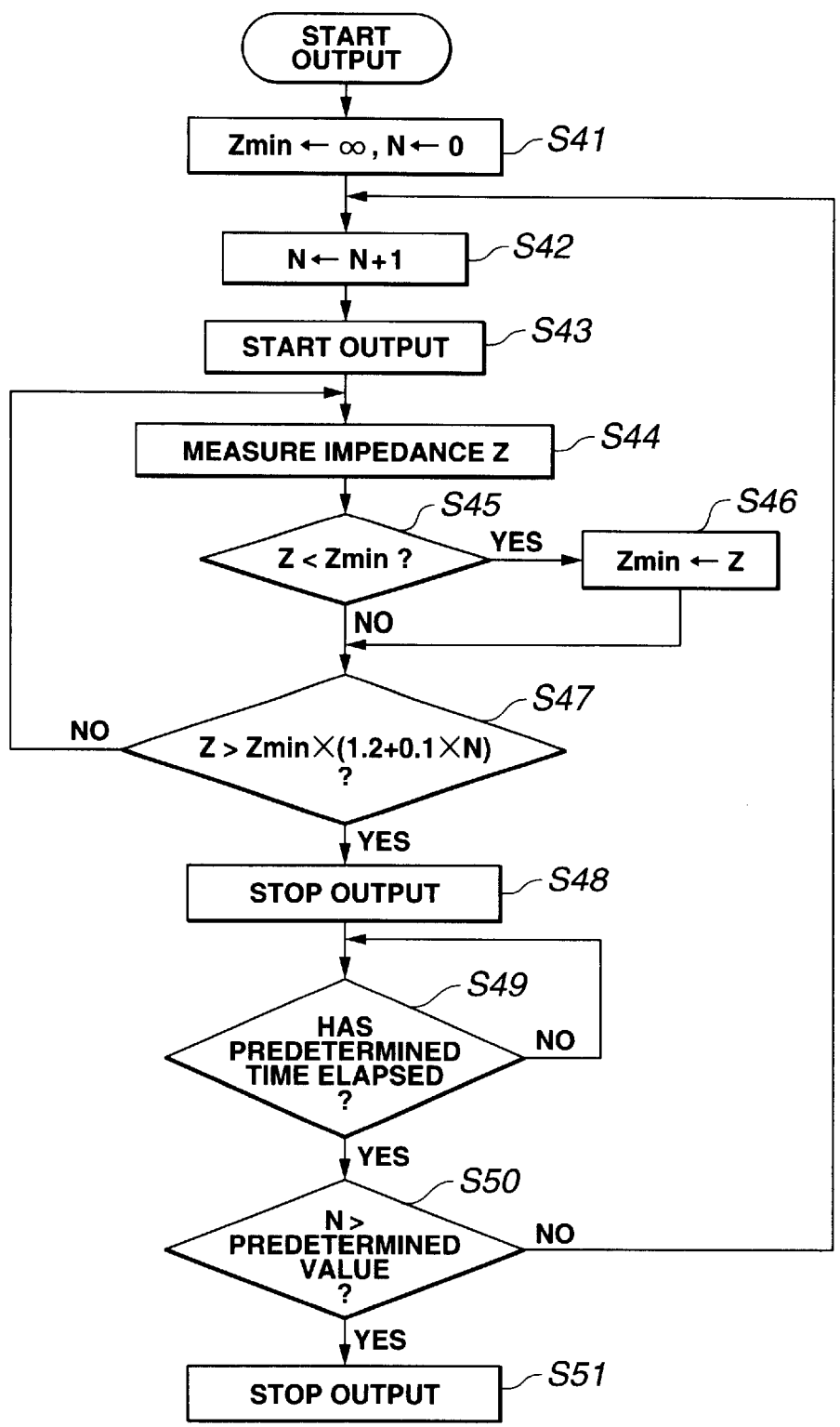
FIG. 38 is a flowchart describing a control sequence followed in a control circuit shown in FIG. 35.
Figures 39A, 39B:
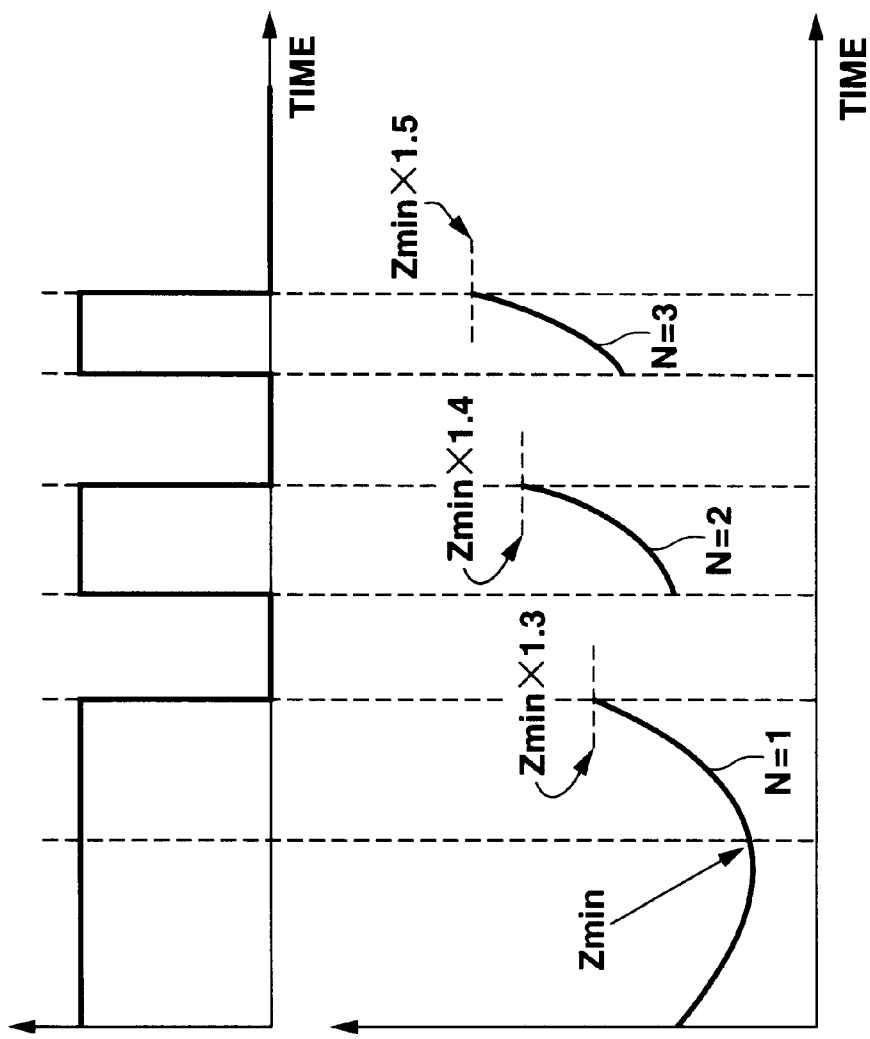
FIG. 39A and FIG. 39B are explanatory diagrams concerning a first operation to be exerted by a diathermic power supply that flows according to the control sequence described in the flowchart of FIG. 38.
Figures 40A, 40B:
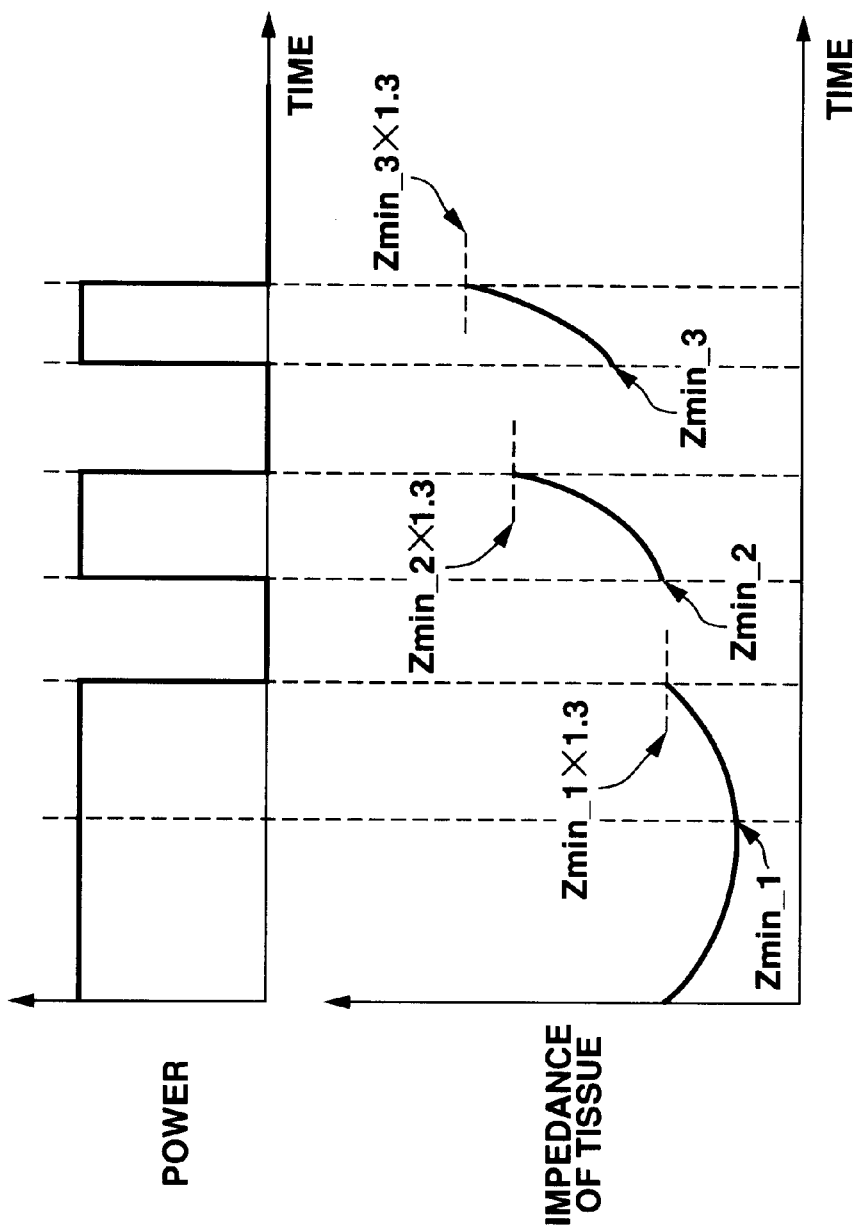
FIG. 40A and FIG. 40B are explanatory diagrams concerning a second operation to be exerted by the diathermic power supply that flows according to the control sequence described in the flowchart of FIG. 38.
Figures 42A, 42B:
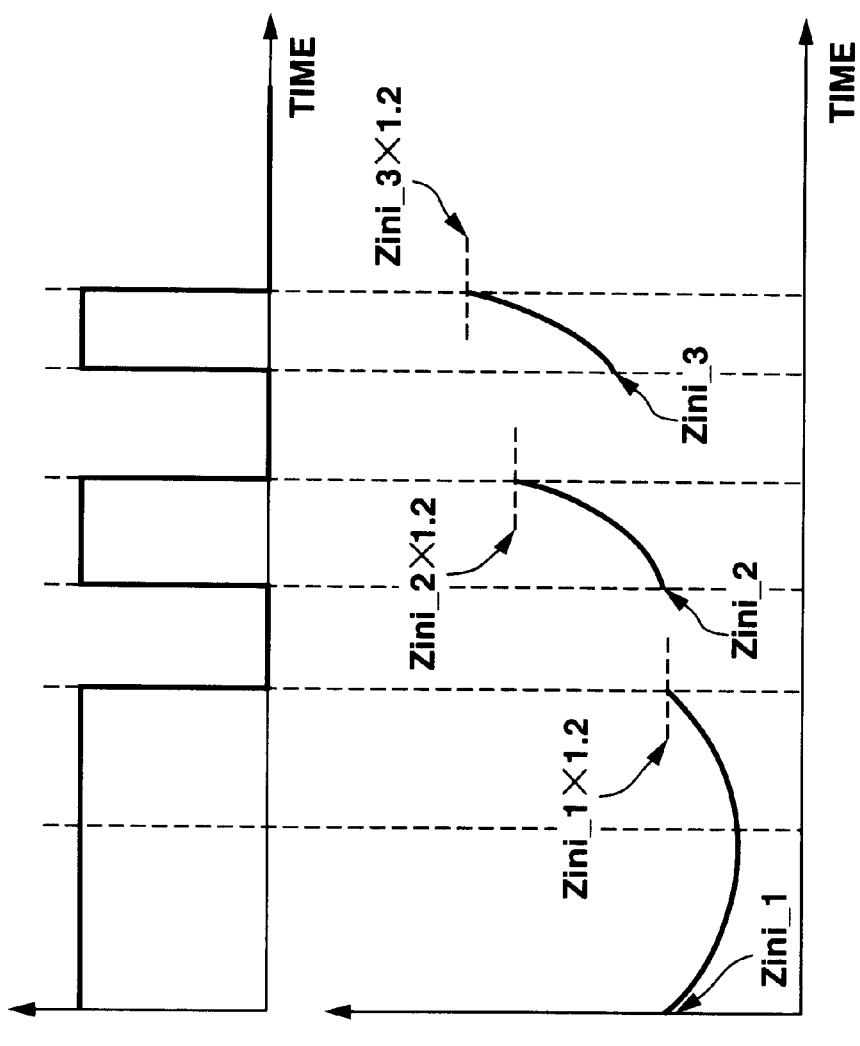
FIG. 42A and FIG. 42B are explanatory diagrams concerning a fourth operation to be exerted by the diathermic power supply that flows according to the control sequence described in the flowchart of FIG. 38.
Figure 44:
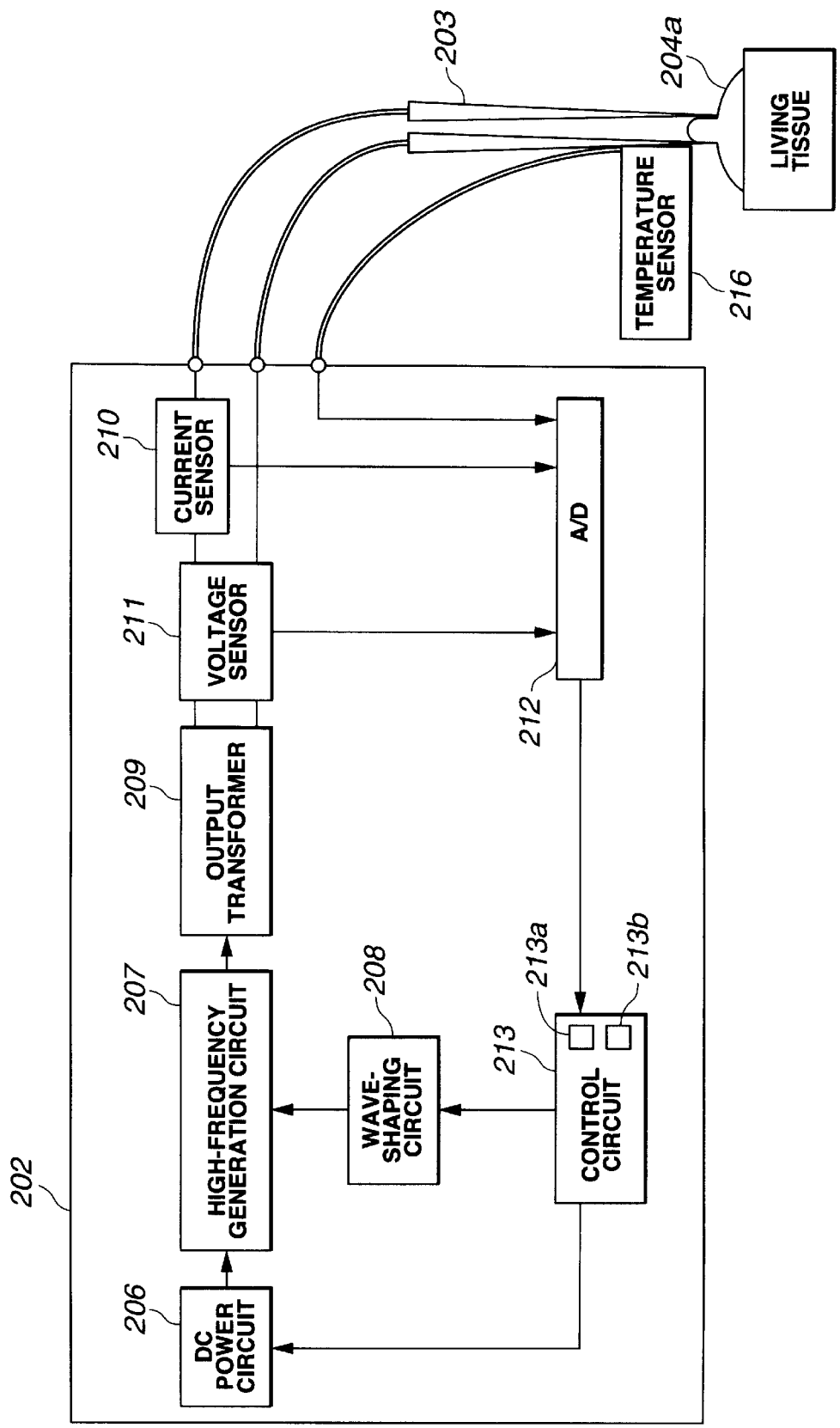
FIG. 44 is a circuit block diagram showing a diathermic power supply employed in a second variant.
Figures 45A, 45B:
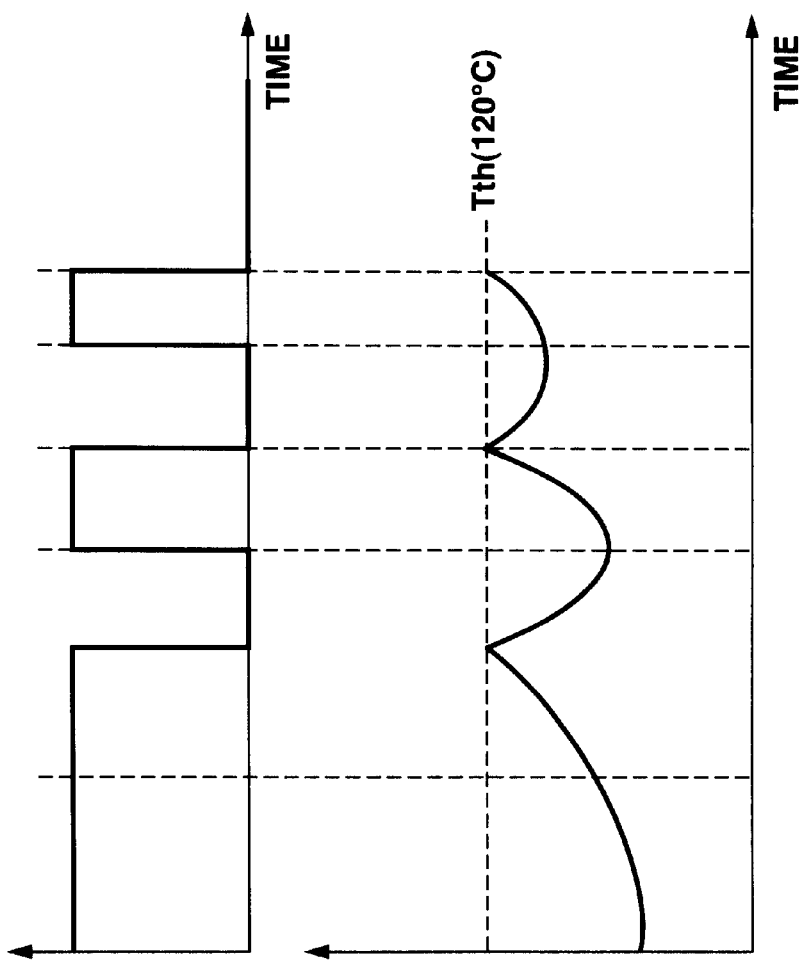
FIG. 45A and FIG. 45B are explanatory diagrams concerning an operation to be exerted by a diathermic power supply employed in the second variant shown in FIG. 44.

FIG. 34 to FIG. 45B are concerned with a fifth embodiment of the present invention. FIG. 34 shows the overall configuration of an electric operation apparatus in accordance with the fifth embodiment of the present invention. FIG. 35 is a circuit block diagram showing the circuitry of a diathermic power supply shown in FIG. 34. FIG. 36A to FIG. 36C are explanatory diagrams showing the relationships to time of high-frequency output power of a constant level, the temperature exhibited by a living tissue, and the impedance offered thereby. FIG. 36A is a graph showing a variation with the passage of time of high-frequency output power. FIG. 36B is a graph showing a change with the passage of time in the temperature exhibited by a living tissue which occurs with delivery of the high-frequency output power shown in FIG. 36A. FIG. 36C is a graph showing a change with the passage of time in the impedance offered by the living tissue which occurs with delivery of the high-frequency output power shown in FIG. 36A. FIG. 37A to FIG. 37C are explanatory diagrams showing the relationships to time of high-frequency output power that is delivered intermittently, the temperature exhibited by a living tissue, and the impedance offered thereby. FIG. 37A is a graph showing a variation with the passage of time of high-frequency output power. FIG. 37B is a graph showing a change with the passage of time in the temperature exhibited by a living tissue which occurs with delivery of the high-frequency output power shown in FIG. 37A. FIG. 37C is a graph showing a change with the passage of time in the impedance offered by the living tissue which occurs with delivery of the high-frequency output power shown in FIG. 37A. FIG. 38 is a flowchart describing a control sequence followed by a control circuit shown in FIG. 35. FIG. 39A and FIG. 39B are explanatory diagrams concerning a first operation to be exerted by the diathermic power supply that follows the control sequence described in the flowchart of FIG. 38. FIG. 39A is a graph showing a variation with the passage of time of high-frequency output power. FIG. 39B is a graph showing a change with the passage of time in the impedance offered by a living tissue which occurs with delivery of the high-frequency output power shown in FIG. 39A. FIG. 40A and FIG. 40B are explanatory diagrams concerning a second operation to be exerted by the diathermic power supply that follows the control sequence described in the flowchart of FIG. 38. FIG. 40A is a graph showing a variation with the passage of time of high-frequency output power. FIG. 40B is a graph showing a change with the passage of time in the impedance offered by a living tissue which occurs with delivery of the high-frequency output power shown in FIG. 40A. FIG. 41A and FIG. 41B are explanatory diagram concerning a third operation to be exerted by the diathermic power supply that follows the control sequence described in the flowchart of FIG. 38. FIG. 41A is a graph showing a variation with the passage of time of high-frequency output power. FIG. 41B is a graph showing a change with the passage of time in the impedance offered by a living tissue which occurs with delivery of the high-frequency output power shown in FIG. 41A. FIG. 42A and FIG. 42B are explanatory diagrams concerning a fourth operation to be exerted by the diathermic power supply that follows the control sequence described in the flowchart of FIG. 38. FIG. 42A is a graph showing a variation with the passage of time of high-frequency output power. FIG. 42B is a graph showing a change with the passage of time in the impedance offered by a living tissue which occurs with delivery of the high-frequency output power shown in FIG. 42A. FIG. 43 is a circuit block diagram showing the circuitry of a diathermic power supply employed in a first variant. FIG. 44 is a circuit block diagram showing the circuitry of a diathermic power supply employed in a second variant. FIG. 45A and FIG. 45B are explanatory diagrams concerning an operation to be exerted by the diathermic power supply employed in the second variant. FIG. 45A is a graph showing a variation with the passage of time of high-frequency output power. FIG. 45B is a graph showing a change with the passage of time in the temperature exhibited by a living tissue which occurs with delivery of the high-frequency output power shown in FIG. 45A.

As shown in FIG. 34, an electric operation apparatus 200 in accordance with a fifth embodiment includes a diathermic power supply 202. The diathermic power supply 202 is connected to a patient 204 via electrodes 203 that serve as a therapeutic accessory (operating instrument). Moreover, a footswitch 205 is connected to the diathermic power supply 202. The electrodes 203 shown in FIG. 34 are paired. Either single-pole electrodes or multi-pole electrodes may be used as the remedial electrodes 203.

As shown in FIG. 35, the diathermic power supply 202 consists mainly of a dc power circuit 206, a high-frequency generation circuit 207, a wave-shaping circuit 208, an output transformer 209, a current sensor 210, a voltage sensor 211, an A/D converter 212, a control circuit 213, and a display circuit (not shown). The dc power circuit 206 supplies dc power. The high-frequency generation circuit 207 converts the dc power supplied from the dc power circuit 206 into high-frequency output power. The wave-shaping circuit 208 instructs the high-frequency generation circuit 207 in the waveshape of high-frequency output power. The output transformer 209 transfers high-frequency output power generated by the high-frequency generation circuit 207 to the electrodes 203. The current sensor 210 detects high-frequency current that flows out from the output transformer 209. The voltage sensor 211 detects voltage induced by the output transformer 209. The A/D converter 212 converts signals transferred from the current sensor 210 and voltage sensor 211 respectively into digital signals. The control circuit 213 controls the dc power circuit 206 and wave-shaping circuit 208 according to the digital signals sent from the A/D converter 212. Biomedical information (impedance offered by a living tissue and temperature exhibited thereby) acquired based on the signals transferred from the current sensor 210 and voltage sensor 211 respectively is presented by the display circuit.

The control circuit 213 includes a timer 213a and a counter 213b. The timer 213a indicates passage of time since start of delivering high-frequency output power to the living tissue 204a. The counter 213b counts the number of times of delivery of high-frequency output power.

Among the foregoing components, the high-frequency generation circuit 207, wave-shaping circuit 208, and output transformer 209 constitute a high-frequency current generating means that delivers high-frequency output power with which high-frequency current is conducted. The control circuit 213 can switch supply and non-supply of dc power from the dc power circuit 206, and control the waveshape of high-frequency output power that is instructed by the wave-shaping circuit 208. Thus, the dc power supply 206 has its supply and non-supply of dc power from switched, whereby an output changing means for changing high-frequency output power is realized. The current sensor 210, voltage sensor 211, A/D converter 212, and part of the control circuit 213 constitute a coagulated state judging means that judges the coagulated state of the living tissue 204a from the result of detection of biomedical information of the living tissue 204a. Moreover, part of the control circuit 213 serves as a control means which controls the output changing means so that high-frequency output power will be varied. Specifically, the control means controls the output changing means so that delivery of high-frequency output power will be repeatedly continued and discontinued, and thus delivers high-frequency output power to the remedial electrodes 203. The control means has the ability to determine discontinuation of delivery of high-frequency output power, which is performed by the output changing means, according to biomedical information (impedance offered by a living tissue and temperature exhibited thereby).

According to the present embodiment, the impedance offered by a living tissue which is biomedical information is acquired by the control circuit 213. Specifically, the control circuit 213 calculates the impedance offered by the living tissue 204a clamped by the pair of electrodes 203 using a current value sent from the current sensor 210 and a voltage value sent from the voltage sensor 211. The control circuit 213 can judge the coagulated state of the living tissue 204a from the calculated impedance of the living tissue. The control circuit 213 may calculate the impedance of the living tissue using the current value sent from the current sensor 210 and the voltage value sent from the voltage sensor 211 during the delivery period or pause period of high-frequency output power to the remedial electrodes 203.

A user holds the pair of electrodes 203 included in the electric operation apparatus 200 so as to clamp the living tissue 204a of the patient 204, and turns on the footswitch 205. Consequently, high-frequency output power is delivered to the living tissue 204a clamped by the pair of electrodes 203. High-frequency current conducted with the high-frequency output power heats the living tissue 204a. Due to the heating, the living tissue 204a is denatured, and dried up with water thereof depleted. In due course, the living tissue 204a is coagulated. Even after the living tissue 204a is dried up, if delivery of high-frequency output power is continued, the living tissue 204a is carbonized. The carbonized living tissue 204a adheres to the electrodes 203. For preventing adhesion of the living tissue 204a to the electrodes 203, it is necessary to discontinue delivery of high-frequency output power as soon as the living tissue is dried up.

If high-frequency output power of a constant level shown in FIG. 36A is delivered to the living tissue 204a irrespective of how much time has elapsed, the living tissue 204a is heated. The temperature exhibited by the living tissue 204 gradually rises as shown in FIG. 36B along with progress in denaturation and drying of the living tissue 204a. On the other hand, the impedance offered by the living tissue decreases in an early stage as shown in FIG. 36C, remains constant for some time, and then abruptly increases with the dry of the living tissue 204a. Conventionally, when it is judged from the impedance or temperature of a living tissue that the living tissue has dried up, delivery of high-frequency output power is stopped.

In contrast, according to the present embodiment, high-frequency output power is, as shown in FIG. 37A, delivered intermittently. Consequently, the impedance offered by a living tissue decreases, as shown in FIG. 37C, with discontinuation of delivery of high-frequency power. Likewise, the temperature exhibited thereby drops, as shown in FIG. 37B, with the discontinuation of delivery of high-frequency power. When high-frequency output power is delivered again, the impedance of the living tissue increases, and the temperature thereof rises. According to the present embodiment, this procedure is repeated, whereby the living tissue 204a is held denatured and dried up. Carbonization of the living tissue and adhesion thereof derived from a rise in the temperature of the living tissue (which occurs when high-frequency output power is delivered continuously) can be prevented, but a large magnitude of high-frequency current can be conducted. Consequently, according to the present embodiment, compared with the aforesaid conventional method, the living tissue 204a can be coagulated over a wide range.

Furthermore, according to the present embodiment, the coagulated state of a living tissue can be judged from the temperature and impedance of the living tissue 204a that are calculated and measured during each delivery period, and discontinuation of delivery of high-frequency output power can be determined. Consequently, such an incidence will not take place that when delivery of output power is started next, high-frequency current conducted with the output power is not conducted efficiently because the living tissue 204a is coagulated excessively. Moreover, adhesion of the living tissue 204a to the electrodes 203 can be prevented.

An operation to be exerted by the present embodiment that utilizes the aforesaid nature of living tissues will be described in conjunction with the flowchart of FIG. 38.

As mentioned above, the living tissue 204a of the patient 204 is clamped with the pair of electrodes 203, and the footswitch 205 is turned on. When the footswitch 205 is stepped on, the control circuit 213 starts extending control as described in the flowchart of FIG. 38.

When the footswitch 105 is turned on, the control circuit 213 resets a minimum value Zmin of the impedance, which is offered by a living tissue during a delivery period during which high-frequency output power is delivered, to the infinite ∞ and the number of times of delivery of high-frequency output power to 0 at step S41 described in FIG. 38.

Thereafter, the control circuit 213 increments the number of times of delivery N at step S42, and starts delivery of high-frequency output power at step S43. The control circuit 213 receives signals from the current sensor 210 and voltage sensor 211 respectively via the A/D converter 212 at step S44. The impedance Z offered by the living tissue 204a is then calculated. Thereafter, the control circuit 213 judges at step S45 whether the calculated impedance value Z is smaller than the minimum value Zmin. If the impedance value Z is smaller than the minimum value Zmin, the minimum value Zmin is updated at step S46.

Thereafter, the control circuit 213 judges at step S47 whether the calculated impedance Z is smaller than a product of Zmin by (1.2+0.1×N). If the impedance Z is smaller than the product of Zmin by (1.2+0.1×N), step S44 and subsequent steps are repeated. The minimum value Zmin is the smallest value of the impedance offered by the living tissue after the footswitch 205 is stepped on.

If the calculated impedance Z is larger than Zmin×(1.2+ 0.1×N), the control circuit 213 discontinues delivery of output power at step S48. This is intended to judge the coagulated state of the living tissue from an increase in the impedance offered by the living tissue and to eventually prevent excessive coagulation of the living tissue 204a and adhesion thereof to the electrodes 203.

According to the present embodiment, a threshold is increased with every increment of the number of times of delivery for fear the degree of coagulation may gradually rise with every increment of the number of times of delivery.

Thereafter, the control circuit 213 judges at step S49 whether predetermined time that is, for example, 1 sec has elapsed as the pause period. When the predetermined time has elapsed, the control circuit 213 judges at step S50 whether the number of times of delivery has exceeded a predetermined value. If the number of times of delivery falls below the predetermined value, step S42 and subsequent steps are repeated. If the number of times of delivery has exceeded the predetermined value, the control circuit 213 stops delivery of output power at step S51.

FIG. 39A and FIG. 39B show a variation with the passage of time of high-frequency output power and a change with the passage of time in the impedance offered by a living tissue which occur when the control circuit 213 extends control as mentioned above.

Incidentally, any other conditional expression may be adopted instead of Z<Zmin×(1.2+0.1×N) employed in the present embodiment (shown in FIG. 38, FIG. 39A, and FIG. 39B). A plurality of expressions is stored in a memory incorporated in the apparatus in association with degrees of coagulation of the living tissue 204a. A user can select any of the expressions at an operator panel that is included in the electric operation apparatus and that is not shown.

According to the present embodiment (FIG. 38, FIG. 39A, and FIG. 39B), the control circuit 213 judges from the minimum value Zmin of the impedance, which is offered by a living tissue after the footswitch 205 is stepped on, whether delivery of output power should be discontinued. Alternatively, the control circuit 213 may judge from the minimum values Zmin_1, Zmin_2, Zmin_3, etc. calculated during respective delivery periods as shown in FIG. 40A and FIG. 40B whether delivery of output power should be discontinued.

FIG. 40A and FIG. 40B show a variation with the passage of time of high-frequency output power and a change with the passage of time in the impedance offered by a living tissue which occur when the control circuit 213 extends control using the minimum values.

A control sequence the control circuit 213 follows in this case is identical to the one described in the flowchart of FIG. 38. However, a conditional expression to be employed at step S47 is Z>Zmin_n×1.3 where n denotes a number assigned to each delivery period.

Furthermore, the control circuit 213 may compare Zmin_1 or Zmin_n−1 with Zmin_n and judge whether the difference has exceeded a specified value. Whether this condition that the difference should exceed the specified value is met may be judged at step S47 described in FIG. 38. Depending on the result of judgment, the control circuit 213 may discontinue delivery of output power.

Moreover, the control circuit 213 may use the initial value Zini of the impedance offered by a living tissue instead of the minimum value Zmin of the impedance to judge whether delivery of output power should be discontinued.

FIG. 41A and FIG. 41B show a variation with the passage of time of high-frequency output power and a change with the passage of time in the impedance offered by a living tissue which occur when the control circuit 213 extends control as mentioned above.

A control sequence the control circuit 213 follows in this case is identical to the one described in the flowchart of FIG. 38. A conditional expression to be employed at step S47 is Z>Zini×(1.1+0.1×N) where n denotes a number assigned to each delivery period.

Furthermore, the control circuit 213 may use the initial values Zini_1, Zini_2, Zini_3, etc. of the impedance offered by a living tissue which are calculated during respective delivery periods to judge whether delivery of output power should be discontinued.

FIG. 42A and FIG. 42B show a variation with the passage of time of high-frequency output power and a change with the passage of time in the impedance offered by a living tissue which occur when the control circuit 213 extends control using the initial values.

A control sequence the control circuit 213 follows in this case is identical to the one described in the flowchart of FIG. 38. A conditional expression to be employed at step S47 is Z>Zini_n×1.2 where n denotes a number assigned to each delivery period, that is, 1, 2, 3, or the like.

Furthermore, whether the condition that the difference between Zini_1 or Zini_n=1 and Zini_n which are compared with each other should be larger than a specified value is met may be judged at step S47 described in FIG. 38. Depending on whether the condition is met, the control circuit 213 may discontinue delivery of output power.

FIG. 43 and FIG. 44 show other examples of the circuitry of a diathermic power supply.

The circuitry shown in FIG. 43 includes, in addition to the same components as the circuitry shown in FIG. 35, a sensing high-frequency generation circuit 214 and a sensing power circuit 215 that supplies dc power to the sensing high-frequency generation circuit 214. Consequently, the impedance offered by the living tissue 204a that is an electric parameter can be calculated using high-frequency output power for use in sensing that is different from high-frequency output power for use in remedy. Consequently, the diathermic power supply shown in FIG. 43 can more accurately control continuation and discontinuation of delivery of high-frequency output power.

The circuitry shown in FIG. 44 includes, in addition to the same components as those of the circuitry shown in FIG. 35, a temperature sensor 216. When the temperature of the living tissue 204a has, as shown in FIG. 45B, reached a predetermined value Tth that is 120° or the like, delivery of high-frequency output power may be discontinued as shown in FIG. 45A.

Instead of repeating continuation and discontinuation of delivery of high-frequency output power, the control circuit 213 may extend control to alternately delivery output power of the first level that is equal to a set value and output power of the second level smaller than the first level. Nevertheless, the same advantage can be provided.

The predetermined time that elapses after discontinuation and that is treated at step S49 in FIG. 38 may be able to be set based on a desired coagulated state by a user. Alternatively, the predetermined time may be varied depending on the impedance offered by a living tissue and the temperature exhibited thereby.

Furthermore, since the control circuit 213 may not be able to accurately calculate the impedance offered by a living tissue, an upper limit may be set for the number of times of delivery N. Repetition of continuation and discontinuation of delivery of output power may be varied depending on the impedance offered by the living tissue 204a and the temperature exhibited thereof. This is intended to avoid unnecessary delivery of output power after a desired coagulated state is attained.

As mentioned above, according to the fifth embodiment, continuation and discontinuation of delivery of high-frequency output power is repeated. Furthermore, delivery of high-frequency output power is discontinued based on the coagulated state of the living tissue 204a. Consequently, high-frequency output power can be delivered repeatedly with the temperature of the living tissue 204a held within a range of temperature value that does not bring about carbonization. Consequently, according to the fifth embodiment, the living tissue 204a is reliably coagulated and carbonization of the living tissue and adhesion thereof to the electrodes 203 can be prevented.

Figures 51A, 51B:
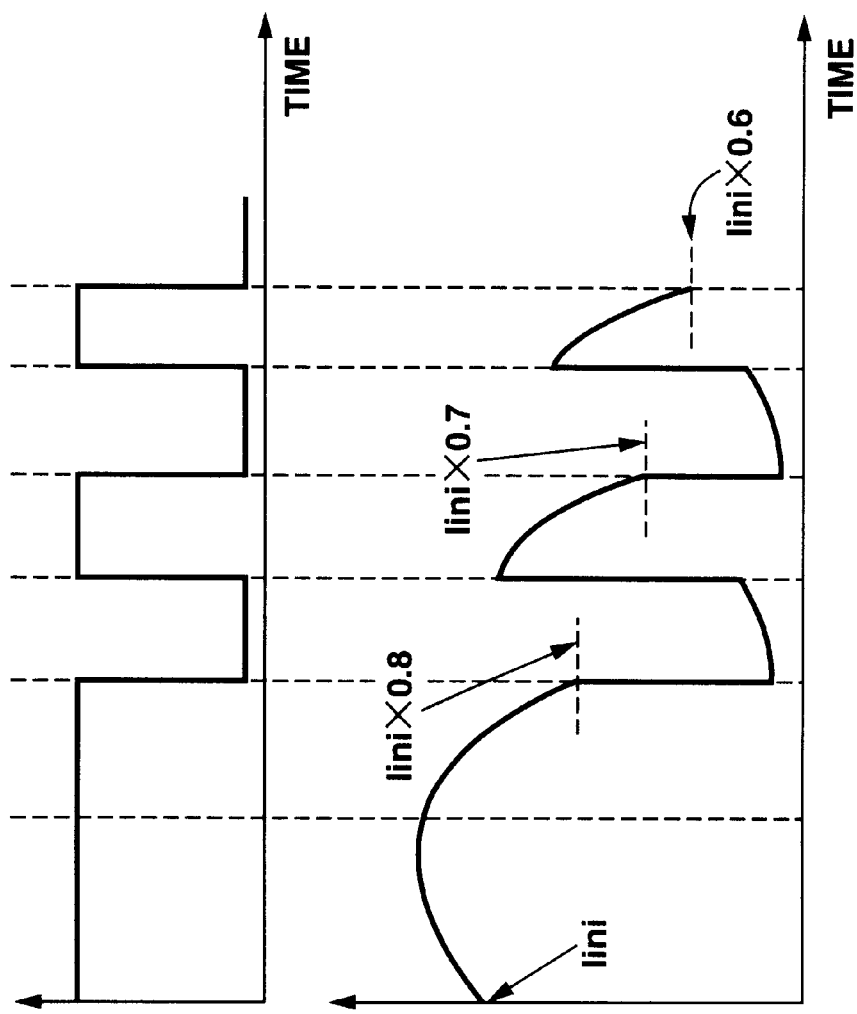
Figures 52A, 52B:
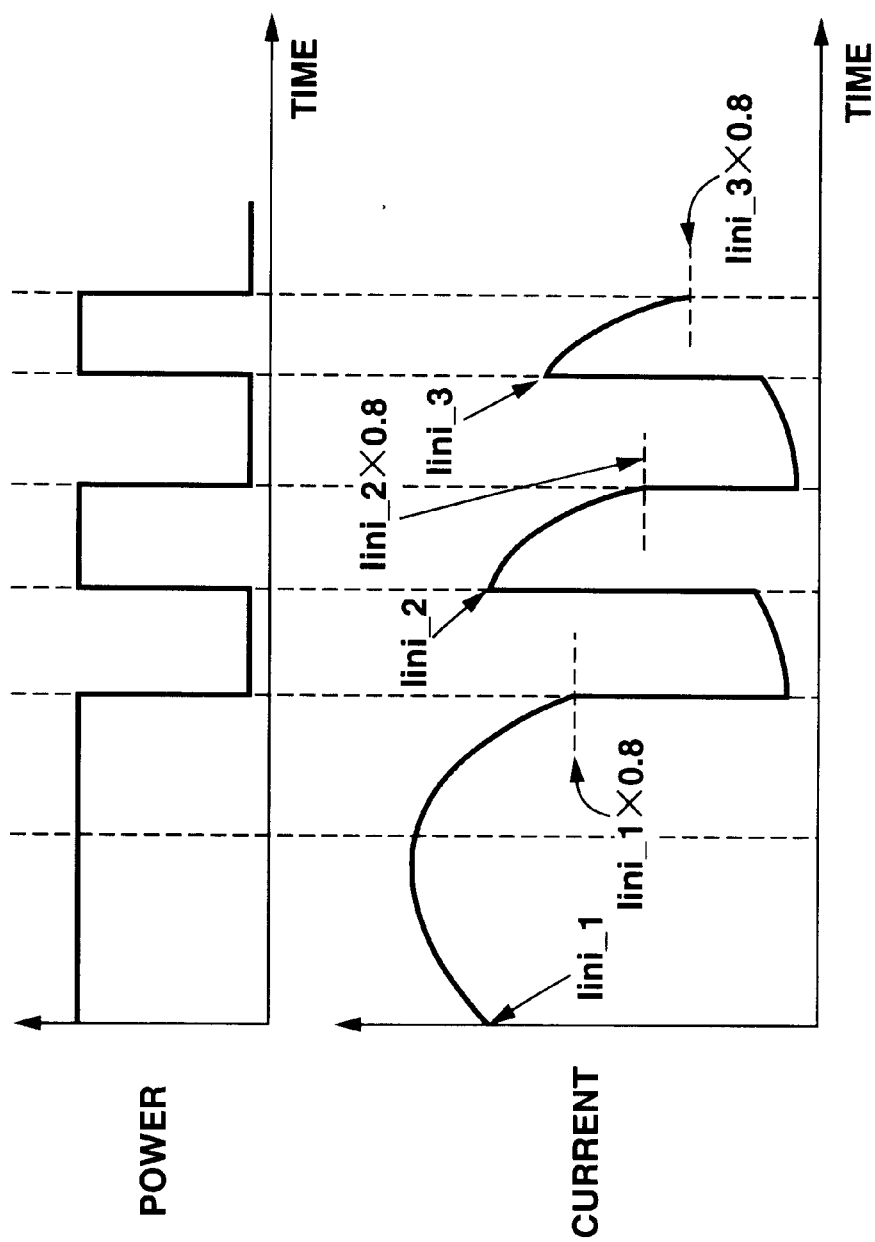

FIG. 46 to FIG. 52B are concerned with a sixth embodiment of the present invention. FIG. 46 is a circuit block diagram showing the circuitry of a diathermic power supply employed in the sixth embodiment of the present invention. FIG. 47A to FIG. 47C are first explanatory diagrams concerning an operation to be exerted by the diathermic power supply shown in FIG. 46. FIG. 47A is a graph showing a variation with the passage of time of high-frequency output power. FIG. 47B is a graph showing a change with the passage of time in the temperature exhibited by a living tissue which occurs with delivery of the high-frequency output power shown in FIG. 47A. FIG. 47C is a graph showing a variation with the passage of time of high-frequency current conducted with the high-frequency output power shown in FIG. 47A. FIG. 48A to FIG. 48C are second explanatory diagrams concerning an operation to be exerted by the diathermic power supply shown in FIG. 46. FIG. 48A is a graph showing a variation with the passage of time of high-frequency output power. FIG. 48B is a graph showing a change with the passage of time in the temperature exhibited by a living tissue which occurs with delivery of the high-frequency output power shown in FIG. 48A. FIG. 48C is a graph showing a variation with the passage of time of high-frequency current conducted with the high-frequency output power shown in FIG. 48A. FIG. 49A and FIG. 49B are third explanatory diagrams concerning an operation to be exerted by the diathermic power supply shown in FIG. 46. FIG. 49A is a graph showing a variation with the passage of time of high-frequency output power. FIG. 49B is a graph showing a variation with the passage of time of high-frequency current conducted with the high-frequency output power shown in FIG. 49A. FIG. 50A and FIG. 50B are fourth explanatory diagrams concerning an operation to be exerted by the diathermic power supply shown in FIG. 46. FIG. 50A is a graph showing a variation with the passage of time of high-frequency output power. FIG. 50B is a graph showing a variation with the passage of time of high-frequency current conducted with the high-frequency output power shown in FIG. 50A. FIG. 51A and FIG. 51B are fifth explanatory diagrams concerning an operation to be exerted by the diathermic power supply shown in FIG. 46. FIG. 51A is a graph showing a variation with the passage of time of high-frequency output power. FIG. 51B is a graph showing a variation with the passage of time of high-frequency current conducted with the high-frequency output power shown in FIG. 51A. FIG. 52A and FIG. 52B are sixth explanatory diagrams concerning an operation to be exerted by the diathermic power supply shown in FIG. 46. FIG. 52A is a graph showing a variation with the passage of time of high-frequency output power. FIG. 52B is a graph showing a variation with the passage of time of high-frequency current conducted with the high-frequency output power shown in FIG. 52A.

The components of the sixth embodiment are nearly identical to those of the fifth embodiment. A different alone will be described below. The same reference numerals will be assigned to identical components, and the description of the identical components will be omitted.

In the sixth embodiment of the present invention, as shown in FIG. 46, only the current sensor 210 that detects high-frequency current which flows out from the output transformer 209 is used to measure high-frequency output power.

Among the components shown in FIG. 46, the high-frequency generation circuit 207, wave-shaping circuit 208, and output transformer 209 constitute a high-frequency current generating means that delivers high-frequency output power with which high-frequency current is conducted. The control circuit 213 switches supply and non-supply of dc power from the dc power circuit 206, and controls a waveshape for high-frequency current given by the wave-shaping circuit 208. The dc power circuit 206 has its supply and non-supply of dc power switched by the control circuit 213, whereby an output changing means that changes high-frequency output power is realized. The current sensor 210, A/D converter 212, and part of the control circuit 213 constitute a coagulated state judging means that calculates biomedical information of the living tissue 204a and that judges the coagulated state of the living tissue 204a from the result of calculation. Moreover, part of the control circuit 213 serves as a control means that controls the output changing means 6 so that high-frequency output power can be varied. Specifically, the control means controls the output changing means 6 so that output power of the first level and output power of the second level smaller than the first level will be delivered alternately. The control means thus deliver output power to the remedial electrodes 203. The control means has the ability to instruct the output changing means 6 to change the output powers of the first and second levels according to biomedical information (impedance offered by a living tissue and temperature exhibited thereby) transferred from the coagulated state judging means.

According to the present embodiment, the control circuit 213 uses a current value transferred from the current sensor 210 to measure high-frequency output power delivered to the pair of electrodes 203. The control circuit 213 judges the coagulated state of the living tissue 204a from the measured high-frequency output power. The control circuit 213 uses the current value transferred from the current sensor 210 to measure high-frequency output power. The measurement may be performed while high-frequency output power of the first level is delivered to the remedial electrodes 203 or while high-frequency output power of the second level is delivered to the remedial electrodes 203.

As described in relation to the fifth embodiment, when high-frequency output power of a constant level shown in FIG. 47A is delivered to the living tissue 204a irrespective of how much time has elapsed, coagulation of the living tissue 204a progresses. The temperature of the living tissue 204a rises as shown in FIG. 47B. The impedance offered by the living tissue 204a changes accordingly. When the impedance increases, high-frequency current decreases. As shown in FIG. 47C, the high-frequency current behaves contrary to the impedance of the living tissue (see FIG. 36C). Namely, the high-frequency current increases in an early stage, remains nearly constant for some time, and then abruptly decreases with the dry of the living tissue 204a.

High-frequency output power is, as shown in FIG. 48A, intermittently delivered to the living tissue 204a, and high-frequency current is, as shown in FIG. 48C, conducted intermittently. In this case, the temperature of the living tissue 204a changes as shown in FIG. 48B. The impedance offered by the living tissue 204a changes accordingly. The high-frequency current decreases during each delivery period of high-frequency output power. After delivery of high-frequency output power is discontinued, when high-frequency output power is delivered again, a large magnitude of high-frequency current is conducted. This is because the temperature of the living tissue drops during the pause period. Incidentally, the temperature of the living tissue rises as shown in FIG. 48B (similarly to the one shown in FIG. 37B).

The control circuit 213 may judge the coagulated state of the living tissue 204a from the high-frequency current and the temperature of the living tissue 204a, and determine based on the result of judgment that delivery of output power should be discontinued. Similarly to the fifth embodiment, such an incident will not take place that when delivery of high-frequency output power is started next, high-frequency output power cannot be delivered efficiently because the living tissue 204a is coagulated excessively. Moreover, adhesion of the living tissue 204a to the electrodes 203 can be prevented.

An operation to be exerted by the sixth embodiment that utilizes the nature of living tissues will be described below.

Figures 49A, 49B:
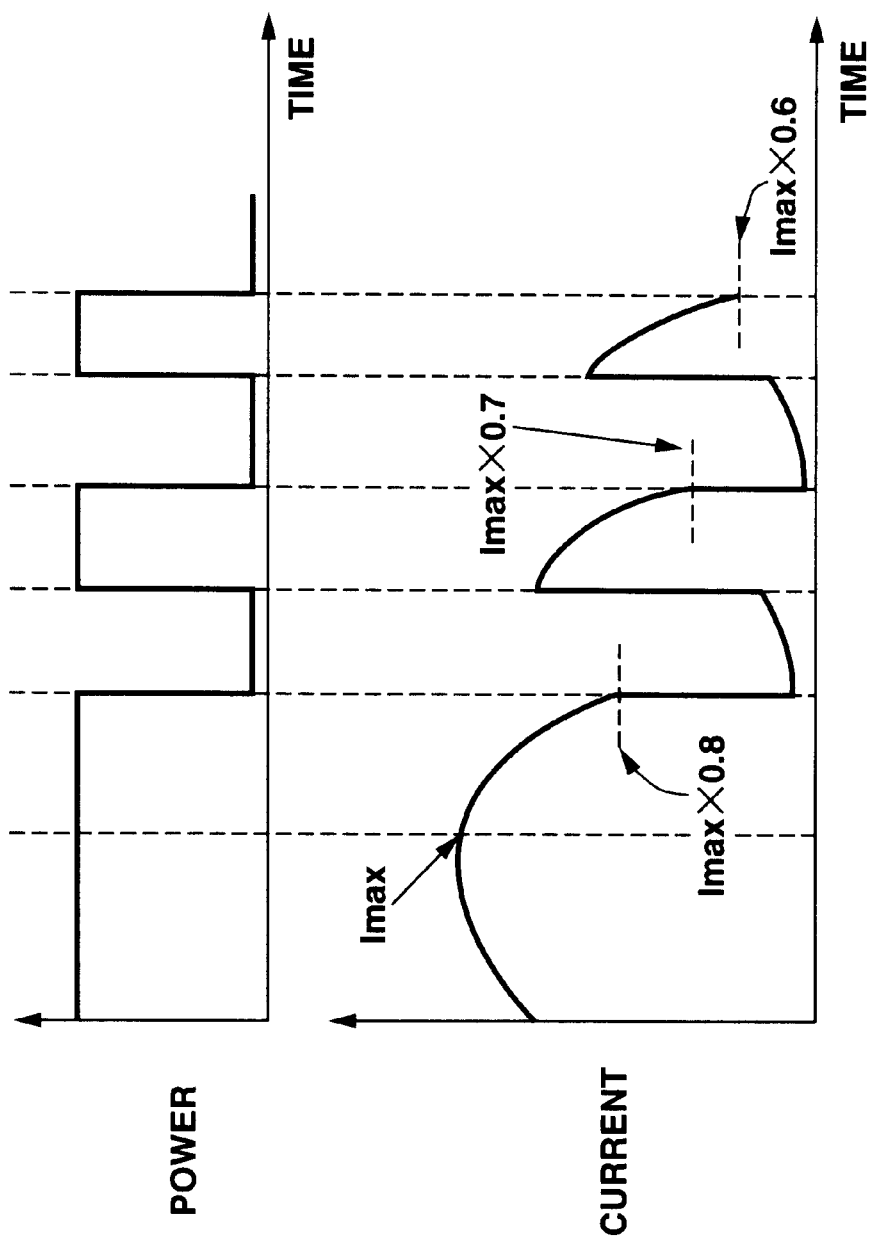
FIG. 49A and FIG. 49B are third explanatory diagrams concerning an operation to be exerted by the diathermic power supply shown in FIG. 46.

A user steps on the footswitch 105. The control circuit employed in the fifth embodiment extends control to repeatedly continue and discontinue delivery of high-frequency output power. In contrast, the control circuit 213 employed in the present embodiment extends control to, as shown in FIG. 49A, alternately deliver output power of the first level that is equal to a set value and output power of the second level smaller than the first level. The output power of the second level is output power that does not substantially raise the temperature of the living tissue 204a. According to the fifth embodiment, the impedance Z offered by the patient 204 and the minimum value Zmin of the impedance are used to determine whether delivery of output power should be discontinued. Similarly to the fifth embodiment, according to the present embodiment, the control circuit 213 uses the measured high-frequency current I and the maximum value Imax thereof to determine whether the output power of the first level should be changed to the output power of the second level.

FIG. 49A and FIG. 49B show a variation with the passage of time of high-frequency output power and a variation with the passage of time of high-frequency current which occur when the control circuit 213 extends control using the measured current I and maximum value Imax.

A control sequence the control circuit 213 follows is identical to the one described in the flowchart of FIG. 38. A conditional expression to be employed at step S47 is I<Imax×I(0.9−0.1×N), wherein the fact that the high-frequency current decreases with progress in coagulation of the living tissue 204a is utilized. Herein, Imax denotes the maximum value of the high-frequency current I detected at start of delivery.

Similarly to the fifth embodiment, in the sixth embodiment (FIG. 49A and FIG. 49B), any other expression may be adopted instead of I<Imax×(0.9−0.1×N). A plurality of conditional expressions is stored in a memory incorporated in the apparatus in association with degrees of coagulation of the living tissue 204a. A user can select any of the conditional expressions at an operator panel, which is not shown, included in the electric operation apparatus.

According to the present embodiment (FIG. 49A and FIG. 49B), the control circuit 213 uses the maximum value Imax of high-frequency current conducted after the footswitch 205 is stepped on to judge whether the output power of the first level should be changed to the output power of the second level. Alternatively, the control circuit 213 may use maximum values Imax_1, Imax_2, Imax_3, etc. of high-frequency current, which are measured during respective delivery periods, to judge whether the output power of the first level should be changed to the output power of the second level.

FIG. 50A and FIG. 50B show a variation with the passage of time of high-frequency output power and a variation with the passage of time of high-frequency current which occur when the control circuit 213 extends control using the maximum values.

A control sequence the control circuit 213 follows in this case is identical to the one described in the flowchart of FIG. 38. However, a conditional expression to be employed at step S47 is I<Imax_n×0.8 where n denotes a number assigned to each delivery period, that is, 1, 2, 3, or the like.

Alternatively, the control circuit 213 may use an initial value Iini of high-frequency current instead of the maximum value Imax thereof to judge whether the output power of the first level should be changed to the output power of the second level.

FIG. 51A and FIG. 51B show a variation with the passage of time of high-frequency output power and a variation with the passage of time of high-frequency current which occur when the control circuit 213 extends control using the initial value Iini.

A control sequence the control circuit 213 follows in this case is identical to the one described in the flowchart of FIG. 38. However, a conditional expression to be employed at step S47 is I<Iini×(0.9−0.1×N) where n denotes a number assigned to each delivery period, that is, 1, 2, 3, or the like.

Otherwise, the control circuit 213 may use initial values Iini_1, Iini_2, Iini_3, etc. of high-frequency current, which are measured during respective delivery periods, to judge whether the output power of the first level should be changed to the output power of the second level.

FIG. 52A and FIG. 52B show a variation with the passage of time of high-frequency output power and a variation with the passage of time of high-frequency current which occur when the control circuit 213 extends control using the initial values.

A control sequence the control circuit 213 follows in this case is identical to the one described in the flowchart of FIG. 38. However, a conditional expression to be employed at step S47 is I<Iini_n×(0.8) where n denotes a number assigned to each delivery period, that is, 1, 2, 3, or the like.

The control circuit 213 may convert high-frequency current that is biomedical information into the impedance offered by a living tissue. In this case, the maximum value Imax of high-frequency current contained in the conditional expression described in conjunction with FIG. 49 to FIG. 52 is replaced with the minimum value Zmin of the impedance. The conditional expression or expressions described in FIG. 38 to FIG. 40B may be adopted.

Similarly to the fifth embodiment (FIG. 43), the sensing high-frequency generation circuit 214 and the sensing power circuit 215 for supplying power to the sensing high-frequency generation circuit 214 may be added to the diathermic power supply shown in FIG. 46. High-frequency output power that is used for sensing and different from high-frequency output power for use in remedy may be measured, whereby high-frequency output power of the first level and high-frequency output power of the second level can be switched accurately.

Similarly to the fifth embodiment (FIG. 44), the temperature sensor 216 may be added. Consequently, when the temperature of a living tissue has, as shown in FIG. 45B, reached the predetermined value that is 120° or the like, alternation of the output power of the first level and the output value of the second level may be terminated.

Similarly to the fifth embodiment, continuation and discontinuation of delivery of output power may be repeated. Nevertheless, the same advantage can be provided.

As mentioned above, according to the sixth embodiment, delivery of high-frequency output power is repeatedly continued and discontinued. Besides, delivery of high-frequency output power is discontinued depending on the state of the living tissue 204a. Consequently, high-frequency output power can be delivered repeatedly with the temperature of the living tissue 204a held within a range of temperature values that does not bring about carbonization. Therefore, according to the sixth embodiment, the living tissue 204a can be coagulated reliably, while carbonization of the living tissue 204a and adhesion thereof to the electrodes 203 can be prevented.

According to the sixth embodiment, the current sensor 210 alone is used to control delivery of output power. This results in the diathermic power supply that is by no means complex but inexpensive.

According to the present invention, it is apparent that a wide range of different embodiments can be constructed based on the invention without a departure from the spirit and scope of the invention. The present invention is limited to the appended claims but not restricted to any specific embodiments.

What is claimed is:

1. An electric operation apparatus comprising:

a high-frequency current generating means for delivering high-frequency output power with which high-frequency current is conducted to a living tissue for the purpose of remedy;

an output changing means for changing high-frequency output power that is delivered by said high-frequency current generating means;

a control means for controlling said output changing means so that delivery of high-frequency output power will be repeatedly continued and discontinued;

a coagulated state judging means that judges the coagulated state of the living tissue, said control means controlling said output changing means according to the result of judgment made by said coagulated state judging means wherein said coagulated state judging means judges the coagulated state of the living tissue by comparing biomedical information, which is acquired during each delivery period during which high-frequency output power is delivered or during each pause period during which delivery of high-frequency output power is discontinued, with biomedical information acquired during an immediately preceding delivery period of high-frequency output power or during an immediately preceding pause period thereof.

2. An electric operation apparatus according to claim 1, wherein said coagulated state judging means judges the coagulated state of the living tissue by comparing at least one of a maximum value and a minimum value of biomedical information, which are acquired during each delivery period during which high-frequency output power is delivered or during each pause period during which delivery of high-frequency output power is discontinued, with at least one of a maximum value and a minimum value of biomedical information that are acquired during an immediately preceding delivery period of high-frequency output power or during an immediately preceding pause period thereof.

3. An electric operation apparatus according to claim 1, wherein said coagulated state judging means judges the coagulated state of the living tissue by comparing at least one of biomedical information acquired at the start of each delivery period during which high-frequency output power is delivered and biomedical information acquired during each pause period during which delivery of high-frequency output power is discontinued with at least one of biomedical information acquired at the start of the first delivery period of high-frequency output power and biomedical information acquired during the first pause period thereof.

4. An electric operation apparatus according to claim 3, wherein said coagulated state judging means judges the coagulated state of the living tissue by comparing biomedical information, which is acquired at the start of each delivery period during which high-frequency output power is delivered, with biomedical information acquired during an immediately preceding pause period during which delivery of high-frequency output power is discontinued.

* * * * *